(12) United States Patent
Grindrod et al.

(10) Patent No.: US 11,584,733 B2
(45) Date of Patent: Feb. 21, 2023

(54) SELECTIVE HISTONE DEACETYLASE INHIBITORS FOR THE TREATMENT OF HUMAN DISEASE

(71) Applicant: Shuttle Pharmaceuticals, Inc., Rockville, MD (US)

(72) Inventors: Scott Grindrod, Rockville, MD (US); Mira Jung, Rockville, MD (US); Milton Brown, Rockville, MD (US); Anatoly Dritschilo, Rockville, MD (US)

(73) Assignee: Shuttle Pharmaceuticals, Inc., Rockville, MD (US)

( * ) Notice: Subject to any disclaimer, the term of this patent is extended or adjusted under 35 U.S.C. 154(b) by 96 days.

(21) Appl. No.: 17/315,567

(22) Filed: May 10, 2021

(65) Prior Publication Data

US 2021/0261523 A1 Aug. 26, 2021
US 2022/0348551 A9 Nov. 3, 2022

Related U.S. Application Data

(63) Continuation of application No. 16/476,006, filed as application No. PCT/US2018/012971 on Jan. 9, 2018, now Pat. No. 11,034,667.

(60) Provisional application No. 62/444,003, filed on Jan. 9, 2017.

(51) Int. Cl.
| | |
|---|---|
| *C07D 401/04* | (2006.01) |
| *A61P 35/00* | (2006.01) |
| *C07D 211/88* | (2006.01) |
| *A61K 45/06* | (2006.01) |

(52) U.S. Cl.
CPC ............ *C07D 401/04* (2013.01); *A61P 35/00* (2018.01); *C07D 211/88* (2013.01); *A61K 45/06* (2013.01)

(58) Field of Classification Search
CPC ..... C07D 401/04; C07D 211/88; A61P 35/00; A61K 45/06; A61K 31/45; A61K 31/454
See application file for complete search history.

(56) References Cited

U.S. PATENT DOCUMENTS

| | | |
|---|---|---|
| 3,163,639 A | 12/1964 | Hitchings et al. |
| 3,968,249 A | 7/1976 | Bernstein et al. |
| 4,130,648 A | 12/1978 | Kijima et al. |
| 4,808,614 A | 2/1989 | Hertel |
| 4,966,891 A | 10/1990 | Fujiu et al. |
| 4,992,445 A | 2/1991 | Lawter et al. |
| 5,001,139 A | 3/1991 | Lawter et al. |
| 5,023,252 A | 6/1991 | Hseih |
| 5,344,932 A | 9/1994 | Taylor |
| 5,453,497 A | 9/1995 | Kamiya et al. |
| 5,455,044 A | 10/1995 | Kim et al. |
| 5,464,826 A | 11/1995 | Grindey et al. |
| 5,472,949 A | 12/1995 | Arasaki et al. |
| 5,476,932 A | 12/1995 | Brinkman et al. |
| 5,635,517 A | 6/1997 | Muller et al. |
| 5,661,136 A | 8/1997 | Montgomery et al. |
| 5,714,350 A | 2/1998 | Co et al. |
| 5,723,147 A | 3/1998 | Kim et al. |
| 5,780,454 A | 7/1998 | Adams et al. |
| 5,939,098 A | 8/1999 | Reidenberg et al. |
| 6,045,501 A | 4/2000 | Elsayed et al. |
| 6,271,245 B1 | 8/2001 | Jackson et al. |
| 6,281,230 B1 | 8/2001 | Muller et al. |
| 6,315,720 B1 | 11/2001 | Williams et al. |
| 6,316,435 B2 | 11/2001 | Byrd et al. |
| 6,350,861 B1 | 2/2002 | Co et al. |
| 6,555,554 B2 | 4/2003 | Muller et al. |
| 6,561,976 B2 | 5/2003 | Elsayed et al. |
| 6,561,977 B2 | 5/2003 | Williams et al. |
| 6,713,446 B2 | 3/2004 | Gupta et al. |
| 6,755,784 B2 | 6/2004 | Williams et al. |
| 6,849,616 B1 | 2/2005 | Kopreski et al. |
| 6,908,432 B2 | 6/2005 | Elsayed et al. |
| 6,958,319 B2 | 10/2005 | Gupta et al. |
| 7,119,106 B2 | 10/2006 | Muller et al. |
| 7,189,740 B2 | 3/2007 | Zeldis |
| 7,465,800 B2 | 12/2008 | Jaworsky et al. |
| 7,468,363 B2 | 12/2008 | Zeldis |
| 7,507,828 B2 | 3/2009 | Kozikowski et al. |
| 7,507,858 B2 | 3/2009 | Belvedere et al. |
| 7,727,968 B2 | 6/2010 | Feingold et al. |
| 7,772,209 B2 | 8/2010 | Niyikiza |
| 7,842,835 B2 | 11/2010 | Kozikowski et al. |
| 7,855,217 B2 | 12/2010 | Jaworsky et al. |
| 7,943,743 B2 | 5/2011 | Korman et al. |
| 7,968,569 B2 | 6/2011 | Zeldis |
| 8,008,449 B2 | 8/2011 | Korman et al. |
| 8,067,600 B2 | 11/2011 | Kozikowski et al. |

(Continued)

FOREIGN PATENT DOCUMENTS

| | | |
|---|---|---|
| CA | 2977996 A1 | 9/2016 |
| CN | 105524043 A | 4/2016 |

(Continued)

OTHER PUBLICATIONS

International Search Report dated Jun. 4, 2018 for International Patent Application No. PCT/US2018012971, 5 pages.
Written Opinion dated Jun. 4, 2018 for International Patent Application No. PCT/US2018012971, 5 pages.
Gennaro et al., Remington: The Science and Practice of Pharmacy, 20th edition, Part 5, Pharmaceutical Manufacturing, pp. 691, 902-904, 916, 919-920, 923, 926-930, 939-940, 946-949, 1004-1006, 1008, 1011-1015. (2000).
Fleisher et al., Improved oral drug delivery: solubility limitations overcome by the use of prodrugs, Advanced Drug Delivery Reviews, 1996, 19, 115.

(Continued)

*Primary Examiner* — John M Mauro
(74) *Attorney, Agent, or Firm* — Morgan, Lewis & Bockius LLP

(57) ABSTRACT

Selective HDAC inhibitors, and pharmaceutical compositions that include the same, are described herein for the treatment of cancer, immunological diseases, inflammatory diseases, and neurological diseases.

20 Claims, 11 Drawing Sheets

Specification includes a Sequence Listing.

(56) References Cited

U.S. PATENT DOCUMENTS

| | | |
|---|---|---|
| 8,168,757 B2 | 5/2012 | Finnefrock et al. |
| 8,188,067 B2 | 5/2012 | Lerner et al. |
| 8,204,763 B2 | 6/2012 | Elsayed et al. |
| 8,217,149 B2 | 7/2012 | Irving et al. |
| 8,222,451 B2 | 7/2012 | Kozikowski et al. |
| 8,287,856 B2 | 10/2012 | Li et al. |
| 8,288,415 B2 | 10/2012 | Muller et al. |
| 8,315,886 B2 | 11/2012 | Williams et al. |
| 8,354,509 B2 | 1/2013 | Carven et al. |
| 8,404,717 B2 | 3/2013 | Zeldis |
| 8,410,131 B2 | 4/2013 | Lane et al. |
| 8,530,498 B1 | 9/2013 | Zeldis |
| 8,580,247 B2 | 11/2013 | Li et al. |
| 8,589,188 B2 | 11/2013 | Elsayed et al. |
| 8,626,531 B2 | 1/2014 | Williams et al. |
| 8,648,095 B2 | 2/2014 | Zeldis |
| 8,653,278 B2 | 2/2014 | Kozikowski et al. |
| 8,686,119 B2 | 4/2014 | Rotem-Yehudar et al. |
| 8,735,553 B1 | 5/2014 | Li et al. |
| 8,741,929 B2 | 6/2014 | Zeldis |
| 8,748,463 B2 | 6/2014 | Kozikowski et al. |
| 8,779,108 B2 | 7/2014 | Queva et al. |
| 8,822,438 B2 | 9/2014 | Auerbach et al. |
| 8,907,053 B2 | 12/2014 | Sasikumar et al. |
| 9,044,442 B2 | 6/2015 | Sasikumar et al. |
| 9,056,120 B2 | 6/2015 | Zeldis |
| 9,096,642 B2 | 8/2015 | Sasikumar et al. |
| 9,101,621 B2 | 8/2015 | Zeldis |
| 9,101,622 B2 | 8/2015 | Zeldis |
| 9,809,539 B2 | 11/2017 | Grindrod et al. |
| 2004/0110704 A1 | 6/2004 | Yamane et al. |
| 2005/0014839 A1 | 1/2005 | Kozikowski et al. |
| 2005/0032831 A1 | 2/2005 | Kozikowski et al. |
| 2009/0028857 A1 | 1/2009 | Li et al. |
| 2009/0217401 A1 | 8/2009 | Korman et al. |
| 2010/0203056 A1 | 8/2010 | Irving et al. |
| 2010/0266617 A1 | 10/2010 | Carven et al. |
| 2010/0285013 A1 | 11/2010 | Li et al. |
| 2011/0008369 A1 | 1/2011 | Finnefrock et al. |
| 2013/0022600 A1 | 1/2013 | Li et al. |
| 2013/0034559 A1 | 2/2013 | Queva et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0108651 A1 | 5/2013 | Carven et al. |
| 2013/0109843 A1 | 5/2013 | Carven et al. |
| 2013/0133091 A1 | 5/2013 | Korman et al. |
| 2014/0065135 A1 | 3/2014 | Irving et al. |
| 2014/0294898 A1 | 10/2014 | Miller et al. |
| 2014/0341917 A1 | 11/2014 | Nastri et al. |
| 2015/0073024 A1 | 3/2015 | Sasikumar et al. |
| 2015/0073042 A1 | 3/2015 | Sasikumar et al. |
| 2015/0087581 A1 | 3/2015 | Sasikumar et al. |
| 2015/0125491 A1 | 5/2015 | Sasikumar et al. |
| 2016/0257649 A1 | 9/2016 | Grindrod et al. |
| 2016/0347732 A1 | 12/2016 | Breslow et al. |
| 2018/0044292 A1 | 2/2018 | Grindrod et al. |
| 2018/0057456 A1 | 3/2018 | Grindrod et al. |

FOREIGN PATENT DOCUMENTS

| | | |
|---|---|---|
| EP | 0154316 B1 | 9/1989 |
| EP | 0401384 B1 | 3/1996 |
| EP | 0404097 B1 | 9/1996 |
| EP | 1176195 B1 | 5/2013 |
| WO | 9311161 A1 | 6/1993 |
| WO | 1999054342 A1 | 10/1999 |
| WO | 2002/026696 A1 | 4/2002 |
| WO | 2003035835 A2 | 5/2003 |
| WO | 2006121168 A1 | 11/2006 |
| WO | 2008/019025 A2 | 2/2008 |
| WO | 2008/117935 A1 | 10/2008 |
| WO | 2008156712 A1 | 12/2008 |
| WO | 2011017448 A1 | 2/2011 |
| WO | 2011/106650 A2 | 9/2011 |
| WO | 2013/013113 A2 | 1/2013 |
| WO | 2013013113 A2 | 1/2013 |
| WO | 2014/090398 A1 | 6/2014 |
| WO | 2014/178606 A1 | 11/2014 |
| WO | 2015033301 A1 | 3/2015 |
| WO | 2015036927 A1 | 3/2015 |
| WO | 2015044900 A1 | 4/2015 |
| WO | 2016044690 A1 | 3/2016 |
| WO | 2016105518 A1 | 6/2016 |
| WO | 2016/141122 A1 | 9/2016 |
| WO | 2016141122 A1 | 11/2017 |
| WO | 2018129533 A1 | 7/2018 |

OTHER PUBLICATIONS

Abraham et al., Burger's Medicinal Chemistry, Drug Discovery, and Development, vols. 1-8, 7th Ed., John Willey & Sons, 2010, ISBN:978-0-470-27815-4, Abstract, 1 page.

Li et al. eds., Drug-like Properties: Concepts, Structure Design and Methods from ADME to Toxicity Optimization, Academic Press, San Diego, 2008, Chapter 39, Prodrug, pp. 426-438.

Li et al. eds., Drug-like Properties: Concepts, Structure Design and Methods from ADME to Toxicity Optimization, Academic Press, San Diego, 2008, Chapters 20-21, pp. 242-253.

Greene et al. Eds., Protective Groups in Organic Synthesis, 4th Ed., John Wiley & Sons, Hoboken, NJ, 2006, ISBN:0-471-69754-0, Table of contents, 4 pages.

Thomas et al., Immunotherapy for non-small-cell lung cancer, Exp. Opin. Biol. Ther., 2014, 14, 1061-1064.

Berger, et al., Phase I Safety and Pharmacokinetic Study of CT-011, a Humanized Antibody Interactingwith PD-1, in Patients with Advanced HematologicMalignancies, Clin. Cancer Res. 2008, 14, 3044-51.

E. L. Eliel and S. H. Wilen, Stereochemistry of Organic Compounds, Wiley—Interscience, New York, 1994, Chapter 3, Stereoisomers, pp. 49-68.

Ward et al, Binding activities of a repertoire of single immunoglobulin variable domains secreted from *Escherichia coli*., Nature, 1989, 341, 544-546.

Bird et al., Single Chain Antigen-Binding Proteins, Science 1988, 242, 423-426.

Huston et al, Protein engineering of antibody binding sites: Recovery of specific activity in an anti-digoxin single-chain Fv analogue produced in *Escherichia coli*, Proc. Natl. Acad. Sci. USA 1988, 85. 5879-5883.

Jones et al, Replacing the Complementarity-Determining Regions in a Human Antibody With Those From a Mouse, Nature 1986, 321, 522-525.

Riechmann et al, Reshaping Human Antibodies for Therapy, Nature 1988, 332, 323-329.

Presta, Antibody Engineering, Curr. Op. Struct. Biol. 1992, 2, 593-596.

Holliger et al, "Diabodies": Small bivalent and bispecific antibody fragments, Proc. Natl. Acad. Sci. USA 1993, 90, 6444-6448.

Yamane-Ohnuki, et al., Establishment of FUT8 Knockout Chinese Hamster Ovary Cells: An Ideal Host Cell Line for Producing Completely Defucosylated Antibodies With Enhanced Antibody-Dependent Cellular Cytotoxicity, Biotechnol. Bioeng., 2004, 87, 614-622.

Shields, et al, Lack of Fucose on Human IgG1 N-Linked Oligosaccharide Improves Binding to Human FcRIII and Antibody-dependent Cellular Toxicity, J. Biol. Chem. 2002, 277, 26733-26740.

Umana, et al, Engineered Glycoforms of an Antineuroblastoma IgG1 With Optimized Antibody-Dependent Cellular Cytotoxic Activity, Nat. Biotech. 1999, 17, 176-180.

Tarentino, et al, The Isolation and Structure of the Core Oligosaccharide Sequences of IgM, Biochem. 1975, 14, 5516-5523.

Wang et al, In Vitro Characterization of the Anti-PD-1 Antibody Nivolumab, BMS-936558, and In Vivo Toxicology in Non-Human Primates, Cancer Immunol Res. 2014, 2, 846-56.

Page et al, Immune Modulation in Cancer with Antibodies, Ann. Rev. Med., 2014, 65, 185-202.

(56) References Cited

OTHER PUBLICATIONS

Weber et al, Safety, Efficacy, and Biomarkers of Nivolumab With Vaccine in Ipilimumab-Refractory or -Naive Melanoma, J. Clin. Oncology, 2013, 31, 4311-4318.
Brahmer et al, Survival, Durable Tumor Remission, and Long-Term Safety in Patients With Advanced Melanoma Receiving Nivolumab, J. Clin. Oncol. 2014, 32, 5s (supplement, abstract 8021).
McDermott et al, Durable benefit and the potential for long-term survival with immunotherapy in advanced melanoma, Cancer Treatment Rev., 2014, 40, 1056-64.
Mansfield, et al., Recombinant RFB4 Immunotoxins Exhibit Potent Cytotoxic Activity for CD22-bearing Cells and Tumors, Blood (1997) 90: 2020-2026.
Kreitman, et al., Antibody Fusion Proteins: Anti-CD22 Recombinant Immunotoxin Moxetumomab Pasudotox, Clin Cancer Res. (201 1) 17: 6398-6405).
Anderson eds.,Handbook of Clinical Drug Data,Tenth Edition,McGraw-Hill, 2002, 1164 pages.
Li et al. eds., Drug-like Properties: Concepts, Structure Design and Methods from ADME to Toxicity Optimization, Academic Press, San Diego, 2008, Chapter 1-19, pp. 1-241.
Fuerst, Metastatic Melanoma: Immunotherapy with Pembrolizumab Induces Durable ResponsesOncology,Times, 2014, 36, 35-36.
Robert, et al., Anti-programmed-death-receptor-1 Treatment With Pembrolizumab in Ipilimumab-Refractory Advanced Melanoma: A Randomised Dose-Comparison Cohort of a Phase 1 Trial, Lancet, 2014, 384, 1109-17.
International Search Report for PCT/US16/20573 dated May 20, 2016.
Lin et al., Zhongguo Yaoke Daxue Xuebao, 35 (2), 2004, pp. 106-109.
STN Registry entry for CAS RN 1026059-94-8; entered STN Registry database Jun. 6, 2008, Accessed Sep. 17, 2018.
Database CA [Online] Chemical Abstract Service, Columbus, Ohio, US; retrieved from STN Database accession No. 2005:208892.
Guo Y et al,; Bioorganic & medicinal chemistry 2005, pp. 5424-5434, XP027637896.
Eleni Pontiki et al,; Medicinal Research Reviews 2012, vol. 32, No. 1, ages 1-165, XP055301061.
European Search Report EP Application No. 16759455.5, dated Aug. 28, 2018, (9 pgs.).
Abraham, Robert T. et al., "Guiding ATM to Broken DNA", Science, 308: 510-511 (2005).
Adimoolam, Shanthi et al., "HOAG inhibitor PCI-24781 decreases RAD51 expression and inhibits homologous recombination", PNAS, 104(49): 19482-19487 (2007).
Arundel, Carla M. et al., "Enhancement of Radiation Injury in Human Colon Tumor Cells by the Maturational Agent Sodium Butyrate (NaB)", Radiation Research, 104: 443-448 (1985).
Bakkenist, Christopher J. et al., "DNA damage activates ATM through intermolecular autophosphorylati9on and dimer dissociation", Nature, 421: 499-506 (2003).
Banuelos, Carmen A. et al., Radiosensitization by the Histone Deacetylase Inhibitor PCI-24781, Clin. Cancer Res., 13(22): 6816-6826 (2007).
Barzilai, Ari et al., "ATM deficiency and oxidative stress: a new dimension of defective response to DNA damage", DNA Repair, 1:3-25 (2002).
Blagosklonny, Mikhail V. et al., "Histone Deacetylase Inhibitors All Induce p21 but Differentially Cause Tubulin Acetylation, Mitotic Arrest, and Cytotoxicity", Molecular Cancer Therapeutics, 1: 937-941 (2002).
Camphausen, Kevin et al., "Enhancement of in vitro and in vivo tumor cell radioisensitivity by valproic acid", Int. J. Cancer, 114: 380-386 (2005).
Camphausen, Kevin et al., "Enhancement of Xenograft Tumor Radiosensitivity by the Histone Deacetylase Inhibitor MS-275 and Correlation with Histone Hyperacetylation", Clinical Cancer Research, 10: 6066-6071 (2004).
Camphausen. Kevin et al.. "Inhibition of Histone Deacetylation: A Strategy for Tumor Radiosensitization", J_ Clin. Oncol, 25: 4051-4056 (2007).
Cerna, David et al., "Histone Deacetylation as a Target for Radiosensitization", Current Topics in Developmental Biology, 73: 173-204 (2006).
Chang, Brian K. et al., "Stereotactic Body Radiation Therapy", American Journal of Clinical Oncology, 30(6): 637-644 (2007).
Chen, Bin et al., "Chemistry and biology of mercaptoacetamides as novel histone deacetylase inhibitors", Bioorganic & Medicinal Chemistry Letters, 15: 1389-1392 (2005).
Chinnaiyan, Prakash et al., "Modulation of Radiation Response by Histone Deacetylase Inhibition", Int. J_ Radiation Oncology Biol. Phys., 62(1): 223-229 (2005).
Chung, Yih-Lin et al., "Antitumor histone deacetylase inhibitors suppress cutaneous radiation syndrome: Implications for increasing therapeutic gain in cancer radiotherapy", Molecular Cancer Therapeutics, 3(3): 317-325 (2004).
Dai, Yujia et al., "Indole Amide Hydroxamic Acids as Potent Inhibitors of Histone Deacetylases", Bioorganic & Medicinal Chemistry Letters, 13: 1897-1901 (2003).
Fakiris, Achilles J_ et al., "Stereotactic Body Radiation Therapy for Early-Stage Non-Small-Cell Lung Carcinoma: Four-Year Results of a Prospective Phase II Study", Int. J_ Radiation Oncology Biol. Phys., 75(3): 677-682 (2009).
Fan, Saijun et al., "DIM (3,3'-diindolylmethane) confers protection against ionizing radiation by a unique mechanism", PNAS, 110(46): 18650-18655 (2013).
Fraczek, Joanna et al., "Screening of amide analogues of Trichostatin A in cultures of primary rat hepatocytes: search for potent and safe HDAC inhibitors", Invest. New Drugs, 27: 338-346 (2009).
Gleave, Martin E. et al., "Butyrate Analogue, Isobutyramide, Inhibits Tumor Growth and Time to Androgen-Independent Progression in the Human Prostate LNCaP Tumor Model", Journal of Cellular Biochemistry, 69: 271-281 (1998).
Gottlicher, Martin et al., "Valproic acid defines a novel class of HDAC inhibitors inducing differentiation of transformed cells", The EMBO Journal, 20(24); 6969-6978 (2001).
Grunstein, Michael, "Histone acetylation in chromatin structure and transcription", Nature, 389: 349-352 (1997).
Guo, Zhi et al., "ATM Activation by Oxidative Stress", Science, 330: 517-521 (2010).
Ito, Akihiro et al., "MDM2-HDAC1-mediated deacetylation of p53 is required for its degradation", The EMBO Journal, 21 (22): 6236-6245 (2002).
Johnstone, Ricky W. et al., "Histone-Deacetylase Inhibitors: Novel Drugs for the Treatment of Cancer", Nature Reviews, 1: 287-299 (2002).
Ju, Rong et al., "Histone Deacetylase Inhibitors Activate p21 WAF1 Expression via ATM", Cancer Research, 63: 2891-2897 (2003).
Jung, Mira et al., "Rational Design and Development of Radiation-Sensitizing Histone Deacetylase Inhibitors", Chemistry & Biodiversity, 2: 1452-1461 (2005).
Kao, Gary D. et al., "Histone deacetylase 4 interacts with 53BP1 to mediate the DNA damage response", The Journal of Cell Biology, 160(7): 1017-1027 (2003).
Karagiannis. Tom C. et al., "The Epigenetic Modifier, Valproic Acid, Enhances Radiation Sensitivity", Epigenetics, 1(3): 131-137 (2006).
Karagiannis, TC et al., "Modulation of cellular radiation response by histone deacetylase inhibitors", Oncogene, 25: 3885-3893 (2006).
Kelly, Wm. Kevin et al., "Phase I Clinical Trial of Histone Deacetylase Inhibitor: Suberoylanilide Hydroxamic Acid Administered Intravenously", Clinical Cancer Research, 9: 3578-3588 (2003).
Kim, Gun D. et al., "Sensing of Ionizing Radiation-Induced DNA Damage by ATM through Interaction with Histone Deacetylase", The Journal of Biological Chemistry, 274(44): 31127-31130 (1999).
Kim, In Ah et al., "Histone Deacetylase Inhibitor-Mediated Radiosensitization of Human Cancer Cells: Class Differences and the Potential Influence of p53", Clin. Cancer Res., 12(3): 940-949 (2006).

(56) References Cited

OTHER PUBLICATIONS

Kim, Jin Ho et al., "Susceptibility and Radiosensitization of Human Glioblastoma Cells to Trichostatin A, A Histone Deacetylase Inhibitor", Int. J. Radiation Oncology Biol. Phys., 59(4): 1174-1180 (2004).

Kouzarides, Tony, "Histone acetylases and deacetylases in cell proliferation", Current Opinion in Genetics & Development, 9:40-48 (1999).

Kruger, Antje et al., "ATM Is a Redox Sensor Linking Genome Stability and Carbon Metabolism", Science Signaling, 4: 167(2011).

Kurdistani, Siavash K. et al., "Histone Acetylation and Deacetylation in Yeast", Nature, 4: 276-284 (2003).

Gregoretti, Ivan V. et al., "Molecular Evolution of the Histone Deacetylase Family: Functional Implications of Phylogenetic Analysis", J. Mol. Biol., 338: 17-31 (2004).

Lagger, Gerda et al., "Essential function of histone deacetylase 1 in proliferation control and CDK inhibitor repression", The EMBO Journal, 21 (11 ): 2672-2681 (2002).

Marks, Paul A. et al., "Histone Deacetylase Inhibitors: Inducers of Differentiation or Apoptosis of Transformed Cells", Journal of the National Cancer Institute, 92(15): 1210-1216 (2000).

Marks, Paul A. et al., "Histone Deacetylases and Cancer: Causes and Therapies", Nature, 1: 194-202 (2001).

Melchior, Sebastian et al., "Effects of phenylbutyrate on proliferation and apoptosis in human prostate cancer cells in vitro and in vivo", International Journal of Oncology, 14: 501-508 (1999).

Munshi, Anupama et al., "Histone Deacetylase Inhibitors Radiosensitize Human Melanoma Cells by Suppressing DNA Repair Activity", Clin. Cancer Res., 11 (13): 4912-4922 (2005).

Naryzhny, Stanislav N. et al., "The Post-translational Modifications of Proliferating Cell Nuclear Antigen", The Journal of Biological Chemistry, 279(19): 20194-20199 (2004).

Nome, Ragnhild V. et al., "Cell cycle checkpoint signaling involved in histone deacetylase inhibition and radiation-induced cell death", Mol. Cancer Ther., 4(8): 1231-1238 (2005).

Patnaik, Arnita et al., "A Phase I Study of Pivaloyloxymethyl Butyrate, a Prodrug of the Differentiating Agent Butyric Acid, in Patients with Advanced Solid Malignancies", Clinical Cancer Res., 8: 2142-2148 (2002).

Pauer, Lynn R. et al., "Phase I Study of Oral CI-994 in Combination with Carboplatin and Paclitaxel in the Treatment of Patients with Advanced Solid Tumors", Cancer Investigation, 22(6): 886-896 (2004).

Perrine, Susan P. et al., "A Short-Term Trial of Butyrate to Stimulate Fetal-Globin-Gene Expression in the B-Globin Disorders", The New England Journal of Medicine, 328(2): 81-86 (1993).

Peterson, Craig L. et al., "Cellular machineries for chromosomal DNA repair", Genes & Development, 18: 602-616 (2004).

Reliene, Ramune et al., "Antioxidants Suppress Lymphoma and Increase Longevity in Alm-Deficient Mice", The Journal of Nutrition, 137: 229S-232S (2007).

Richon, Victoria M. et al., "A class of hybrid polar inducers of transformed cell differentiation inhibits histone deacetylases", Proc. Natl. Acad. Sci. USA, 95: 3003-3007 (1998).

Rosato, Roberto R. et al., "HOAG inhibitors activate NF-kB in human leukemia cells through an ATM/nemo-related pathway", J. Biol. Chem. (2010).

Ruijter, Annemieke J.M. et al., "Histone deacetylases (HDACs): characterization of the classical HOAG family", Biochem. J., 370P: 737-749 (2003).

Ryan, Qin C. et al., "Phase I and Pharmacokinetic Study of MS-275, a Histone Deacetylase Inhibitor, in Patients with Advanced and Refractory Solid Tumors or Lymphoma", J. Clin. Oncol., 23: 3912-3922 (2005).

Shiloh, Yosef, "ATM and Related Protein Kinases: Safeguarding Genome Integrity", Nature Reviews, 3: 155-168 (2003).

Struhl, Kevin et al., "The TAFs in the HAT", Cell, 94: 1-4 (1998).

Struhl, Kevin, "Histone acetylation and transcriptional regulatory mechanisms", Genes & Development, 12: 599-606 (1998).

Stoilov, L. et al., "Inhibition of repair of X-ray-induced DNA double-strand breaks in human lymphocytes exposed to sodium butyrate", Int. J. Radial. Biol., 76(11) 1485-1491 (2000).

Tauchi. Hiroshi et al., "Nijmegen breakage syndrome gene, NBS1, and molecular links to factors for genome stability", Oncogene, 21: 8967-8980 (2002).

Uziel, Tamar et al., "Requirement of the MRN complex for ATM activation by DNA damage", The EMBO Journal, 22(20): 5612-5621 (2003).

Vrana, JA et al., "Induction of apoptosis in U937 human leukemia cells by suberoylanilide hydroxamic acid (SAHA) proceeds through pathways that are regulated by Bcl-2/Bcl-XL, c-Jun and p21 CIP1, but independent of p53", Oncogene, 18: 7016-7025 (1999).

Watters, Dianne J. et al., Oxidative stress in ataxia telangiectasia, Redox Report, 8(1): 23-29 (2003).

Wolffe, Alan P. et al., "Review: Chromatin Structural Features and Targets That Regulate Transcription", Journal of Structural Biology, 129: 102-122 (2000).

Yamamoto, Shunsaku et al., "Suberoylanilide Hydroxamic Acid (SAHA) Induces Apoptosis or Autophagy-associated Cell Death in Chondrosarcoma Cell Lines", Anticancer Research, 28: 1585-1592 (2008).

Zhang, Yin et al., "Attenuated DNA Damage Repair by Trichostatin A through BRCA1 Suppression", Radiation Research, 168: 115-124 (2007).

Zhang, Yin et al., "Enhancement of Radiation Sensitivity of Human Squamous Carcinoma Cells by Histone Deacetylase inhibitors", Radiation Research, 161: 667-67 4 (2004).

Zhou, Bin-Bing S. et al., "The DNA damage response: putting checkpoints in perspective", Nature, 408: 433-439 (2000).

Arundel, Carla M. et al., "Effects of Nucleoside Analogs and Sodium Butyrate on Recovery from Potentially Lethal X Ray Damage in Human Colon Tumor Cells", Int. J. Radiation Oncology Biol. Biol. Phys., 13: 593-601 (1987).

Varshochi, Rana et al., "ICI182,780 Induces p21 Waf1 Gene Transcription through Releasing Histone Deacetylase 1 and Estrogen Receptor a from Sp1 Sites to Induce Cell Cycle Arrest in MCF-7 Breast Cancer Cell Line", The Journal of Biological Chemistry, 280(5): 3185-3196 (2005).

Furumai et al., FK228 (Drpsipeptide) as a natural prodrug that inhibits Class I histone Deacetylases, Cancer Research, 2002, vol. 62, 4916-49-21.

Geng et al., Histone Deacetylase (HDAC) inhibitor LBH589 Increases Duration of gama-H2AX Foci and Confines HDAC4 to the Cytoplasm in Irradiated Non-Small Cell Lung Cancer, Cancer Res., 2006, vol. 66, pp. 11298-11304.

European Search Opinion for EP Application No. 16759455.5, dated Sep. 5, 2017 (14 pgs.).

Noopur Raje et al: The New Drug Partner for Combination Therapy in Multiple Myeloma (MM): Phase 1 Development of ACY-1215, A Selective Histone Deactylase (HDAC) 6 Inhibitor Alone and in Combination with Bortezomib or Lenalidomide , EHA 2013 Congress Abstract P765 (Poster Presentation), Jun. 20, 2013.

Extended European Search Report dated Aug. 6, 2020 for European Application No. 18736068.0, 7 pages.

European Search Report issued for EP 22151199 dated Jul. 11, 2022, 10 pages.

Noopur Raje et al: "The New Drug Partner for Combination Therapy in Multiple Myeloma (MM): Phase 1 Development of ACY-1215, A Selective Histone Deactylase (HDAC) 6 Inhibitor Alone and in Combination with Bortezomib or Lenalidomide", EHA 2013 Congress Abstract P765 (Poster Presentation), Jun. 20, 2013 (Jun. 20, 2013), XP055361871, Retrieved from the Internet: URL:http://www.myelomabeacon.com/docs/eha2 013/posters/Raje-ACY-1215-Bortezomib-Lenal idomide.pdf.

Andrew J Yee et al: "Ricolinostat plus lenalidomide, and dexamethasone in relapsed or refractory multiple myeloma: a multicentre phase Ib trial", The Lancet Oncology, vol. 17, No. 11, Nov. 1, 2016 (Nov. 1, 2016), pp. 1569-1578.

| Compound | IC$_{50}$ [μM] HDAC Activity Inhibition | | | | |
|---|---|---|---|---|---|
| | Pan-HDAC | HDAC1 | HDAC3 | HDAC6 | Ratio (HDAC1:HDAC6) |
| SP-2-59 | 13 μM | 5 μM | 5 μM | 0.060 μM | 83-fold |
| SP-2-93 | 0.430 μM | 1.545 μM | 3.069 μM | 0.006 μM | 258-fold |
| Lenalidomide | n.a. | n.a. | n.a. | n.a. | - |
| Glutarimide | n.a. | n.a. | n.a. | n.a. | - |

Note: n.a. = no activity at 25 μM as a maximum dosage tested

| HDAC | 1 | 2 | 3 | 4 | 5 | 6 | 7 | 8 | 9 | 10 | 11 |
|---|---|---|---|---|---|---|---|---|---|---|---|
| | 1.89 µM | 1.54 µM | 136 nM | 3.07 µM | | 60 nM | | | | | |
| | 46.8 nM | | 25.5 nM | N/A | N/A | 15.3 nM | N/A | N/A | N/A | 37.7 nM | N/A |
| | N/A | N/A | N/A | 2.1 µM | 1.8 µM | N/A | 1.0 µM | 471 nM | 2.9 µM | N/A | 16.6 µM |

FIG. 18

SELECTIVE HISTONE DEACETYLASE INHIBITORS FOR THE TREATMENT OF HUMAN DISEASE

CROSS-REFERENCE TO RELATED APPLICATIONS

This application is a continuation of U.S. application Ser. No. 16/476,006 filed Jul. 3, 2019, which is the U.S. National Stage of International Patent Application No. PCT/US2018/012971, filed Jan. 9, 2018, which claims the benefit of U.S. Provisional Application No. 62/444,003, filed Jan. 9, 2017, the entirety of which is incorporated herein by reference.

FIELD OF THE INVENTION

The invention relates generally to compounds that inhibit histone deacetylase (HDAC) protein and more particularly, but not exclusively, to compounds that specifically inhibit HDAC6 and pharmaceutical compositions and methods of treating diseases that may beneficially utilize such compounds.

BACKGROUND OF THE INVENTION

A variety of diseases are known in the field to elude common treatment methods. For example, certain diseases and disorders that implicate histone deacetylase (HDAC) proteins as pharmacological targets have continued to evade known therapeutics and treatment methodologies. Pan-HDAC inhibitors have multiple toxicities due to off-target effects. Molecules that may specifically target certain HDAC proteins may have a greater potential for treating disease with decreased toxicity.

Accordingly, a need exists in the field for compounds, compositions, and methods for treating such elusive diseases and disorders, including certain cancers, inflammatory diseases, immunological diseases, and neurological diseases, by specifically inhibiting HDAC6.

SUMMARY OF THE INVENTION

The invention meets the needs in the field by providing specific inhibitors of HDAC proteins and may be used in the treatment of certain cancers, neurological disorders, and immunological disorders. Indeed, the compounds of the invention may be used in pharmaceutical compositions and methods of treatment in combating these and other related diseases. In some embodiments, the compounds invention includes specific inhibitors of HDAC6.

In one aspect, the invention includes a compound of formula (Ia) or (Ib):

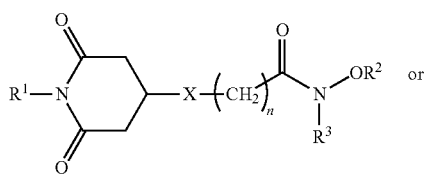

(Ia)

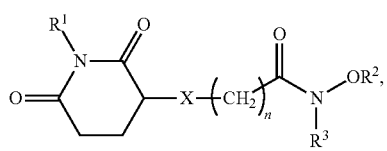

(Ib)

wherein $R^1$ may be a substituent selected from the group consisting of H and optionally substituted alkyl and aryl;

$R^2$ may be a substituent selected from the group consisting of H and optionally substituted alkyl and aryl;

$R^3$ may be a substituent selected from the group consisting of H and optionally substituted alkyl and aryl;

X may be a substituent selected from the group consisting of —N($R^4$)C(O)—, —C(O)N($R^4$)—, —S(O)$_2$N($R^4$)—, —N($R^4$)S(O)$_2$—,

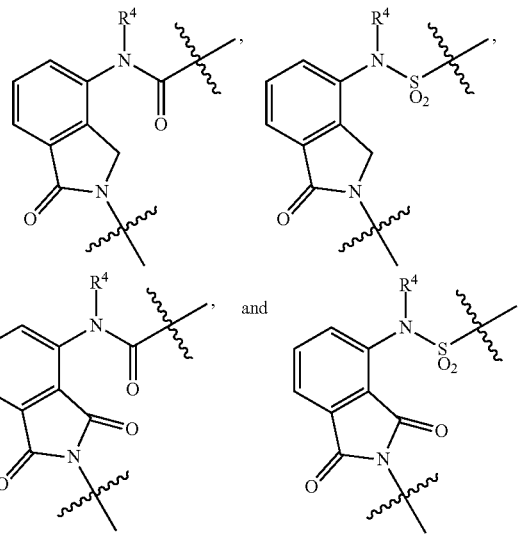

where $R^4$ may be a substituent selected from the group consisting of H and optionally substituted alkyl and aryl; n may be an integer from 5 to 7; or a pharmaceutically acceptable salt, solvate, hydrate, cocrystal, or prodrug thereof.

In some embodiments of formula (Ia) or (Ib), n may be 6.

In some embodiments, the invention includes a compound formula (II):

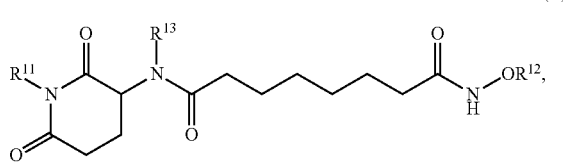

(II)

wherein $R^{11}$ may be a substituent selected from the group consisting of H and optionally substituted alkyl and aryl;

$R^{12}$ may be a substituent selected from the group consisting of H and optionally substituted alkyl and aryl;

$R^{13}$ may be a substituent selected from the group consisting of H and optionally substituted alkyl and aryl; or a pharmaceutically acceptable salt, solvate, hydrate, cocrystal, or prodrug thereof. In some embodiments, the compounds of formula (Ib) include the compounds of formula (II).

In some embodiments, the compound of formula (Ib) and/or formula (II) may be $N^1$-(2,6-dioxopiperidin-3-yl)-$N^8$-hydroxyoctanediamide (i.e., SP-2-59),

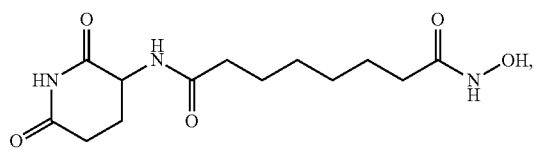 [SMILES: O=C(CCCCCCC(=O)NC1CCC(=O)NC1=O)NO]

or a pharmaceutically acceptable salt, solvate, hydrate, cocrystal, or prodrug thereof.

In some embodiments, the invention may include a compound of formula (III):

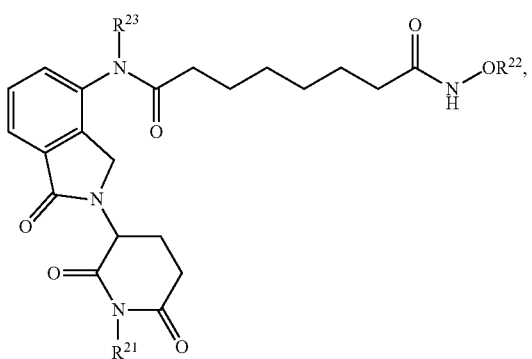

wherein $R^{21}$ may be a substituent selected from the group consisting of H and optionally substituted alkyl and aryl;

$R^{22}$ may be a substituent selected from the group consisting of H and optionally substituted alkyl and aryl;

$R^{23}$ may be a substituent selected from the group consisting of H and optionally substituted alkyl and aryl; or a pharmaceutically acceptable salt, solvate, hydrate, cocrystal, or prodrug thereof.

In some embodiments, the compound of formula (Ia) and/or formula (III) may be $N^1$-(2-(2,6-dioxopiperidin-3-yl)-1-oxoisoindolin-4-yl)-$N^8$-hydroxyoctanediamide (i.e., SP-2-93),

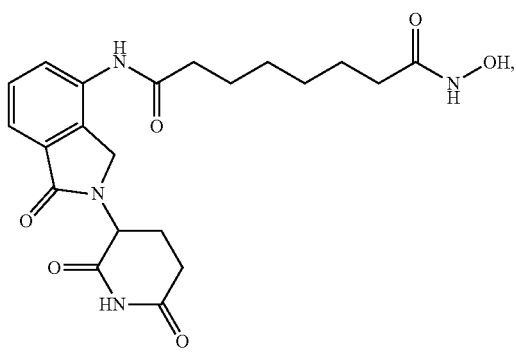 [SMILES: O=C(CCCCCCC(=O)Nc1cccc2c1CN(C1CCC(=O)NC1=O)C2=O)NO]

or a pharmaceutically acceptable salt, solvate, hydrate, cocrystal, or prodrug thereof.

In another aspect, the invention includes a pharmaceutical composition or formulation that may include an HDAC inhibitor, such as selective HDAC inhibitor (e.g., selective inhibitor of HDAC6), in an amount effective to treat a disease alleviated by inhibiting HDAC protein in a patient in need thereof, and a physiologically compatible carrier medium.

In some embodiments, the pharmaceutical composition may include one or more compounds of formula Ia, Ib, II, and/or III, or a pharmaceutically acceptable salt, solvate, hydrate, cocrystal, or prodrug thereof.

In some embodiments, the pharmaceutical composition may include

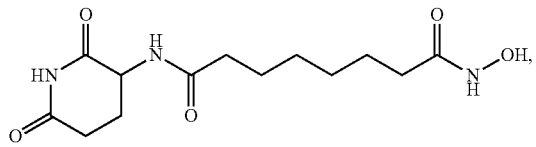 [SMILES: O=C(CCCCCCC(=O)NC1CCC(=O)NC1=O)NO]

or a pharmaceutically acceptable salt, solvate, hydrate, cocrystal, or prodrug thereof.

In some embodiments, the pharmaceutical composition may include

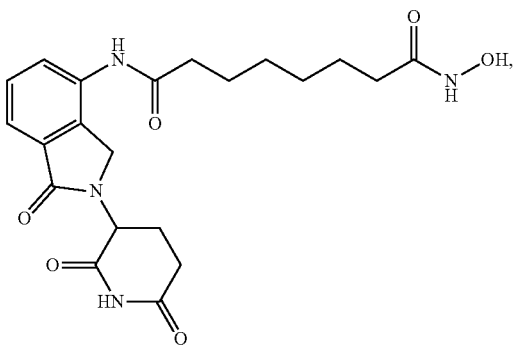 [SMILES: O=C(CCCCCCC(=O)Nc1cccc2c1CN(C1CCC(=O)NC1=O)C2=O)NO]

or a pharmaceutically acceptable salt, solvate, hydrate, cocrystal, or prodrug thereof.

In some embodiments, the pharmaceutical composition may include a selective HDAC6 inhibitor.

In another aspect, the invention may include a method of treating a disease alleveiated by inhibiting HDAC protein, or optionally selectively inhibiting HDAC6 protein, in a patient in need thereof, wherein the treatment comprises administering a therapeutically effective amount of one or more HDAC inhibitors that may include one or more compounds of formula Ia, Ib, II, and/or III, or a pharmaceutically acceptable salt, solvate, hydrate, cocrystal, or prodrug thereof.

In some embodiments, the one or more HDAC inhibitors include a selective HDAC6 inhibitor.

In some embodiments, the one or more HDAC inhibitors may be administered in dosage unit form. In some embodiments, the dosage unit may include a physiologically compatible carrier medium.

In some embodiments, the one or more HDAC inhibitors may include

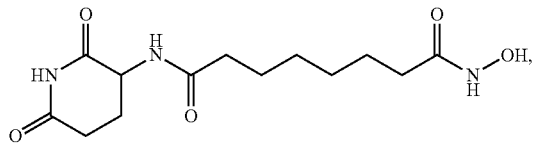 [SMILES: O=C(CCCCCCC(=O)NC1CCC(=O)NC1=O)NO]

or a pharmaceutically acceptable salt, solvate, hydrate, cocrystal, or prodrug thereof.

In some embodiments, the one or more HDAC inhibitors may include

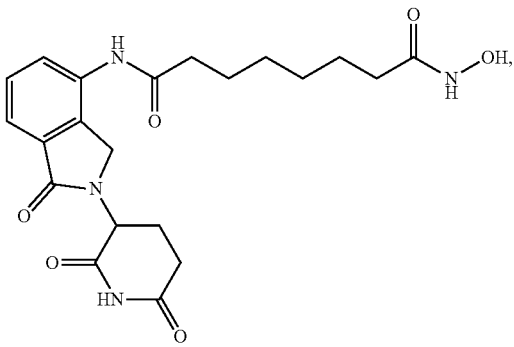 [SMILES: O=C(CCCCCCC(=O)Nc1cccc2c1CN(C1CCC(=O)NC1=O)C2=O)NO]

or a pharmaceutically acceptable salt, solvate, hydrate, cocrystal, or prodrug thereof.

In some embodiments, the disease alleviated by inhibiting HDAC protein may be cancer, an immunological disease, an inflammatory disease, or a neurological disease.

In some embodiments, the cancer alleviated by inhibiting HDAC activity, and optionally selectively inhibiting HDAC6 activity, may be selected from the group consisting of acoustic neuroma, adenocarcinoma, angiosarcoma, astrocytoma, basal cell carcinoma, bile duct carcinoma, bladder carcinoma, brain cancer, breast cancer, brochogenic carcinoma, cervical cancer, chordoma, choriocarcinoma, colon cancer, colorectal cancer, craniopharygioma, cystadenocarcinoma, embryonal carcinoma, endotheliocarconima, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebacaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, and Waldenstrom's macroglobulinemia. In some embodiments the cancer may be an HPV16 positive (+) cancer. In some embodiments, the HPV16 and HPV18 positive (+) cancer may include one or more of cervical cancer and head and neck cancer. In some embodiments, when the disease treated by the methods of the invention is cancer, the cancer may be selected from those cancers listed herein.

In some embodiments, the immunological disease alleviated by inhibiting HDAC activity, and optionally selectively inhibiting HDAC6 activity, may be selected from the group consisting of celiac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, rheumatoid arthritis (RA), polymyositis, ulcerative colitis, Crohn's disease, autoimmune carditis, Wegener's granulomatosis, autoimmune hemolytic anemia, polyarteritis nodosa, psoriasis, vitiligo, epidermolysis bullosa, scleroderma, alopecia areata, epidermolysis bullosa acquisita, bullous pemphigoid, pemphigus foliaceous, and pemphigus vulgaris.

In some embodiments, the neurological disease alleviated by inhibiting HDAC activity, and optionally selectively inhibiting HDAC6 activity, may be selected from the group consisting of stroke, Huntington's disease, spinal muscular atrophy (SMA), Parkinson's disease, Alzheimer's, Multiple Sclerosis, and Amyotrophic Lateral Sclerosis (ALS).

In some embodiments, the pharmaceutical compositions may include an additional therapeutic agent. In certain embodiments, the additional therapeutic agents may include one or more of a chemotherapeutic and an immunotherapeutic agent.

In some embodiments, the chemotherapeutic agent may include one or more of bortezomib (Velcade®), lenalidomide (Revlimid®), temozolomide, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, Thioguanine, daunorubicin; doxorubicin, epirubicin, idaurubicin, topotecan, irinotecan, etoposide, teniposide, mitoxantrone, Vinblastine, vincristine, vinorelbine, estramustine, paclitaxel, dexamethasone, and docetaxel.

In some embodiments, the immunotherapeutic agent may include a one or more of a PD-1 inhibitor and a PD-L1 inhibitor, wherein the PD-1 and PD-L1 inhibitor may be selected from the group consisting of nivolumab, pembrolizumab, pidilizumab, durvalumab, atezolizumab, avelumab, or any fragment, derivative, conjugate, variant, radioisotope-labeled complex, or biosimilar thereof.

In some embodiments, the immunotherapeutic agent may include one or more of rituximab, trastuzumab, ibritumomab, tositumomab, cetuximab, bevacizumab, gemtuzumab, alemtuzumab, and BL22 or any fragment, derivative, conjugate, variant, radioisotope-labeled complex, or biosimilar thereof.

In another embodiment, the method of the invention may be a second or third line method of treatment for the patient and administration of the compound occurs after performance of a first or second therapy on the patient that failed to treat the disease.

Accordingly, as briefly described herein, this disclosure includes compounds, compositions, and methods of treatment that provide treatment solutions to answer the needs in the field.

BRIEF DESCRIPTION OF THE DRAWINGS

The foregoing summary and the following detailed description of the exemplary embodiments as described herein may be further understood when read in conjunction with the appended drawings, in which:

FIG. 18 illustrates the results of an in vitro assay comparing the selective inhibitory activity of $N^1$-(2-(2,6-dioxopiperidin-3-yl)-1-oxoisoindolin-4-yl)-$N^8$-hydroxyoctanediamide (i.e., SP-2-93) against Pan HDAC, HDAC1, HDAC3, and HDAC6 proteins. These results were compared to SAHA and TSA and indicate that $N^1$-(2-(2,6-dioxopiperidin-3-yl)-1-oxoisoindolin-4-yl)-$N^8$-hydroxyoctanediamide (i.e., SP-2-93) is highly selective for HDAC 6 as compared to Pan HDAC, HDAC1, and HDAC3 proteins.

DETAILED DESCRIPTION OF THE INVENTION

Figure 1:
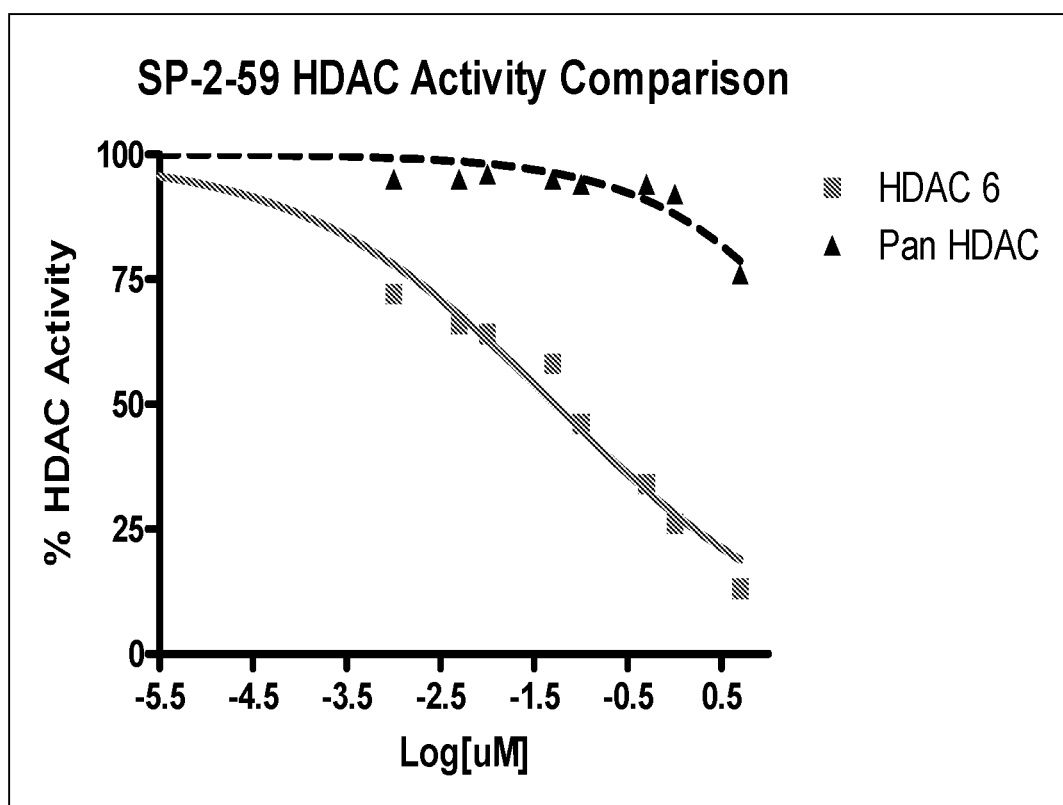
FIG. 1 illustrates the in vitro inhibitory activity of $N^1$-(2,6-dioxopiperidin-3-yl)-$N^8$-hydroxyoctanediamide (i.e., SP-2-59) against HDAC6 and pan-HDACs.

Unless defined otherwise, all technical and scientific terms used herein have the same meaning as is commonly understood by one of skill in the art to which this invention belongs. All patents and publications referred to herein are incorporated by reference in their entireties.

Definitions

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The terms "active pharmaceutical ingredient" and "drug" include the HDAC inhibitors, chemotherapeutic agents, and immunotherapeutic agents described herein and, more specifically, include the HDAC inhibitors described by Formulas Ia, Ib, II, and/or III. The terms "active pharmaceutical ingredient" and "drug" may also include those compounds described herein that bind HDAC protein and thereby modulate HDAC protein activity. In certain embodiments, the HDAC protein and HDAC protein activity may refer to HDAC6 protein and HDAC6 protein activity.

The term "isostere" refers to a group or molecule whose chemical and/or physical properties are similar to those of another group or molecule. A "bioisostere" is a type of isostere and refers to a group or molecule whose biological properties are similar to those of another group or molecule. For example, for the HDAC inhibitors described herein, a carboxylic acid may be replaced by one of the following bioisosteres for carboxylic acids, including, without limitation, alkyl esters (COOR), acylsulfonamides (CONR—SO$_2$R), hydroxamic acids (CONR—OH), hydroxamates (CONR—OR), tetrazoles, hydroxyisoxazoles, isoxazol-3-ones, and sulfonamides (SO$_2$NR), where each R may independently represent hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc.

which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "treat," "treatment," and/or "treating" may refer to the management of a disease, disorder, or pathological condition (e.g., cancer, neoplastic disorder, inflammatory disorder, immunological disorder, or neurological disorder) with the intent to cure, ameliorate, stabilize, prevent, or control the disease, disorder, pathological condition, or symptoms thereof. Regarding control of the disease, disorder, or pathological condition more specifically, "control" may include the absence of disease progression, as assessed by the response to the methods recited herein, where such response may be complete (e.g., placing the disease in remission) or partial (e.g., slowing the spread of cancerous cells and tissues and/or preventing, slowing, or halting metastasis). The terms "treat," "treatment," and/or "treating" may further encompass, with respect to the treatment of cancer, the sensitization of cancerous cells and tissues (e.g., neoplastic cells and tissues) to radiation and/or the protection of non-cancerous cells from the effects of radiation.

For example, a patient responding to the methods of treatment disclosed herein may exhibit the absence of disease progression (e.g., halting the growth and/or spread of neoplastic cells and tissues) over another patient that does not receive the methods of treatment described herein.

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule. For example, the compounds described herein may modulate (i.e., inhibit) HDAC protein. In some embodiments, the compounds described herein may selectively modulate (i.e., selectively inhibit) a first HDAC protein as compared to a second HDAC protein. In certain embodiments, the compounds described herein may selectively modulate (i.e., selectively inhibit) HDAC6 protein as compared to other HDAC proteins including, but not limited to, HDAC1 and/or HDAC3. In certain embodiments, the compounds described herein may selectively modulate (i.e., selectively inhibit) HDAC6 protein as compared to HDAC1 protein. In certain embodiments, the compounds described herein may selectively modulate (i.e., selectively inhibit) HDAC6 protein as compared to HDAC3 protein.

In some embodiments, a selective HDAC6 inhibitor is a compound that is at least 10, 11, 12, 13, 14, 15, 16, 17, 18, 19, 20, 21, 22, 23, 24, 25, 26, 27, 28, 29, or 30 times more selective for HDAC6 than HDAC1 as measured by determining the $IC_{50}$ values for the selective HDAC6 inhibitor in an in vitro HDAC enzyme inhibition assay comparing HDAC6 protein and HDAC1 protein, as described herein. In some embodiments, a selective HDAC6 inhibitor is a compound that is about 10, 11, 12, 13, 14, 15, 16, 17, 18, 19, 20, 21, 22, 23, 24, 25, 26, 27, 28, 29, or 30 times more selective for HDAC6 than HDAC1 as measured by determining the $IC_{50}$ values for the selective HDAC6 inhibitor in an in vitro HDAC enzyme inhibition assay comparing HDAC6 protein and HDAC1 protein, as described herein.

In some embodiments, a selective HDAC6 inhibitor is a compound that is at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 times more selective for HDAC6 than HDAC3 as measured by determining the $IC_{50}$ values for the selective HDAC6 inhibitor in an in vitro HDAC enzyme inhibition assay comparing HDAC6 protein and HDAC3 protein. In some embodiments, a selective HDAC6 inhibitor is a compound that is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 times more selective for HDAC6 than HDAC3 as measured by determining the $IC_{50}$ values for the selective HDAC6 inhibitor in an in vitro HDAC enzyme inhibition assay comparing HDAC6 protein and HDAC3 protein.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" or "physilogically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Remington: The Science and Practice of Pharmacy, 20$^{th}$ edition, A. R. Genaro et al., Part 5, Pharmaceutical Manufacturing, pp. 669-1015 (Lippincott Williams & Wilkins, Baltimore, Md./Philadelphia, Pa.) (2000) discloses various carriers used in formulating pharmaceutical compositions and known techniques for the preparation thereof. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods. Except insofar as any conventional pharmaceutical carrier medium is incompatible with either the compounds used as described herein, such as by producing an undesirable biological effect or otherwise interacting in a deleterious manner with any other component(s) of a formulation comprising such compounds or agents, its use is contemplated to be within the scope of this invention.

A "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of formulas Ia, Ib, II, and/or III. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula Ia, Ib, II, and/or III) is a prodrug within the scope of the invention. Various forms of prodrugs are well known in the art. A comprehensive description of pro drugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting, lymphocyte targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the invention.

As used herein, the term "subject" or "patient" may refer to any mammal. Exemplary mammals include laboratory animals, including rodents such as mice, rats and guinea pigs; farm animals such as cows, sheep, pigs and goats; pet animals such as dogs and cats; and primates such as monkeys, apes and humans. In certain embodiments, the "subject" or "patient" is a human subject or patient.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (iso-propyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$), —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., (C$_{2-10}$)alkenyl or C$_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O) OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N (R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., (C$_{2-10}$)alkynyl or C$_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC (O)N(R$^a$)$_2$, —C(O)N(R$^a$)$_2$, —N(R$^a$)C(O)OR$^a$, —N(R$^a$)C (O)R$^a$, —N(R$^a$)C(O)N(R$^a$)$_2$, N(R$^a$)C(NR$^a$)N(R$^a$)$_2$, —N(R$^a$) S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Acylsulfonamide" refers to the group —C(=O)NR$^a$—S(=O)R$^a$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl, or heteroarylalkyl.

"Carboxaldehyde" refers to a —(C=O)H radical.

"Carbonyl" refers to the group —C(=O)—. Carbonyl groups may be substituted with the following exemplary substituents: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —NR$^a$—OR$^a$—, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N (R$^a$), —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. (C$_{3-10}$)cycloalkyl or C$_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, acylsulfonamido, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$), —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N($R^a$)$_2$ group has two $R^a$ substituents other than hydrogen, they can be combined with the nitrogen atom to form a 4-, 5-, 6- or 7-membered ring. For example, —N($R^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —O$R^a$, —S$R^a$, —S(O)$_t R^a$— (where t is 1 or 2), —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NH$R^a$, and N$R^a R^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, amino, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, *Protective Groups in Organic Synthesis*, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —O$R^a$, —S$R^a$, —S(O)$_t R^a$— (where t is 1 or 2), —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —O$R^a$, —S$R^a$, —S(O)$_t R^a$— (where t is 1 or 2), —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, acylsulfonamido, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$), —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, isoxazol-3-one, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$), —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Hydroxamate" refers to the —C(O)NR$^a$OR$^a$ moiety, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Nitro" refers to the —NO$_2$ radical.

"Oxa" refers to the —O— radical.

"Oxo" refers to the =O radical.

As used herein, the term "substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxamate, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties. The chemical moieties of formulas Ia, Ib, II, and/or III, above, that may be optionally substituted include alkyl, alkenyl, alkynyl, cycloalkyl, arylalkyl, aryl, heterocycle, and heteroaryl. For example, optionally substituted alkyl may include both propyl and 2-chloro-propyl. Additionally, "optionally substituted" is also inclusive of embodiments where the named substituent or substituents have multiple substituents rather than simply a single substituent. For example, optionally substituted aryl may include both phenyl and 3-methyl-5-ethyl-6-chloro-phenyl.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions*, Wiley Interscience, New York (1981); E. L. Eliel, *Stereochemistry of Carbon Compounds*, McGraw-Hill, New York (1962); and E. L. Eliel and S. H. Wilen, *Stereochemistry of Organic Compounds*, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, *Protective Groups in Organic Synthesis,* 3rd Edition, John Wiley & Sons, New York (1999).

"Solvate" refers to a compound in physical association with one or more molecules of a pharmaceutically acceptable solvent.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Compounds of the invention also include antibodies. The terms "antibody" and its plural form "antibodies" refer to whole immunoglobulins and any antigen-binding fragment ("antigen-binding portion") or single chains thereof. An "antibody" further refers to a glycoprotein comprising at least two heavy (H) chains and two light (L) chains interconnected by disulfide bonds, or an antigen-binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions of an antibody may be further subdivided into regions of hypervariability, which are referred to as complementarity determining regions (CDR) or hypervariable regions (HVR), and which can be interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen epitope or epitopes. The constant regions of the antibodies may mediate the binding of the immunoglobulin to host tissues or factors, including various cells of the immune system (e.g., effector cells) and the first component (Clq) of the classical complement system.

The terms "monoclonal antibody," "mAb," "monoclonal antibody composition," or their plural forms refer to a preparation of antibody molecules of single molecular composition. A monoclonal antibody composition displays a single binding specificity and affinity for a particular epitope. Monoclonal antibodies recited herein and/or those specific to, e.g., PD-1 or PD-L1, can be made using knowledge and skill in the art of injecting test subjects with a corresponding antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

The terms "antigen-binding portion" or "antigen-binding fragment" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and CH1 domains; (ii) a F(ab')2 fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v)

a domain antibody (dAb) fragment (Ward et al., Nature, 1989, 341, 544-546), which may consist of a $V_H$ or a $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see, e.g., Bird et al., Science 1988, 242, 423-426; and Huston et al., Proc. Natl. Acad. Sci. USA 1988, 85, 5879-5883). Such scFv antibodies are also intended to be encompassed within the terms "antigen-binding portion" or "antigen-binding fragment" of an antibody. These antibody fragments are obtained using conventional techniques known to those with skill in the art, and the fragments are screened for utility in the same manner as are intact antibodies.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). The term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes. In mammals, there are five antibody isotypes: IgA, IgD, IgG, IgM and IgE. In humans, there are four subclasses of the IgG isotype: IgG1, IgG2, IgG3 and IgG4, and two subclasses of the IgA isotype: IgA1 and IgA2.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another active pharmaceutical ingredient or antibody. The terms "conjugate," "antibody-drug conjugate", "ADC," or "immunoconjugate" refers to an antibody, or a fragment thereof, conjugated to a therapeutic moiety, such as a bacterial toxin, a cytotoxic drug or a radionuclide-containing toxin. Toxic moieties can be conjugated to antibodies of the invention using methods available in the art.

The terms "humanized antibody," "humanized antibodies," and "humanized" are intended to refer to antibodies in which CDR sequences derived from the germline of another mammalian species, such as a mouse, have been grafted onto human framework sequences. Additional framework region modifications may be made within the human framework sequences. Humanized forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a 15 hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 1986, 321, 522-525; Riechmann et al., Nature 1988, 332, 323-329; and Presta, Curr. Op. Struct. Biol. 1992, 2, 593-596.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "diabody" is a small antibody fragment with two antigen-binding sites. The fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., European Patent No. EP 404,097, International Patent Publication No. WO 93/11161; and Bolliger et al., *Proc. Natl. Acad. Sci. USA* 1993, 90, 6444-6448.

The term "glycosylation" refers to a modified derivative of an antibody. An aglycoslated antibody lacks glycosylation. Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Aglycosylation may increase the affinity of the antibody for antigen, as described in U.S. Pat. Nos. 5,714,350 and 6,350,861. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see e.g. U.S. Patent Publication No. 2004/0110704 or Yamane-Ohnuki, et al. *Biotechnol. Bioeng.*, 2004, 87, 614-622). As another example, European Patent No. EP 1,176,195 describes a cell line with a functionally disrupted FUT8 gene, which encodes a fucosyl transferase, such that antibodies expressed in such a cell line exhibit hypofucosylation by reducing or eliminating the alpha 1,6 bond-related enzyme, and also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). International Patent Publication WO 03/035835 describes a variant CHO cell line, Lec 13 cells, with reduced ability to attach fucose to Asn(297)-linked carbohydrates, also resulting in hypofucosylation of antibodies expressed in that host cell (see also Shields, et al., *J. Biol. Chem.* 2002, 277, 26733-26740. International Patent Publication WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana, et al., *Nat. Biotech.* 1999, 17, 176-180). Alternatively, the fucose residues of the antibody may be cleaved off using a fucosidase enzyme. For example, the fucosidase alpha-L-fucosidase removes fucosyl residues from antibodies as described in Tarentino, et al., *Biochem.* 1975, 14, 5516-5523.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody to be pegylated may be an aglycosylated antibody. Methods for pegylation are known in the art and can be applied to the antibodies of the invention, as described for example in European Patent Nos. EP 0154316 and EP 0401384.

The term "radioisotope-labeled complex" refers to both non-covalent and covalent attachment of a radioactive isotope, such as $^{90}$Y, $^{111}$In, or $^{131}$I, to an antibody, including conjugates.

The term "biosimilar" means a biological product that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference anti-CD20 monoclonal antibody is rituximab, an anti-CD20 biosimilar monoclonal antibody approved by drug regulatory authorities with reference to rituximab is a "biosimilar to" rituximab or is a "biosimilar thereof" of rituximab. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorised, approved for authorisation or subject of an application for authorisation under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorised by the EMA. However, in some instances, the biosimilar may be compared to a biological medicinal product which has been authorised outside the European Economic Area (a non-EEA authorised "comparator") in certain studies. Such studies include for example certain clinical and in vivo non-clinical studies. As used herein, the term "biosimilar" also relates to a biological medicinal product which has been or may be compared to a non-EEA authorised comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorised or considered suitable for authorisation. In certain circumstances, the biosimilar exhibits different binding characteristics as compared to the reference medicinal product, wherein the different binding characteristics are considered by a Regulatory Authority such as the EMA not to be a barrier for authorisation as a similar biological product. The term "biosimilar" is also used synonymously by other national and regional regulatory agencies.

The terms "sequence identity," "percent identity," and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, Calif.) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

Certain embodiments described herein may comprise a variant of an antibody. As used herein, the term "variant" encompasses but is not limited to antibodies which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Histone Deacetylase (HDAC) Protein

Histone acetylation and deacetylation play important roles in chromatin folding and maintenance. Acetylation appears to play a role in the epigenetic regulation of chromatin structure, and gene expression, through the balance of histone acetyltransferase (HAT) and histone deacetylase (HDAC) activities. Increased acetylation of histones leads to changes in chromatin structure and accessibility for key cellular proteins to specific target sites. HATs acetylate lysine groups at the amino terminal tails of nuclear histones to neutralize positive charges on the histones, yielding a more open, transcriptionally active chromatin structure. In contrast, the HDACs deacetylate and suppress transcription. In this model, inhibitors of HDACs bias the balance toward a more acetylated state. Such a shift in the relative activities of these enzymes may affect gene expression necessary for DNA repair, replication, cell cycle checkpoint activation and tumor suppression.

Human HDACs may be divided into four classes based on structure, sequence homology, and domain organization. Class I consists of HDACs 1, 2, 3, 8, and 11, albeit a recent report puts HDAC 11 into a new class, class IV, based on a phylogenetic analysis. Class I HDACs are nuclear and play roles in cell proliferation and apoptosis. Class II includes HDACs 4, 5, 6, 7, 9, and 10. These enzymes are characterized by a large $NH_2$-terminal domain or a second catalytic site and their expression is more restricted, suggesting roles in cellular differentiation and development. Class III enzymes, include the sirtuins (SIRTs), and are NAD-dependent deacetylases. These are not inhibited by Trichostatin A (TSA) or other hydroxamates.

HDACs are found in the nuclear and cytoplasmic compartments. Although they are involved in critical cellular functions, such as cell cycle regulation and apoptosis, a key function of HDACs is transcriptional regulation. HDACs function as components of large multi-protein complexes that bind to promoters and repress transcription. Class II compounds shuttle between the nucleus and the cytoplasm. However, certain classes of HDACs have conserved deacetylase core domains of approximately 400 amino acids and zinc binding sites. It is the core domain that presents the principal target for design of inhibitory small molecules.

In response to DNA damage, signal transduction pathways may be activated to regulate cell cycle arrest, repair, differentiation, apoptosis, and transcription. Such responses are a complex feature of the cellular radiation phenotype, and their effectiveness may determine cell survival or death. DNA damage checkpoints generate signals that arrest cell cycle progression until the damage is repaired. When damaged DNA is repaired, checkpoint signals are reversed to resume cell cycle progression. Such DNA-directed processes are accompanied by highly localized changes in chromatin structure. Various recent studies have implicated chromatin structure in DNA damage signaling and repair. Post-translational histone modifications regulate chromatin structure and access for proteins to damaged DNA sites as reported for repair and signaling proteins to the damaged regions of DNA.

Early HDAC inhibitors (e.g., benzamides) were investigated as differentiating agents, without full understanding of their molecular mechanisms. Some of these agents have advanced to clinical trials. The full recognition of the potential for HDAC inhibitors was advanced with the discovery and development of hydroxamic acid inhibitors. Hydroxamic acid based compounds (e.g., suberoylanilide hydroxamic acid (SAHA)) have been developed for clinical application, and have proven to be relatively non-toxic. SAHA has been approved by the FDA for the treatment of cutaneous T-cell lymphoma. Certain HDAC inhibitors have been described in U.S. Pat. Nos. 7,507,828; 7,842,835; 8,067,600; 8,222,451; and 8,748,463; the entirety of which are incorporated herein by reference.

Other chemical families of HDAC inhibitors, including depsipeptide and valproic acid, have been shown to inhibit cancer cell growth in vitro and in vivo. Modulation of p53, ErbB1, ErbB2 and Raf-1 expression have been observed following exposure of lung cancer cells to depsipeptide, a drug currently in clinical trials. For example, Valproic acid has been used clinically as an anti-epileptic agent, with excellent reasonable toxicity profile and has been shown to be involved in the proteolysis of HDAC2.

However, pan-HDAC inhibitors have multiple toxicities due to off-target effects. A molecule targeting the HDAC6 protein has a better chance for treating diseases, as compared to more promiscuous HDAC inhibitors, with less toxicity.

HDAC Inhibitors

The HDAC inhibitors of the invention may include one or more compounds of formula Ia, Ib, II, and/or III. In some embodiments, the HDAC inhibitors of the invention are selective HDAC6 inhibitors.

In some embodiments, the HDAC inhibitor of the invention is $N^1$-(2,6-dioxopiperidin-3-yl)-$N^8$-hydroxyoctanediamide or:

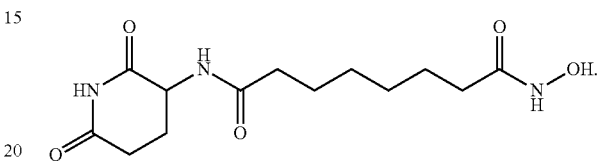

In some embodiments, the HDAC inhibitor of the invention is $N^1$-(2-(2,6-dioxopiperidin-3-yl)-1-oxoisoindolin-4-yl)-$N^8$-hydroxyoctanediamide or:

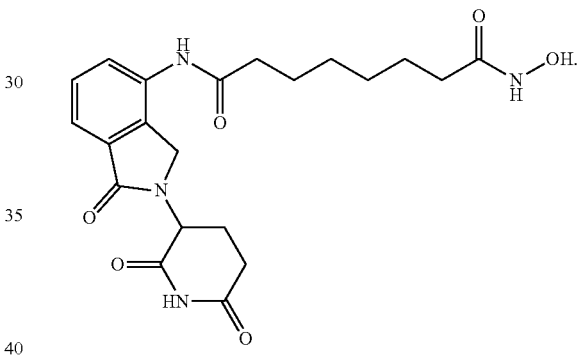

Certain HDAC inhibitors of the invention are selective HDAC6 inhibitors. For example, $N^1$-(2,6-dioxopiperidin-3-yl)-$N^8$-hydroxyoctanediamide and $N^1$-(2-(2,6-dioxopiperidin-3-yl)-1-oxoisoindolin-4-yl)-$N^8$-hydroxyoctanediamide are HDAC inhibitors that are also selective HDAC6 inhibitors.

In some embodiments, $N^1$-(2,6-dioxopiperidin-3-yl)-$N^8$-hydroxyoctanediamide and/or $N^1$-(2-(2,6-dioxopiperidin-3-yl)-1-oxoisoindolin-4-yl)-$N^8$-hydroxyoctanediamide may be prepared racemically or may be prepared in the form of their (R)- or (S)-enantiomers.

In some embodiments, the enantiomerically enriched preparation of

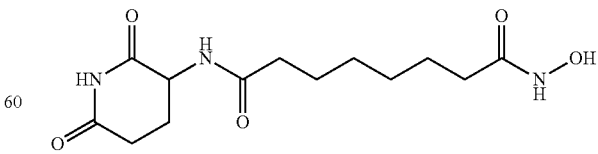

as the (S)-enantiomer has a higher potency with respect to therapeutic utility per unit mass than does the racemic mixture of that composition. In some embodiments, the enantiomerically enriched preparation of

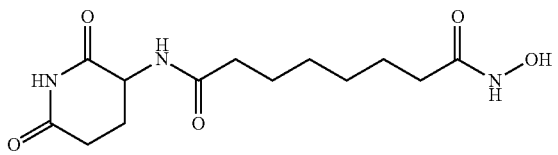 [SMILES: O=C(CCCCCCC(=O)NC1CCC(=O)NC1=O)NO]

as the (R)-enantiomer has a higher potency with respect to therapeutic utility per unit mass than does the racemic mixture of that composition. In some embodiments, the enantiomerically enriched preparation of

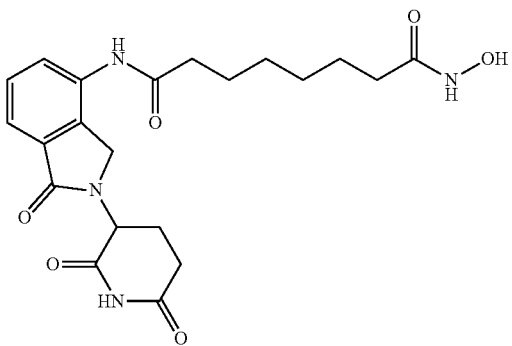 [SMILES: O=C(CCCCCCC(=O)Nc1cccc2c1CN(C1CCC(=O)NC1=O)C2=O)NO]

as the (S)-enantiomer has a higher potency with respect to therapeutic utility per unit mass than does the racemic mixture of that composition. In some embodiments, the enantiomerically enriched preparation of

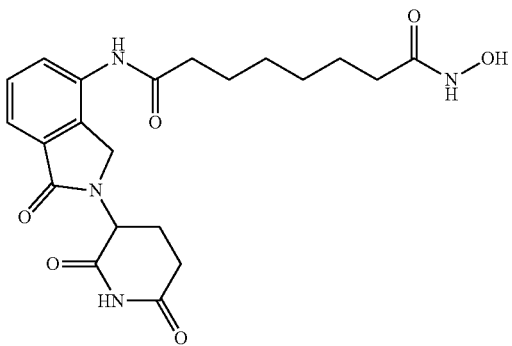 [SMILES: O=C(CCCCCCC(=O)Nc1cccc2c1CN(C1CCC(=O)NC1=O)C2=O)NO]

as the (R)-enantiomer has a higher potency with respect to therapeutic utility per unit mass than does the racemic mixture of that composition.

In some embodiments, the HDAC inhibitors (e.g., selective HDAC6 inhibitors) described herein may be delivered as listed or as a pharmaceutically acceptable salt, solvate, hydrate, cocrystal, tautomer, or prodrug thereof.

In some embodiments, the pharmaceutical compositions and methods described herein include one or more of the foregoing HDAC inhibitors or selective HDAC6 inhibitors.

Chemotherapeutic Agents

In some embodiments, the pharmaceutical compositions and methods described herein may include one or more additional therapeutic agents. The additional therapeutic agents may include one or more chemotherapeutic agents.

In some embodiments, the chemotherapeutic agents may include one or more of bortezomib (Velcade®; see, e.g., U.S. Pat. Nos. 5,780,454, 6,713,446, and 6,958,319), lenalidomide (Revlimid®; see, e.g., U.S. Pat. Nos. 5,635,517, 6,045,501, 6,281,230, 6,315,720, 6,555,554, 6,561,976, 6,561,976, 6,561,977, 6,755,784, 6,908,432, 7,119,106, 7,189,740, 7,465,800, 7,468,363, 7,855,217, 7,968,569, 8,204,763, 8,288,415, 8,315,886, 8,404,717, 8,530,498, 8,589,188, 8,626,531, 8,648,095, 8,741,929, 9,056,120, 9,101,621, and 9,101,622), temozolomide (see, e.g., U.S. Pat. No. 5,939,098), 5-fluorouracil (5-FU; see, e.g., U.S. Pat. No. 4,130,648), 6-mercaptopurine (6-MP; see, e.g., U.S. Pat. No. 8,188,067), Capecitabine (Xeloda®; see, e.g., U.S. Pat. Nos. 4,966,891, 5,453,497, 5,472,949, and 5,476,932), Cladribine (see, e.g., U.S. Pat. No. 6,271,245), Clofarabine (see, e.g., U.S. Pat. No. 5,661,136), Cytarabine (Ara-C®; see, e.g., U.S. Pat. Nos. 5,455,044 and 5,723,147), Floxuridine (see, e.g., U.S. Pat. No. 6,271,245), Fludarabine (see, e.g., U.S. Pat. No. 6,271,245), Gemcitabine (Gemzar®; see, e.g., U.S. Pat. Nos. 4,808,614 and 5,464,826), Hydroxyurea (see, U.S. Pat. No. 3,968,249), Methotrexate (see, e.g., U.S. Pat. No. 6,271,245), Pemetrexed (Alimta®; see, e.g., U.S. Pat. Nos. 5,344,932 and 7,772,209), Pentostatin (see, e.g., U.S. Pat. No. 6,316,435), Thioguanine (see, e.g., U.S. Pat. No. 3,163,639), daunorubicin (see, e.g., U.S. Pat. No. 7,727,968), doxorubicin (see, e.g., U.S. Pat. No. 6,271,245), epirubicin (see, e.g., U.S. Pat. No. 8,410,131), idaurubicin (see, e.g., U.S. Pat. No. 6,271,245), topotecan (see, e.g., U.S. Pat. No. 8,410,131), irinotecan (see, e.g., U.S. Pat. No. 8,410,131), etoposide (see, e.g., U.S. Pat. No. 6,271,245), teniposide (see, e.g., U.S. Pat. No. 6,271,245), mitoxantrone (see, e.g., U.S. Pat. No. 6,271,245), Vinblastine (see, e.g., U.S. Pat. No. 6,271,245), vincristine (see, e.g., U.S. Pat. No. 6,271,245), vinorelbine (see, e.g., U.S. Pat. No. 8,410,131), estramustine (see, e.g., U.S. Pat. No. 6,849,616), paclitaxel (see, e.g., U.S. Pat. No. 6,271,245), dexamethasone (see, e.g., U.S. Pat. No. 8,822,438), and docetaxel (see, e.g., U.S. Pat. No. 8,410,131).

In any of the methods described herein, the chemotherapeutic agents or combinations thereof may be administered before, concurrently, or after administration of the compounds of Formulas Ia, Ib, II, III, and/or the immunotherapeutic agents described herein.

Immunotherapeutic Agents

In some embodiments, the pharmaceutical compositions and methods described herein may include one or more additional therapeutic agents. The additional therapeutic agents may include one or more immunotherapeutic agents.

In some embodiments, the immunotherapeutic agents may include one or more of a PD-1 inhibitor and a PD-L1 inhibitor, wherein the PD-1 inhibitor and PD-L1 inhibitor may be selected from the group consisting of nivolumab, pembrolizumab, pidilizumab, durvalumab, atezolizumab, and avelumab, and any fragment, derivative, conjugate, variant, radioisotope-labeled complex, or biosimilar thereof.

In some embodiments, the immunotherapeutic agents may include one or more of rituximab, trastuzumab, ibritumomab, tositumomab, cetuximab, bevacizumab, gemtuzumab, alemtuzumab, and BL22, and any fragment, derivative, conjugate, variant, radioisotope-labeled complex, or biosimilar thereof.

In any of the methods described herein, the immunotherapeutic agents (e.g., the monoclonal antibodies) or combinations thereof may be administered before, concurrently, or after administration of the compounds of Formulas Ia, Ib, II, III, and/or the chemotherapeutic agents described herein.

PD-1 and PD-L1 Inhibitors

In some embodiments, the methods and/or compositions described herein include a combination of an HDAC inhibitor (e.g., a selective HDAC inhibitor) and one or more immunotherapeutic agents. In some embodiments, the immunotherapeutic agents may include one or more programmed death-1 (PD-1) and programmed death ligand 1 (PD-L1) inhibitors.

In some embodiments, the PD-1 or PD-L1 inhibitor (e.g., an ant-PD-1 antibody) for use in combination with HDAC inhibitor (e.g., a selective HDAC inhibitor) is selected from the group consisting of nivolumab, pembrolizumab, pidilizumab, durvalumab, atezolizumab, avelumab, and any fragment, derivative, conjugate, variant, radioisotope-labeled complex, or biosimilar thereof.

In an embodiment, an anti-PD-1 antibody comprises nivolumab (also known as OPDIVO and commercially available from Bristol-Myers Squibb Co.), or biosimilars, antigen-binding fragments, conjugates, or variants thereof. Nivolumab is referred to as 5C4 in International Patent Publication No. WO 2006/121168. Nivolumab is assigned Chemical Abstracts Service (CAS) registry number 946414-94-4 and is also known as BMS-936558, MDX-1106 or ONO-4538. Nivolumab is a fully human IgG4 antibody blocking the PD-1 receptor. The clinical safety and efficacy of nivolumab in various forms of cancer has been described in Wang et al., *Cancer Immunol Res.* 2014, 2, 846-56; Page et al., *Ann. Rev. Med.,* 2014, 65, 185-202; and Weber et al., *J. Clin. Oncology,* 2013, 31, 4311-4318. The nivolumab monoclonal antibody includes a heavy chain given by SEQ ID NO:1 and a light chain given by SEQ ID NO:2. Nivolumab has intra-heavy chain disulfide linkages at 22-96, 140-196, 254-314, 360-418, 22'-96", 140"-196", 254"-314", and 360"-418"; intra-light chain disulfide linkages at 23'-88', 134'-194', 23'''-88''', and 134'''-194'''; inter-heavy-light chain disulfide linkages at 127-214', 127-214''', inter-heavy-heavy chain disulfide linkages at 219-219" and 222-222"; and N-glycosylation sites (H $CH_2$ 84.4) at 290, 290".

In an embodiment, the anti-PD-1 antibody is an anti-PD-1 biosimilar monoclonal antibody approved by drug regulatory authorities with reference to nivolumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is nivolumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is nivolumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab.

In an embodiment, the anti-PD-1 antibody is an antibody disclosed and/or prepared according to U.S. Pat. No. 8,008,449 or U.S. Patent Application Publication Nos. 2009/0217401 A1 or 2013/0133091 A1, the disclosures of which are specifically incorporated by reference herein. For example, in an embodiment, the monoclonal antibody includes 5C4 (referred to herein as nivolumab), 17D8, 2D3, 4H1, 4A11, 7D3, and 5F4, described in U.S. Pat. No. 8,008,449, the disclosures of which are hereby incorporated by reference. The PD-1 antibodies 17D8, 2D3, 4H1, 5C4, and 4A11, are all directed against human PD-1, bind specifically to PD-1 and do not bind to other members of the CD28 family. The sequences and CDR regions for these antibodies are provided in U.S. Pat. No. 8,008,449, in particular in FIG. 1 through FIG. 12; the disclosures of which are incorporated by reference herein.

In another embodiment, the anti-PD-1 antibody comprises pembrolizumab (also known as KEYTRUDA), which is commercially available from Merck, or antigen-binding fragments, conjugates, or variants thereof. Pembrolizumab is assigned CAS registry number 1374853-91-4 and is also known as lambrolizumab, MK-3475, and SCH-900475. The structure, properties, uses, and preparation of pembrolizumab are described in International Patent Publication No. WO 2008/156712 A1, U.S. Pat. No. 8,354,509 and U.S. Patent Application Publication Nos. US 2010/0266617 A1, US 2013/0108651 A1, and US 2013/0109843 A2, the disclosures of which are incorporated herein by reference. Pembrolizumab has an immunoglobulin G4, anti-(human protein PDCD1 (programmed cell death 1)) (human-*Mus musculus* monoclonal heavy chain), disulfide with human-*Mus musculus* monoclonal light chain, dimer structure. The structure of pembrolizumab may also be described as immunoglobulin G4, anti-(human programmed cell death 1); humanized mouse monoclonal [228-L-proline(H10-S>P)]γ4 heavy chain (134-218')-disulfide with humanized mouse monoclonal κ light chain dimer (226-226":229-229")-bis-disulfide. The clinical safety and efficacy of pembrolizumab in various forms of cancer is described in Fuerst, *Oncology Times,* 2014, 36, 35-36; Robert et al., *Lancet,* 2014, 384, 1109-17; and Thomas et al., *Exp. Opin. Biol. Ther.,* 2014, 14, 1061-1064. In an embodiment, the pembrolizumab monoclonal antibody includes a heavy chain given by SEQ ID NO:11 and a light chain given by SEQ ID NO: 12, and includes the following disulfide bridges: 22-96, 22"-96", 23'-92', 23'''-92''', 134-218', 134"-218''', 138'-198', 138'''-198''', 147-203, 147-203", 226-226", 229-229''', 261-321, 261"-321", 367-425, and 367"-425", and the following glycosylation sites (N): Asn-297 and Asn-297". Pembrolizumab is an IgG4/kappa isotype with a stabilizing S228P mutation in the Fc region; insertion of this mutation in the IgG4 hinge region prevents the formation of half molecules typically observed for IgG4 antibodies. Pembrolizumab is heterogeneously glycosylated at Asn297 within the Fc domain of each heavy chain, yielding a molecular weight of approximately 149 kDa for the intact antibody. The dominant glycoform of pembrolizumab is the fucosylated agalacto diantennary glycan form (GOF).

In an embodiment, the anti-PD-1 antibody is an anti-PD-1 biosimilar monoclonal antibody approved by drug regulatory authorities with reference to pembrolizumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is pembrolizumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is pembrolizumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab.

In an embodiment, the anti-PD-1 antibody is an antibody disclosed in U.S. Pat. No. 8,354,509 or U.S. Patent Application Publication Nos. 2010/0266617 A1, 2013/0108651 A1, 2013/0109843 A2, the disclosures of which are specifically incorporated by reference herein.

In an embodiment, the anti-PD-1 antibody is pidilizumab, which is also known as CT-011 (CureTech Ltd.), and which is disclosed in U.S. Pat. No. 8,686,119 B2, the disclosures of which are specifically incorporated by reference herein. The efficacy of pidilizumab in the treatment of cancers, such as hematological malignancies, is described in Berger, et al., *Clin. Cancer Res.* 2008, 14, 3044-51. The pidilizumab monoclonal antibody includes a heavy chain given by SEQ ID NO:21 and a light chain given by SEQ ID NO:22. Pidilizumab has intra-heavy chain disulfide linkages at 22-96, 144-200, 261-321, 367-425, 22"-96", 144"-200", 261"-321", and 367"-425"; intra-light chain disulfide linkages at 23'-87', 133'-193', 23'''-87''', and 133'''-193'''; inter-heavy-light chain disulfide linkages at 220-213' and 220"-213'", inter-heavy-heavy chain disulfide linkages at 226-226" 229-229"; and N-glycosylation sites (H $CH_2$ 84.4) at 297, 297".

In an embodiment, the anti-PD-1 antibody is an anti-PD-1 biosimilar monoclonal antibody approved by drug regulatory authorities with reference to pidilizumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is pidilizumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is pidilizumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pidilizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pidilizumab.

In an embodiment, anti-PD-1 antibodies and other PD-1 inhibitors include those described in U.S. Pat. Nos. 8,287,856, 8,580,247, and 8,168,757 and U.S. Patent Application Publication Nos. 2009/0028857 A1, 2010/0285013 A1, 2013/0022600 A1, and 2011/0008369 A1, the teachings of which are hereby incorporated by reference. In another embodiment, antibodies that compete with any of these antibodies for binding to PD-1 are also included. In another embodiment, the anti-PD-1 antibody is an antibody disclosed in U.S. Pat. No. 8,735,553 B1, the disclosures of which are incorporated herein by reference.

In an embodiment, the anti-PD-1 antibody is a commercially-available monoclonal antibody, such as anti-m-PD-1 clones J43 (Cat #BE0033-2) and RMP1-14 (Cat #BE0146) (Bio X Cell, Inc.). A number of commercially-available anti-PD-1 antibodies are known to one of ordinary skill in the art.

In an embodiment, the PD-1 inhibitor may be a small molecule or a peptide, or a peptide derivative, such as those described in U.S. Pat. Nos. 8,907,053; 9,096,642; and 9,044,442 and U.S. Patent Application Publication No. 2015/0087581; 1,2,4 oxadiazole compounds and derivatives such as those described in U.S. Patent Application Publication No. 2015/0073024; cyclic peptidomimetic compounds and derivatives such as those described in U.S. Patent Application Publication No. 2015/0073042; cyclic compounds and derivatives such as those described in U.S. Patent Application Publication No. 2015/0125491; 1,3,4 oxadiazole and 1,3,4 thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. 2014/0294898; the disclosures of each of which are hereby incorporated by reference in their entireties.

The anti-PD-1 antibody sequences discussed and referenced in some of the foregoing embodiments are summarized in Table 1.

TABLE 1

Anti-PD-1 antibody amino acid sequences.

| Identifier | Sequence (One-Letter Amino Acid Symbols) | |
|---|---|---|
| SEQ ID NO: 1<br>nivolumab<br>heavy chain | QVQLVESGGG WQPGRSLRL DCKASGITFS NSGMHWVRQA PGKGLEWVAV IWYDGSKRYY<br>ADSVKGRFTI SRDNSKNTLF LQMNSLRAED TAVYYCATND DYWGQGTLVT VSSASTKGPS<br>VFPLAPCSRS TSESTAALGC LVKDYFPEPV TVSWNSGALT SGVHTFPAVL QSSGLYSLSS<br>WTVPSSSLG TKTYTCNVDH KPSNTKVDKR VESKYGPPCP PCPAPEFLGG PSVFLFPPKP<br>KDTLMISRTP EVTCVWDVS QEDPEVQFNW YVDGVEVHNA KTKPREEQFN STYRWSVLT<br>VLHQDWLNGK EYKCKVSNKG LPSSIEKTIS KAKGQPREPQ VYTLPPSQEE MTKNQVSLTC<br>LVKGFYPSDI AVEWESNGQP ENNYKTTPPV LDSDGSFFLY SRLTVDKSRW QEGNVFSCSV<br>MHEALHNHYT QKSLSLSLGK | 60<br>120<br>180<br>240<br>300<br>360<br>420<br>440 |
| SEQ ID NO: 2<br>nivolumab<br>light chain | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ SSNWPRTFGQ GTKVEIKRTV AAPSVFIFPP<br>SDEQLKSGTA SWCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 3<br>nivolumab<br>variable<br>heavy chain | QVQLVESGGG WQPGRSLRL DCKASGITFS NSGMHWVRQA PGKGLEWVAV IWYDGSKRYY<br>ADSVKGRFTI SRDNSKNTLF LQMNSLRAED TAVYYCATND DYWGQGTLVT VSS | 60<br>113 |
| SEQ ID NO: 4<br>nivolumab<br>variable<br>light chain | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ SSNWPRTFGQ GTKVEIK | 60<br>107 |
| SEQ ID NO: 5<br>nivolumab<br>heavy chain<br>CDR1 | NSGMH | 5 |
| SEQ ID NO: 6<br>nivolumab<br>heavy chain<br>CDR2 | VIWYDGSKRY YADSVKG | 17 |
| SEQ ID NO: 7<br>nivolumab<br>heavy chain<br>CDR3 | NDDY | 4 |
| SEQ ID NO: 8<br>nivolumab<br>light chain<br>CDR1 | RASQSVSSYL A | 11 |
| SEQ ID NO: 9<br>nivolumab<br>light chain<br>CDR2 | DASNRAT | 7 |
| SEQ ID NO: 10<br>nivolumab<br>light chain<br>CDR3 | QQSSNWPRT | 9 |
| SEQ ID NO: 11<br>pembrolizumab<br>heavy chain | QVQLVQSGVE VKKPGASVKV SCKASGYTFT NYYMYWVRQA PGQGLEWMGG INPSNGGTNF<br>NEKFKNRVTL TTDSSTTTAY MELKSLQFDD TAVYYCARRD YRFDMGFDYW GQGTTVTVSS<br>ASTKGPSVFP LAPCSRSTSE STAALGCLVK DYFPEPVTVS WNSGALTSGV HTFPAVLQSS<br>GLYSLSSWT VPSSSLGTKT YTCNVDHKPS NTKVDKRVES KYGPPCPPCP APEFLGGPSV<br>FLFPPKPKDT LMISRTPEVT CVWDVSQED PEVQFNWYVD GVEVHNAKTK PREEQFNSTY<br>RWSVLTVLH QDWLNGKEYK CKVSNKGLPS SIEKTISKAK GQPREPQVYT LPPSQEEMTK<br>NQVSLTCLVK GFYPSDIAVE WESNGQPENN YKTTPPVLDS DGSFFLYSRL TVDKSRWQEG<br>NVFSCSVMHE ALHNHYTQKS LSLSLGK | 60<br>120<br>180<br>240<br>300<br>360<br>420<br>447 |
| SEQ ID NO: 12<br>pembrolizumab<br>light chain | EIVLTQSPAT LSLSPGERAT LSCRASKGVS TSGYSYLHWY QQKPGQAPRL LIYLASYLES<br>GVPARFSGSG SGTDFTLTIS SLEPEDFAVY YCHQSRDLPL TFGGGTKVEI KRTVAAPSVF<br>IFPPSDEQLK SGTASWCLL NNFYPREAKV QWKVDNALQS GNSQESVTEQ DSKDSTYSLS<br>STLTLSKADY EKHKVYACEV THQGLSSPVT KSFNRGEC | 60<br>120<br>180<br>218 |
| SEQ ID NO: 13<br>pembrolizumab<br>variable<br>heavy chain | QVQLVQSGVE VKKPGASVKV SCKASGYTFT NYYMYWVRQA PGQGLEWMGG INPSNGGTNF<br>NEKFKNRVTL TTDSSTTTAY MELKSLQFDD TAVYYCARRD YRFDMGFDYW GQGTTVTVSS | 60<br>120 |

TABLE 1-continued

Anti-PD-1 antibody amino acid sequences.

| Identifier | Sequence (One-Letter Amino Acid Symbols) | |
|---|---|---|
| SEQ ID NO: 14 pembrolizumab variable light chain | EIVLTQSPAT LSLSPGERAT LSCRASKGVS TSGYSYLHWY QQKPGQAPRL LIYLASYLES GVPARFSGSG SGTDFTLTIS SLEPEDFAVY YCQHSRDLPL TFGGGTKVEI K | 60 111 |
| SEQ ID NO: 15 pembrolizumab heavy chain CDR1 | NYYMY | 5 |
| SEQ ID NO: 16 pembrolizumab heavy chain CDR2 | GINPSNGGTN FNEKFK | 16 |
| SEQ ID NO: 17 pembrolizumab heavy chain CDR3 | RDYRFDMGFD Y | 11 |
| SEQ ID NO: 18 pembrolizumab light chain CDR1 | RASKGVSTSG YSYLH | 15 |
| SEQ ID NO: 19 pembrolizumab light chain CDR2 | LASYLES | 7 |
| SEQ ID NO: 20 pembrolizumab light chain CDR3 | QHSRDLPLT | 9 |
| SEQ ID NO: 21 pidilizumab heavy chain | QVQLVQSGSE LKKPGASVKI SCKASGYTFT NYGMNWVRQA PGQGLQWMGW INTDSGESTY AEEFKGRFVF SLDTSVNTAY LQITSLTAED TGMYFCVRVG YDALDYWGQG TLVTVSSAST KGPSVFPLAP SSKSTSGGTA ALGCLVKDYF PEPVTVSWNS GALTSGVHTF PAVLQSSGLY SLSSWTVPS SSLGTQTYIC NVNHKPSNTK VDKRVEPKSC DKTHTCPPCP APELLGGPSV FLFPPKPKDT LMISRTPEVT CVWDVSHED PEVKFNWYVD GVEVHNAKTK PREEQYNSTY RWSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK | 60 120 180 240 300 360 420 447 |
| SEQ ID NO: 22 pidilizumab light chain | EIVLTQSPSS LSASVGDRVT ITCSARSSVS YMHWFQQKPG KAPKLWIYRT SNLASGVPSR FSGSGSGTSY CLTINSLQPE DFATYYCQQR SSFPLTFGGG TKLEIKRTVA APSVFIFPPS DEQLKSGTAS WCLLNNFYP REAKVQWKVD NALQSGNSQE SVTEQDSKDS TYSLSSTLTL SKADYEKHKV YACEVTHQGL SSPVTKSFNR GEC | 60 120 180 213 |
| SEQ ID NO: 23 pidilizumab variable heavy chain | QVQLVQSGSE LKKPGASVKI SCKASGYTFT NYGMNWVRQA PGQGLQWMGW INTDSGESTY AEEFKGRFVF SLDTSVNTAY LQITSLTAED TGMYFCVRVG YDALDYWGQG TLVTVSS | 60 117 |
| SEQ ID NO: 24 pidilizumab variable light chain | EIVLTQSPSS LSASVGDRVT ITCSARSSVS YMHWFQQKPG KAPKLWIYRT SNLASGVPSR FSGSGSGTSY CLTINSLQPE DFATYYCQQR SSFPLTFGGG TKLEIK | 60 106 |

The PD-L1 inhibitor may be any PD-L1 inhibitor or blocker known in the art. In particular, it is one of the PD-L1 inhibitors or blockers described in more detail in the following paragraphs. The terms "inhibitor" and "blocker" are used interchangeably herein in reference to PD-L1 inhibitors. For avoidance of doubt, references herein to a PD-L1 inhibitor that is an antibody may refer to a compound or fragment, derivative, conjugate, variant, radioisotope-labeled complex, or biosimilar thereof. For avoidance of doubt, references herein to a PD-L1 inhibitor may refer to a compound or a pharmaceutically acceptable salt, ester, solvate, hydrate, cocrystal, or prodrug thereof.

In an embodiment, the anti-PD-L1 antibody is durvalumab, also known as MEDI4736 (which is commercially available from Medimmune, LLC), or antigen-binding fragments, conjugates, or variants thereof. In an embodiment, the anti-PD-L1 antibody is an antibody disclosed in U.S. Pat. No. 8,779,108 or U.S. Patent Application Publication No. 2013/0034559, the disclosures of which are specifically incorporated by reference herein. The clinical efficacy of durvalumab (MEDI4736, SEQ ID NO:25 and SEQ ID NO:26) has been described in: Page et al., Ann. Rev. Med., 2014, 65, 185-202; Brahmer et al., J. Clin. Oncol. 2014, 32, 5s (supplement, abstract 8021); and McDermott et al.,

*Cancer Treatment Rev.*, 2014, 40, 1056-64. The durvalumab monoclonal antibody includes disulfide linkages at 22-96, 22"-96", 23'-89', 23'''-89''', 135'-195', 135'''-195''', 148-204, 148"-204", 215'-224, 215'''-224", 230-230", 233-233", 265-325, 265"-325", 371-429, and 371"-429'; and N-glycosylation sites at Asn-301 and Asn-301".

In an embodiment, the anti-PD-L1 antibody is an anti-PD-L1 biosimilar monoclonal antibody approved by drug regulatory authorities with reference to durvalumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is durvalumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is durvalumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab.

In an embodiment, anti-PD-L1 antibodies and other PD-L1 inhibitors include those described in U.S. Pat. No. 8,779,108 and U.S. Patent Application Publication No. 2013/0034559A1, the disclosures of which are hereby incorporated by reference. In another embodiment, antibodies that compete with any of these antibodies for binding to PD-L1 are also included.

In an embodiment, the anti-PD-L1 antibody is atezolizumab, also known as MPDL3280A or RG7446 (commercially available from Genentech, Inc.), or antigen-binding fragments, conjugates, or variants thereof. In an embodiment, the anti-PD-L1 antibody is an antibody disclosed in U.S. Pat. No. 8,217,149, the disclosure of which is specifically incorporated by reference herein. In an embodiment, the anti-PD-L1 antibody is an antibody disclosed in U.S. Patent Application Publication Nos. 2010/0203056 A1, 2013/0045200 A1, 2013/0045201 A1, 2013/0045202 A1, or 2014/0065135 A1, the disclosures of which are specifically incorporated by reference herein. The atezolizumab monoclonal antibody includes a heavy chain given by SEQ ID NO:35 and a light chain given by SEQ ID NO:36. Atezolizumab has intra-heavy chain disulfide linkages (C23-C104) at 22-96, 145-201, 262-322, 368-426, 22"-96", 145"-201", 262"-322", and 368"-426"; intra-light chain disulfide linkages (C23-C104) at 23'-88', 134'-194', 23'''-88''', and 134'''-194'''; intra-heavy-light chain disulfide linkage (h 5-CL 126) at 221-214' and 221"-214'''; intra-heavy-heavy chain disulfide linkages (h 11, h 14) at 227-227" and 230-230"; and N-glycosylation sites (H CH$_2$N84.4>A) at 298 and 298'.

In an embodiment, the anti-PD-L1 antibody is an anti-PD-L1 biosimilar monoclonal antibody approved by drug regulatory authorities with reference to atezolizumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is atezolizumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is atezolizumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab.

In an embodiment, the anti-PD-L1 antibody is avelumab, also known as MSB0010718C (commercially available from Merck KGaA/EMD Serono), or antigen-binding fragments, conjugates, or variants thereof. In an embodiment, the anti-PD-L1 antibody is an antibody disclosed in U.S. Patent Application Publication No. US 2014/0341917 A1, the disclosure of which is specifically incorporated by reference herein. The avelumab monoclonal antibody includes a heavy chain given by SEQ ID NO:45 and a light chain given by SEQ ID NO:46. Avelumab has intra-heavy chain disulfide linkages (C23-C104) at 22-96, 147-203, 264-324, 370-428, 22"-96", 147"-203", 264"-324", and 370"-428"; intra-light chain disulfide linkages (C23-C104) at 22'-90', 138'-197', 22'''-90''', and 138'''-197'''; intra-heavy-light chain disulfide linkages (h 5-CL 126) at 223-215' and 223"-215'''; intra-heavy-heavy chain disulfide linkages (h 11, h 14) at 229-229" and 232-232"; N-glycosylation sites (H CH$_2$ N84.4) at 300, 300"; fucosylated complex bi-antennary CHO-type glycans; and H CHS K2 C-terminal lysine clipping at 450 and 450'.

In an embodiment, the anti-PD-L1 antibody is an anti-PD-L1 biosimilar monoclonal antibody approved by drug regulatory authorities with reference to avelumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is avelumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is avelumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab.

In an embodiment, anti-PD-L1 antibodies and other PD-L1 inhibitors include those described in U.S. Patent Application Publication No. 2014/0341917 A1, the disclosure of which is hereby incorporated by reference. In another embodiment, antibodies that compete with any of these antibodies for binding to PD-L1 are also included.

In an embodiment, the anti-PD-L1 antibody is MDX-1105, also known as BMS-935559, which is disclosed in U.S. Pat. No. 7,943,743 B2, the disclosures of which are specifically incorporated by reference herein. In an embodiment, the anti-PD-L1 antibody is selected from the anti-PD-L1 antibodies disclosed in U.S. Pat. No. 7,943,743 B2, which are specifically incorporated by reference herein.

In an embodiment, the anti-PD-L1 antibody is a commercially-available monoclonal antibody, such as INVIVOMAB anti-m-PD-L1 clone 10F.9G2 (Catalog #BE0101, Bio X Cell, Inc.). In an embodiment, the anti-PD-L1 antibody is a commercially-available monoclonal antibody, such as AFFYMETRIX EBIOSCIENCE (MIH1). A number of commercially-available anti-PD-L1 antibodies are known to one of ordinary skill in the art.

The anti-PD-L1 antibody sequences referenced in some of the foregoing embodiments are summarized in Table 2.

TABLE 2

Anti-PD-L1 antibody amino acid sequences.

| Identifier | Sequence (One-Letter Amino Acid Symbols) | |
|---|---|---|
| SEQ ID NO: 25 durvalumab (MEDI4736) heavy chain | EVQLVESGGG LVQPGGSLRL SCAASGFTFS RYWMSWVRQA PGKGLEWVAN IKQDGSEKYY VDSVKGRFTI SRDNAKNSLY LQMNSLRAED TAVYYCAREG GWFGELAFDY WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKRVE PKSCDKTHTC PPCPAPEFEG GPSVFLFPPK PKDTLMISRT PEVTCVWDV SHEDPEVKFN WYVDGVEVHN AKTKPREEQY NSTYRWSVL TVLHQDWLNG KEYKCKVSNK ALPASIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K | 60 120 180 240 300 360 420 451 |
| SEQ ID NO: 26 durvalumab (MEDI4736) light chain | EVQLVESGGG LVQPGGSLRL SCAASGFTFS RYWMSWVRQA PGKGLEWVAN EIVLTQSPGT LSLSPGERAT LSCRASQRVS SSYLAWYQQK PGQAPRLLIY DASSRATGIP DRFSGSGSGT DFTLTISRLE PEDFAVYYCQ QYGSLPWTFG QGTKVEIKRT VAAPSVFIFP PSDEQLKSGT ASWCLLNNF YPREAKVQWK VDNALQSGNS QESVTEQDSK DSTYSLSSTL TLSKADYEKH KVYACEVTHQ GLSSPVTKSF NRGEC | 60 120 180 240 265 |
| SEQ ID NO: 27 durvalumab variable heavy chain | EVQLVESGGG LVQPGGSLRL SCAASGFTFS RYWMSWVRQA PGKGLEWVAN IKQDGSEKYY VDSVKGRFTI SRDNAKNSLY LQMNSLRAED TAVYYCAREG GWFGELAFDY WGQGTLVTVS S | 60 120 121 |
| SEQ ID NO: 28 durvalumab variable light chain | EIVLTQSPGT LSLSPGERAT LSCRASQRVS SSYLAWYQQK PGQAPRLLIY DASSRATGIP DRFSGSGSGT DFTLTISRLE PEDFAVYYCQ QYGSLPWTFG QGTKVEIK | 60 108 |
| SEQ ID NO: 29 durvalumab heavy chain CDR1 | RYWMS | 5 |
| SEQ ID NO: 30 durvalumab heavy chain CDR2 | NIKQDGSEKY YVDSVKG | 17 |
| SEQ ID NO: 31 durvalumab heavy chain CDR3 | EGGWFGELAF DY | 12 |

TABLE 2-continued

Anti-PD-L1 antibody amino acid sequences.

| Identifier | Sequence (One-Letter Amino Acid Symbols) | |
|---|---|---|
| SEQ ID NO: 32 durvalumab light chain CDR1 | RASQRVSSSY LA | 12 |
| SEQ ID NO: 33 durvalumab light chain CDR2 | DASSRAT | 7 |
| SEQ ID NO: 34 durvalumab light chain CDR3 | QQYGSLPWT | 9 |
| SEQ ID NO: 35 atezolizumab (MPDL3280A) heavy chain | EVQLVESGGG LVQPGGSLRL SCAASGFTFS DSWIHWVRQA PGKGLEWVAW ISPYGGSTYY ADSVKGRFTI SADTSKNTAY LQMNSLRAED TAVYYCARRH WPGGFDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVWDVSHE DPEVKFNWYV DGVEVHNAKT KPREEQYAST YRWSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK | 60 120 180 240 300 360 420 448 |
| SEQ ID NO: 36 atezolizumab (MPDIA3280A) light chain | DIQMTQSPSS LSASVGDRVT ITCRASQDVS TAVAWYQQKP GKAPKLLIYS ASFLYSGVPS RFSGSGSGTD FTLTISSLQP EDFATYYCQQ YLYHPATFGQ GTKVEIKRTV AAPSVFIFPP SDEQLKSGTA SWCLLNNFY PREAKVQWKV DNALQSGNSQ ESVTEQDSKD STYSLSSTLT LSKADYEKHK VYACEVTHQG LSSPVTKSFN RGEC | 60 120 180 214 |
| SEQ ID NO: 37 atezolizumab variable heavy chain | EVQLVESGGG LVQPGGSLRL SCAASGFTFS DSWIHWVRQA PGKGLEWVAW ISPYGGSTYY ADSVKGRFTI SADTSKNTAY LQMNSLRAED TAVYYCARRH WPGGFDYWGQ GTLVTVSA | 60 118 |
| SEQ ID NO: 38 atezolizumab variable light chain | DIQMTQSPSS LSASVGDRVT ITCRASQDVS TAVAWYQQKP GKAPKLLIYS ASFLYSGVPS RFSGSGSGTD FTLTISSLQP EDFATYYCQQ YLYHPATFGQ GTKVEIKR | 60 108 |
| SEQ ID NO: 39 atezolizumab heavy chain CDR1 | GFTFSXSWIH | 10 |
| SEQ ID NO: 40 atezolizumab heavy chain CDR2 | AWIXPYGGSX YYADSVKG | 18 |
| SEQ ID NO: 41 atezolizumab heavy chain CDR3 | RHWPGGFDY | 9 |
| SEQ ID NO: 42 atezolizumab light chain CDR1 | RASQXXXTXX A | 11 |
| SEQ ID NO: 43 atezolizumab light chain CDR2 | SASXLXS | 7 |
| SEQ ID NO: 44 atezolizumab light chain CDR3 | QQXXXXPXT | 9 |
| SEQ ID NO: 45 avelumab (MSB00107180) heavy chain | EVQLLESGGG LVQPGGSLRL SCAASGFTFS SYIMMWVRQA PGKGLEWVSS IYPSGGITFY ADTVKGRFTI SRDNSKNTLY LQMNSLRAED TAVYYCARIK LGTVTTVDYW GQGTLVTVSS ASTKGPSVFP LAPSSKSTSG GTAALGCLVK DYFPEPVTVS WNSGALTSGV HTPPAVLQSS GLYSLSSWT VPSSSLGTQT YICNVNHKPS NTKVDKKVEP KSCDKTHTCP PCPAPELLGG PSVFLFPPKP KDTLMISRTP EVTCVWDVS HEDPEVKFNW YVDGVEVHNA KTKPREEQYN STYRWSVLT VLHQDWLNGK EYKCKVSNKA LPAPIEKTIS KAKGQPREPQ VYTLPPSRDE | 60 120 180 240 300 360 |

TABLE 2-continued

Anti-PD-L1 antibody amino acid sequences.

| Identifier | Sequence (One-Letter Amino Acid Symbols) | |
|---|---|---|
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 46 avelumab (MSB00107180) light chain | QSALTQPASV SGSPGQSITI SCTGTSSDVG GYNYVSWYQQ HPGKAPKLMI YDVSNRPSGV SNRFSGSKSG NTASLTISGL QAEDEADYYC SSYTSSSTRV FGTGTKVTVL GQPKANPTVT LFPPSSEELQ ANKATLVCLI SDFYPGAVTV AWKADGSPVK AGVETTKPSK QSNNKYAASS YLSLTPEQWK SHRSYSCQVT HEGSTVEKTV APTECS | 60 120 180 216 |
| SEQ ID NO: 47 avelumab variable heavy chain | EVQLLESGGG LVQPGGSLRL SCAASGFTFS SYIMMWVRQA PGKGLEWVSS IYPSGGITFY ADTVKGRFTI SRDNSKNTLY LQMNSLRAED TAVYYCARIK LGTVTTVDYW GQGTLVTVSS | 60 120 |
| SEQ ID NO: 48 avelumab variable light chain | QSALTQPASV SGSPGQSITI SCTGTSSDVG GYNYVSWYQQ HPGKAPKLMI YDVSNRPSGV SNRFSGSKSG NTASLTISGL QAEDEADYYC SSYTSSSTRV FGTGTKVTVL | 60 110 |
| SEQ ID NO: 49 avelumab heavy chain CDR1 | SYIMM | 5 |
| SEQ ID NO: 50 avelumab heavy chain CDR2 | SIYPSGGITF YADTVKG | 17 |
| SEQ ID NO: 51 avelumab heavy chain CDR3 | IKLGTVTTVD Y | 11 |
| SEQ ID NO: 52 avelumab light chain CDR1 | TGTSSDVGGY NYVS | 14 |
| SEQ ID NO: 53 avelumab light chain CDR2 | DVSNRPS | 7 |
| SEQ ID NO: 54 avelumab light chain CDR3 | SSYTSSSTRV | 10 |

The preparation, properties, and uses of suitable PD-1 and PD-L1 inhibitors are described in, e.g., U.S. Pat. No. 8,008,449 or U.S. Patent Application Publication Nos. 2009/0217401 A1 or 2013/0133091 A1; U.S. Pat. No. 8,354,509 and U.S. Patent Application Publication Nos. 2010/0266617 A1, 2013/0108651 A1, and 2013/0109843 A2; U.S. Pat. Nos. 8,287,856, 8,580,247, and 8,168,757 and U.S. Patent Application Publication Nos. US 2009/0028857 A1, US 2010/0285013 A1, US 2013/0022600 A1, and US 2011/0008369 A1; U.S. Pat. No. 8,779,108 or U.S. Patent Application Publication No. 2013/0034559 A1; U.S. Pat. No. 8,217,149 and U.S. Patent Application Publication Nos. 2010/0203056 A1, 2013/0045200 A1, 2013/0045201 A1, 2013/0045202 A1, or 2014/0065135 A1; and U.S. Patent Application Publication No. 2014/0341917 A1, the disclosures of each of which are incorporated by reference herein.

In an embodiment, a PD-1 or PD-L1 inhibitor selected from the group consisting of nivolimumab, pembrolizumab, pidilizumab, durvalumab, atezolizumab, avelumab, and/or Fab fragments, antigen-binding fragments, derivatives, conjugates, variants, and radioisotope-labeled complexes thereof, is administered to a subject by infusing a dose selected from the group consisting of about 10 mg, about 20 mg, about 25 mg, about 50 mg, about 75 mg, 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, and about 2000 mg. In an embodiment, the PD-1 or PD-L1 inhibitor is administered weekly. In an embodiment, the PD-1 or PD-L1 inhibitor is administered every two weeks. In an embodiment, the PD-1 or PD-L1 inhibitor is administered every three weeks. In an embodiment, the PD-1 or PD-L1 inhibitor is administered monthly. In an embodiment, the PD-1 or PD-L1 inhibitor is administered at a lower initial dose, which is escalated when administered at subsequent intervals administered monthly.

Other Immunotherapeutic Agents

In some embodiments, the methods and/or compositions described herein include a combination of an HDAC inhibitor (e.g., a selective HDAC inhibitor) and one or more immunotherapeutic agents. In some embodiments, the immunotherapeutic agents may include one or more of rituximab (Rituxan®; SEQ ID NO.55 (heavy chain) and SEQ ID NO.56 (light chain)), trastuzumab (Herceptin®; SEQ ID NO.57 (heavy chain) and SEQ ID NO.58 (light chain)), ibritumomab (Zevalin®; SEQ ID NO.59 (heavy chain) and SEQ ID NO.60 (light chain)), tositumomab (Bexxar®; SEQ ID NO.61 (heavy chain) and SEQ ID NO.62 (light chain)), cetuximab (C-225, Erbitux®; SEQ ID NO.63 (heavy chain) and SEQ ID NO.64 (light chain)), bevacizumab (Avastin®; SEQ ID NO.65 (heavy chain) and SEQ ID NO.66 (light chain)), gemtuzumab (Mylotarg®; SEQ ID NO.67 (heavy chain) and SEQ ID NO.68 (light chain)), alemtuzumab (Campath®; SEQ ID NO.69 (heavy chain) and SEQ ID NO.70 (light chain)), and BL22 (RFB4 (dsFv)-PE38 or CAT-3888, and as described in Mansfield, et al., *Blood* (1997) 90: 2020-2026 and Kreitman, et al., *Clin Cancer Res*. (2011) 17: 6398-6405).

In an embodiment, the immunotherapeutic agent comprises one or more of rituximab, trastuzumab, ibritumomab, tositumomab, cetuximab, bevacizumab, gemtuzumab, alemtuzumab, and BL22, or a biosimilar, antigen-binding fragment, derivative, conjugate, variant, or radioisotope-labeled complex thereof.

In an embodiment, the forementioned immunotherapeutic agents may be provided in a pharmaceutical composition or method, as described herein, as a biosimilar monoclonal antibody approved by drug regulatory authorities with reference to rituximab, trastuzumab, ibritumomab, tositumomab, cetuximab, bevacizumab, gemtuzumab, alemtuzumab, or BL22. In an embodiment, the biosimilar comprises a monoclonal antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is rituximab, trastuzumab, ibritumomab, tositumomab, cetuximab, bevacizumab, gemtuzumab, alemtuzumab, or BL22. In some embodiments, the one or more post-translational modifications are selected from one or more of: glycosylation, oxidation, deamidation, and truncation. In some embodiments, the biosimilar is an monoclonal antibody authorized or submitted for authorization, wherein the monoclonal antibody is provided in a formulation which differs from the formulations of a reference medicinal product or reference biological product, wherein the reference medicinal product or reference biological product is rituximab, trastuzumab, ibritumomab, tositumomab, cetuximab, bevacizumab, gemtuzumab, alemtuzumab, or BL22. The monoclonal antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is rituximab, trastuzumab, ibritumomab, tositumomab, cetuximab, bevacizumab, gemtuzumab, alemtuzumab, or BL22. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is rituximab, trastuzumab, ibritumomab, tositumomab, cetuximab, bevacizumab, gemtuzumab, alemtuzumab, or BL22.

In an embodiment, a monoclonal antibody selected from the group consisting of rituximab, trastuzumab, ibritumomab, tositumomab, cetuximab, bevacizumab, gemtuzumab, alemtuzumab, and BL22, and/or biosimilars, antigen-binding fragments, derivatives, conjugates, variants, and radioisotope-labeled complexes thereof, is administered to a subject by infusing a dose selected from the group consisting of about 10 mg, about 20 mg, about 25 mg, about 50 mg, about 75 mg, 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, and about 2000 mg. In an embodiment, the monoclonal antibody is administered weekly. In an embodiment, the monoclonal antibody is administered every two weeks. In an embodiment, the monoclonal antibody is administered every three weeks. In an embodiment, the monoclonal antibody is administered monthly. In an embodiment, the monoclonal antibody is administered at a lower initial dose, which is escalated when administered at subsequent intervals administered monthly Several of the other immunotherapeutic agent sequences referenced in the foregoing sections are summarized in Table 3.

TABLE 3

Other immunotherapeutic agent antibody sequences.

| Sequence Identifier and Description | Sequence (One-Letter Amino Acid Symbols) | |
|---|---|---|
| SEQ ID NO: 55 rituximab heavy chain | QVQLQQPGAE LVKPGASVKM SCKASGYTFT SYNMHWVKQT PGRGLEWIGA IYPGNGDTSY | 60 |
| | NQKFKGKATL TADKSSSTAY MQLSSLTSED SAVYYCARST YYGGDWYFNV WGAGTTVTVS | 120 |
| | AASTKGPSVF PLAPSSKSTS GGTAALGCLV KDYFPEPVTV SWNSGALTSG VHTFPAVLQS | 180 |
| | SGLYSLSSW TVPSSSLGTQ TYICNVNHKP SNTKVDKKVE PKSCDKTHTC PPCPAPELLG | 240 |
| | GPSVFLFPPK PKDTLMISRT PEVTCVWDV SHEDPEVKFN WYVDGVEVHN AKTKPREEQY | 300 |
| | NSTYRWSVL TVLHQDWLNG KEYKCKVSNK ALPAPIEKTI SKAKGQPREP QVYTLPPSRD | 360 |
| | ELTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 56 rituximab light chain | QIVLSQSPAI LSASPGEKVT MTCRASSSVS YIHWFQQKPG SSPKPWIYAT SNLASGVPVR | 60 |
| | FSGSGSGTSY SLTISRVEAE DAATYYCQQW TSNPPTFGGG TKLEIKRTVA APSVFIFPPS | 120 |
| | DEQLKSGTAS WCLLNNFYP REAKVQWKVD NALQSGNSQE SVTEQDSKDS TYSLSSTLTL | 180 |
| | SKADYEKHKV YACEVTHQGL SSPVTKSFNR GEC | 213 |

TABLE 3-continued

Other immunotherapeutic agent antibody sequences.

| Sequence Identifier and Description | Sequence (One-Letter Amino Acid Symbols) | |
|---|---|---|
| SEQ ID NO: 57 trastuzumab heavy chain | EVQLVESGGG LVQPGGSLRL SCAASGFNIK DTYIHWVRQA PGKGLEWVAR IYPTNGYTRY | 60 |
| | ADSVKGRFTI SADTSKNTAY LQMNSLRAED TAVYYCSRWG GDGFYAMDYW GQGTLVTVSS | 120 |
| | ASTKGPSVFP LAPSSKSTSG GTAALGCLVK DYFPEPVTVS WNSGALTSGV HTFPAVLQSS | 180 |
| | GLYSLSSWT VPSSSLGTQT YICNVNHKPS NTKVDKKVEP PKSCDKTHTC PPCPAPELLG | 240 |
| | GPSVFLFPPK PKDTLMISRT PEVTCVWDV SHEDPEVKFN WYVDGVEVHN AKTKPREEQY | 300 |
| | NSTYRWSVL TVLHQDWLNG KEYKCKVSNK ALPAPIEKTI SKAKGQPREP QVYTLPPSRD | 360 |
| | ELTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 58 trastuzumab light chain | DIQMTQSPSS LSASVGDRVT ITCRASQDVN TAVAWYQQKP GKAPKLLIYS ASFLYSGVPS | 60 |
| | RFSGSRSGTD FTLTISSLQP EDFATYYCQQ HYTTPPTFGQ GTKVEIKRTV AAPSVFIFPP | 120 |
| | SDEQLKSGTA SWCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 59 ibritumomab heavy chain | QAYLQQSGAE LVRPGASVKM SCKASGYTFT SYNMHWVKQT PRQGLEWIGA IYPGNGDTSY | 60 |
| | NQKFKGKATL TVDKSSSTAY MQLSSLTSED SAVYFCARW YYSNSYWYFD VWGTGTTVTV | 120 |
| | SAPSVYPLAP VCGDTTGSSV TLGCLVKGYF PEPVTLTWNS GSLSSGVHTF PAVLQSDLYT | 180 |
| | LSSSVTVTSS TWPSQSITCN VAHPASSTKV DKKIEPRGPT IKPCPPCKCP APNLLGGPSV | 240 |
| | FIFPPKIKDV LMISLSPIVT CVWDVSEDD PDVQISWFVN NVEVHTAQTQ THREDYNSTL | 300 |
| | RWSALPIQH QDWMSGKEFK CKVNNKDLPA PIERTISKPK GSVRAPQVYV LPPPEEEMTK | 360 |
| | KQVTLTCMVT DFMPEDIYVE WTNNGKTELN YKNTEPVLDS DGSYFMYSKL RVEKKNWVER | 420 |
| | NSYSCSWHE GLHNHHTTKS FSR | 443 |
| SEQ ID NO: 60 ibritumomab light chain | QIVLSQSPAI LSASPGEKVT MTCRASSSVS YMHWYQQKPG SSPKPWIYAP SNLASGVPAR | 60 |
| | FSGSGSGTSY SLTISRVEAE DAATYYCQQW SFNPPTFGAG TKLELKRADA APTVFIFPPS | 120 |
| | DEQLKSGTAS WCLLNNFYP REAKVQWKVD NALQSGNSQE SVTEQDSKDS TYSLSSTLTL | 180 |
| | SKADYEKHKV YACEVTHQGL SSPVTKSFN | 209 |
| SEQ ID NO: 61 tositumomab heavy chain | QAYLQQSGAE LVRPGASVKM SCKASGYTFT SYNMHWVKQT PRQGLEWIGA IYPGNGDTSY | 60 |
| | NQKFKGKATL TVDKSSSTAY MQLSSLTSED SAVYFCARW YYSNSYWYFD VWGTGTTVTV | 120 |
| | SGPSVFPLAP SSKSTSGGTA ALGCLVKDYF PEPVTVSWNS GALTSGVHTF PAVLQSSGLY | 180 |
| | SLSSWTVPS SSLGTQTYIC NVNHKPSNTK VDKKAEPKSC DKTHTCPPCP APELLGGPSV | 240 |
| | FLFPPKPKDT LMISRTPEVT CVWDVSHED PEVKFNWYVD GVEVHNAKTK PREEQYNSTY | 300 |
| | RWSVLTVLH QDWLNGKEYK CKVSNKALPA PIEKTISKAK GQPREPQVYT LPPSRDELTK | 360 |
| | NQVSLTCLVK GFYPSDIAVE WESNGQPENN YKTTPPVLDS DGSFFLYSKL TVDKSRWQQG | 420 |
| | NVFSCSVMHE ALHNHYTQKS LSLSPGK | 447 |
| SEQ ID NO: 62 tositumomab light chain | QIVLSQSPAI LSASPGEKVT MTCRASSSVS YMHWYQQKPG SSPKPWIYAP SNLASGVPAR | 60 |
| | FSGSGSGTSY SLTISRVEAE DAATYYCQQW SFNPPTFGAG TKLELKRTVA APSVFIFPPS | 120 |
| | DEQLKSGTAS WCLLNNFYP REAKVQWKVD NALQSGNSQE SVTEQDSKDS TYSLSSTLTL | 180 |
| | SKADYEKHKV YACEVTHQGL SSPVTKSFNR | 210 |
| SEQ ID NO: 63 cetuximab heavy chain | QVQLKQSGPG LVQPSQSLSI TCTVSGFSLT NYGVHWVRQS PGKGLEWLGV IWSGGNTDYN | 60 |
| | TPFTSRLSIN KDNSKSQVFF KMNSLQSNDT AIYYCARALT YYDYEFAYWG QGTLVTVSAA | 120 |
| | STKGPSVFPL APSSKSTSGG TAALGCLVKD YFPEPVTVSW NSGALTSGVH TFPAVLQSSG | 180 |
| | LYSLSSWTV PSSSLGTQTY ICNVNHKPSN TKVDKRVEPK SPKSCDKTHT CPPCPAPELL | 240 |
| | GGPSVFLFPP KPKDTLMISR TPEVTCVWD VSHEDPEVQ FNWYVDGVEV HNAKTKPREEQ | 300 |
| | YNSTYRWSV LTVLHQDWLN GKEYKCKVSN KALPAPIEKT ISKAKGQPRE PQVYTLPPSR | 360 |
| | DELTKNQVSL TCLVKGFYPS DIAVEWESNG QPENNYKTTP PVLDSDGSFF LYSKLTVDKS | 420 |
| | RWQQGNVFSC SVMHEALHNH YTQKSLSLSP GK | 452 |
| SEQ ID NO: 64 cetuximab light chain | DILLTQSPVI LSVSPGERVS FSCRASQSIG TNIHWYQQRT NGSPRLLIKY ASESISGIPS | 60 |
| | RFSGSGSGTD FTLSINSVES EDIADYYCQQ NNNWPTTFGA GTKLELKRTV AAPSVFIFPP | 120 |
| | SDEQLKSGTA SWCLLNNFY PREAKVQWKV DNALQSGNSQ ESVTEQDSKD STYSLSSTLT | 180 |
| | LSKADYEKHK VYACEVTHQG LSSPVTKSFN RGA | 213 |
| SEQ ID NO: 65 bevacizumab heavy chain | EVQLVESGGG LVQPGGSLRL SCAASGYTFT NYGMNWVRQA PGKGLEWVGW INTYTGEPTY | 60 |
| | AADFKRRFTF SLDTSKSTAY LQMNSLRAED TAVYYCAKYP HYYGSSHWYF DVWGQGTLVT | 120 |
| | VSSASTKGPS VFPLAPSSKS TSGGTAALGC LVKDYFPEPV TVSWNSGALT SGVHTFPAVL | 180 |
| | QSSGLYSLSS WTVPSSSLG TQTYICNVNH KPSNTKVDKK TCPPCPAPEL LGGPSVFLFP | 240 |
| | LGGPSVFLFP PKPKDTLMIS RTPEVTCVW DVSHEDPEVK FNWYVDGVEV HNAKTKPREE | 300 |
| | QYNSTYRWS VLTVLHQDWL NGKEYKCKVS NKALPAPIEK TISKAKGQPR EPQVYTLPPS | 360 |
| | REEMTKNQVS LTCLVKGFYP SDIAVEWESN GQPENNYKTT PPVLDSDGSF FLYSKLTVDK | 420 |
| | SRWQQGNVFS CSVMHEALHN HYTQKSLSLS PGK | 453 |
| SEQ ID NO: 66 bevacizumab Light chain | DIQMTQSPSS LSASVGDRVT ITCSASQDIS NYLNWYQQKP GKAPKVLIYF TSSLHSGVPS | 60 |
| | RFSGSGSGTD FTLTISSLQP EDFATYYCQQ YSTVPWTFGQ GTKVEIKRTV AAPSVFIFPP | 120 |
| | SDEQLKSGTA SWCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 67 gemtuzumab heavy chain | QVQLQQSGAE LAKPGASVKM SCKASGYTFT SYRMHWVKQR PGQGLEWIGY INPSTGYTEY | 60 |
| | NQKFKDKATL TADKSSSTAY MQLSSLTFED SAVYYCARGG GVFDYWGQGT TLTVSS | 116 |

TABLE 3-continued

Other immunotherapeutic agent antibody sequences.

| Sequence Identifier and Description | Sequence (One-Letter Amino Acid Symbols) | |
|---|---|---|
| SEQ ID NO: 68 gemtuzumab Light chain | QIVLTQSPAI MSASPGEKVT ITCSASSSIS YMHWFQQKPG TSPKLWIYTT SNLASGVPAR<br>FSGSGSGTSY SLTISRMEAE DAATYYCHQR STYPLTFGSG TKLELK | 60<br>106 |
| SEQ ID NO: 69 alemtuzumab heavy chain | QVQLQESGPG LVRPSQTLSL TCTVSGFTFT DFYMNWVRQP PGRGLEWIGF IRDKAKGYTT<br>EYNPSVKGRV TMLVDTSKNQ FSLRLSSVTA ADTAVYYCAR EGHTAAPFDY WGQGSLVTVS<br>SASTKGPSVF PLAPSSKSTS GGTAALGCLV KDYFPEPVTV SWNSGALTSG VHTFPAVLQS<br>SGLYSLSSW TVPSSSLGTQ TYICNVNHKP SNTKVDKKVE PKSCDKTHTC PPCPAPELLG<br>GPSVFLFPPK PKDTLMISRT PEVTCVWDV SHEDPEVKFN WYVDGVEVHN AKTKPREEQY<br>NSTYRWSVL TVLHQDWLNG KEYKCKVSNK ALPAPIEKTI SKAKGQPREP QVYTLPPSRD<br>ELTKNQVSLT CLVKGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 70 alemtuzumab Light chain | DIQMTQSPSS LSASVGDRVT ITCKASQNID KYLNWYQQKP GKAPKLLIYN TNNLQTGVPS<br>RFSGSGSGTD FTFTISSLQP EDIATYYCLQ HISRPRTFGQ GTKVEIKRTV AAPSVFIFPP<br>SDEQLKSGTA SWCLLNNFY PREAKVQWKV DNALQSGNSQ ESVTEQDSKD STYSLSSTLT<br>LSKADYEKHK VYACEVTHQG LSSPVTKSFN R | 60<br>120<br>180<br>211 |

Methods of Treating Cancer

Cancer is the second leading cause of death in the United States after heart disease. The American Cancer Society estimates that 1,665,540 new cancer cases are expected to have been diagnosed in 2014 with 585,720 cancer-related deaths.

In some embodiments, the invention includes methods of treating a disease alleviated by inhibiting histone deacetylase (HDAC) protein in a patient in need thereof, wherein the treatment includes the step of administering a therapeutically effective amount of one or more HDAC inhibitors described herein (e.g., one or more HDAC inhibitors described by Formulas Ia, Ib, II, and/or III. In some embodiments, the disease is cancer. For example, the cancer may be one of the cancers described in Table 4.

In some embodiments, the one or more HDAC inhibitors may include HDAC inhibitors that selectively inhibit HDAC 6. For example, the HDAC inhibitors used in the methods of the invention may include

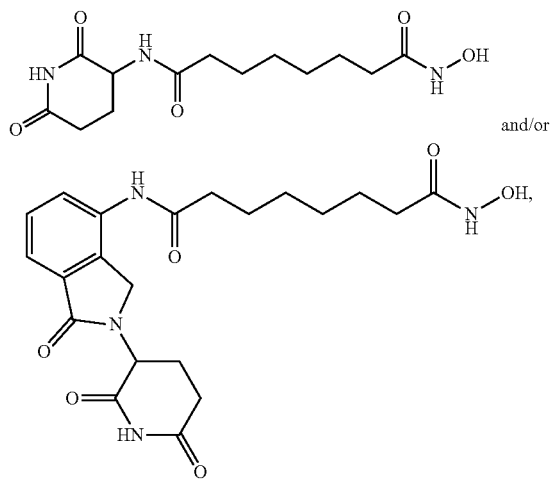

or a pharmaceutically acceptable salt, solvate, hydrate, cocrystal, or prodrug thereof.

In some embodiments, the methods of the invention may include administering a therapeutically effective amount of an additional therapeutic agent such as, for example, chemotherapeutic agents and/or immunotherapeutic agents, as described herein.

In some embodiments, a patient responding to the methods of treatment disclosed herein may exhibit the absence of disease progression (e.g., halting the growth and/or spread of neoplastic cells and tissues) over another patient that does not receive the methods of treatment described herein.

In some embodiments, the cancer treated by the methods and/or compositions described herein may include those cancers listed in Table 4.

TABLE 4

Selected cancers that may be treated by the methods of the invention.

Exemplary Solid Tumors:

acoustic neuroma
adenocarcinoma
angiosarcoma
astrocytoma
basal cell carcinoma
bile duct carcinoma
bladder carcinoma
breast cancer
bronchogenic carcinoma
cervical cancer
chordoma
choriocarcinoma
colon cancer
colorectal cancer
craniopharygioma
cystadenocarcinoma
embryonal carcinoma
endotheliosarcoma
ependymoma
epithelial carcinoma
esophagael cancer
Ewing's tumor
fibrosarcoma
glioblastomamultiforme
glioma
hemangioblastoma
hepatoma TABLE 4-continued Selected cancers that may be treated by the methods of the invention.

kidney cancer
leiomyosarcoma
liposarcoma
lung cancer
lymphangioendotheliosarcoma
lymphangiosarcoma
medullary carcinoma
medulloblastoma
melanoma
meningioma
mesothelioma
myxosarcoma
nasal cancer
neuroblastoma
oligodendroglioma
oral cancer
osteogenic sarcoma
ovarian cancer
pancreatic cancer
papillary adenocarcinomas
papillary carcinoma
pinealoma
prostate cancer
rabdomyosarcoma
renal cell carcinoma
retinoblastoma
sebaceous gland carcinoma
seminoma
skin cancer
squamous cell carcinoma
stomach cancer
sweat gland carcinoma
synovioma
testicular cancer small cell lung carcinoma
throat cancer
uterine cancer
Wilms' tumor Exemplary Blood Cancers:

acute erythroleukemic leukemia
acute lymphoblastic B-cell leukemia
acute lymphoblastic T-cell leukemia
acute lypmhoblastic leukemia
acute megakaryoblastic leukemia
acute monoblastic leukemia
acute myeloblastic leukemia
acute myelomonocytic leukemia
acute nonlymphocytic leukemia
acute promyelocytic leukemia
acute undifferentiated leukemia
chronic lymphocytic leukemia
chronic myelocytic leukemia
hairy cell leukemia
multiple myeloma Exemplary Lymphomas:

heavy chain disease
Hodgkin's disease
multiple myeloma
non-Hodgkin's lymphoma
polycythemia vera
Waldenstrom's macroglobulinemia In some embodiments, the cancers described herein that may be treated by the methods of the invention may be treated with or without a further step of irradiation.

In some embodiments, the cancer treated by the methods of the invention may include acoustic neuroma, adenocarcinoma, angiosarcoma, astrocytoma, basal cell carcinoma, bile duct carcinoma, bladder carcinoma, brain cancer, breast cancer, brochogenic carcinoma, cervical cancer, chordoma, choriocarcinoma, colon cancer, colorectal cancer, craniopharygioma, cystadenocarcinoma, embryonal carcinoma, endotheliocarconima, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebacaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, and Waldenstrom's macroglobulinemia.

In some embodiments, the cancers treated by the methods and/or compositions of the invention are HPV positive (+) cancers. HPV (+) cancers may include cervical cancer and head and neck cancer.

In some embodiments, treatments of cancer may include surgery, radiotherapy, and/or chemotherapy. Each treatment modality carries risks and benefits, and cancer recurrences underlie efforts to improve the outcomes of treatment. In particular, recent advances in surgical and radiation therapy technologies, employing computational and robotic methods, have plateaued efficacy of local-regional treatments. Moreover, targeted agents to personalize chemotherapy have altered the cancer treatment paradigm.

Radiation therapy (i.e., radiotherapy) involves the treatment of cancer and other diseases using ionizing radiation. Ionizing radiation deposits energy that injures or destroys cells in targeted tissues by damaging their genetic material and subsequently interfering with a cell's ability to grow and/or replicate. Radiation exposure damages cancer cells and normal cells, but the normal cells activate processes to better repair themselves and may continue to function properly. Radiotherapy may be used to treat solid tumors (e.g., cancers of the head and neck, breast, prostate, rectum, uterus, lung, brain, kidney, uterus, and cervix). Radiotherapy may also be used to treat cancers such as leukemias and lymphomas. Radiotherapies used for leukemias and lymphomas may include total body radiation therapy in protocols preparing patients for bone marrow transplants. Radiotherapy may be more effective when the targeted cancer tissues are more sensitive to the effects of radiation than surrounding normal tissues.

The radiation responses of different cancers or tumors may vary as a function of histology, cellular doubling time, oxygenation, nutrient availability, repair capacity, and other factors. Some cancers are readily cured using ionizing radiation doses within normal tissue tolerances, while other types of cancer may not be very responsive to radiation. Furthermore, radiation responses of tumors with the same histology may show considerable heterogeneity and reduce the therapeutic effects of the therapy. Thus, a primary challenge facing radiotherapy is the differentiation between the more radiosensitive tumors versus less radiosensitive tumors and the surrounding healthy tissues.

Investigations into the molecular bases underlying cellular radiation responses have provided dramatic mechanistic insight. Signal transduction pathways have been implicated to play important roles in cellular responses to ionizing radiation. Induction of gene expression by these cascades under various conditions has been shown to result in cell cycle arrest, activation of DNA repair processes, and activation of programmed cell death (apoptosis). Disruption of critical signaling pathways in cancer cells may result in enhanced cytotoxic effects following radiation exposure. Certain cells may be disrupted by interfering with the histone acetylation and deacetylation processes of the cells.

Therapeutic ratios may be determined by measuring the effects of drugs on cancers and on normal tissues. Radiation toxicities to organs at risk may affect normal tissues adjacent to the treated volume (such as rectum or bladder in the treatment of a pelvic tumor), or in sites receiving transit dose (such as the pelvic bone marrow).

The methods of the invention may include irradiating a selected tissue of the patient before, during, and/or after a compound of the invention (or pharmaceutical composition containing such compound) is administered to the patient. Regarding the application of radiation ("radiation therapy" or "radiotherapy") to the patient or subject more generally, such therapy may encompass any ionizing radiation known to those having ordinary skill in the art. Generally, radiation therapy, and in particular ionizing radiation includes applying to a selected tissue, such as a selected tissue comprising cancerous and/or neoplastic cells, a dose of ionizing radiation or two or more fractions of ionizing radiation. The ionization radiation is defined as an irradiation dose which is determined according to the disease's characteristics at the selected tissue and therapeutic decision of a physician. The term "fractionated dose(s)" may include, for example, conventional fractionation, hyperfractionation, hypofractionation, and accelerated fractionation). The amount of radiation and doses thereof should be sufficient to damage the highly proliferating cells' genetic material, making it impossible for the irradiated cells to continue growing and dividing.

In certain aspects, fractionated irradiation may vary from daily doses (e.g. one or more times per day) given for a period of weeks, or to once weekly doses given for a period of weeks or months. Indeed, radiation may be applied in dosages of about 0.1 Gy to about 100 Gy. For example, the dosage may be about 5 to 15 Gy.

In certain fractionated irradiation methods, irradiation dosing may include the application of about 0.1 to about 20 Gy or from about 1 Gy to about 10 Gy or from about 1 Gy to about 3 Gy in a single session, which may be repeated several times over the course of about 1 to 10 weeks, or about 2 to 5 weeks. In certain embodiments of the invention, the radiation dose may be about 30 to 60 Gy at 1 to 5 Gy fractions over a period of about 2 to 5 weeks.

In other exemplary aspects, three different fractionation schemes may be used in accordance with the invention.

In one embodiment, radiation doses from 1 Gy to 3 Gy in daily fractions for several weeks (e.g., about 2 to 8 weeks) to achieve cumulative doses of about 20 Gy to 80 Gy.

In another embodiment, large fraction radiation therapy may include doses of 4 Gy to 25 Gy. This fractionated irradiation scheme may include the delivery of about 1 fraction to 5 fractions delivered over about 1-2 weeks. This type of radiation may be referred to as stereotactic radiosurgery or stereotactic body radiation therapy.

In a further embodiment, brachytherapy may be used, which is delivered using low dose and rate techniques or high-dose rate techniques, typically delivering doses of about 4 Gy to 10 Gy per day with technique and fractionation specific to the clinical situation as would be understood by a person having ordinary skill in the art.

As set forth above, the compounds and/or compositions of the invention may be administered before, after, or together with the radiation. One cycle of radiation therapy as well as several cycles of radiation is possible, dependent on the reduction of tumor size or extent of proliferation. Such sequences of radiosensitization treatments and ionizing irradiation are repeated as needed to abate and, optimally, reduce or eliminate the spread of the cancer or neoplastic cells in the tissue or region of tissue that is selected for treatment. Accordingly, the total dose and the radiation regimen will depend, inter alia, on the cancer type, type of compound that results in radiosensitization, irradiated area, physical condition of the patient and many other considerations appreciated by those having ordinary skill in the art.

In addition to the administration of a compound of the invention and the irradiation of the patient, the methods of the invention may include the administration of a therapeutically effective amount of a chemotherapeutic agent and/or an immunotherapeutic agent to the patient. The chemotherapeutic agent and/or immunotherapeutic agent may be provided before, during, or after at least one of the steps of administering the HDAC inhibitor and irradiating a selected tissue of the patient. Therefore, the chemotherapeutic agent and/or immunotherapeutic agent may be provided at various points during the methods of the invention for the treatment of disease. In certain aspects, the chemotherapeutic agent and/or immunotherapeutic agent may be administered concurrently with or after the step of irradiating the selected tissue of the patient.

Methods of Treating Immunological Diseases

Regarding immunological diseases, the HDAC inhibitors may be used in methods of treating diseases that are the result of over-active immunity. Millions of people worldwide endure debilitating immunological diseases that implicate HDAC proteins and may be treated by the compounds, compositions, and methods of the invention. For example, see International Patent Application No. 2011/017448, the entirety of which is incorporated herein by reference.

In some embodiments, the invention includes methods of treating a disease alleviated by inhibiting histone deacetylase (HDAC) protein in a patient in need thereof, wherein the treatment includes the step of administering a therapeutically effective amount of one or more HDAC inhibitors described herein. In some embodiments, the disease is an immunological disease, as described herein.

In some embodiments, the immunological disease may be celiac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, rheumatoid arthritis (RA), polymyositis, ulcerative colitis, Crohn's disease, autoimmune carditis, Wegener's granulomatosis, autoimmune hemolytic anemia, polyarteritis nodosa, psoriasis, vitiligo, epidermolysis bullosa, scleroderma, alopecia areata, epidermolysis bullosa acquisita, bullous pemphigoid, pemphigus foliaceous, and pemphigus vulgaris.

In some embodiments, the one or more HDAC inhibitors may include HDAC inhibitors that selectively inhibit HDAC 6. For example, the HDAC inhibitors used in the methods of the invention may include

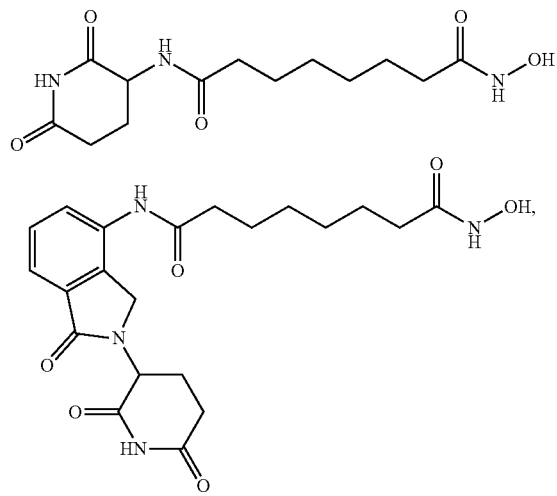

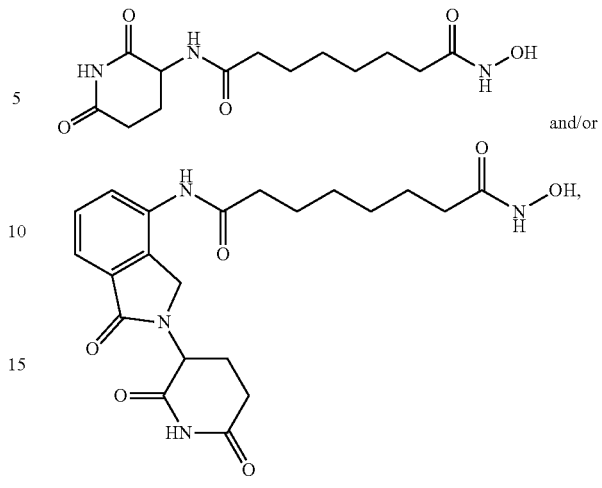

or a pharmaceutically acceptable salt, solvate, hydrate, cocrystal, or prodrug thereof.

In some embodiments, the methods of the invention may include administering a therapeutically effective amount of an additional therapeutic agent such as, for example, chemotherapeutic agents and/or immunotherapeutic agents, as described herein.

Methods of Treating Neurological Diseases

Neurological diseases affect a vast number of humans of all ages. In the United States, over 500,000 people each year experience a stroke, making it the third leading cause of death and the primary cause of disability. One in twenty people is afflicted with Alzheimer's disease by the age of 65, and almost 40 percent of the population have the disease by age 80. More than 600,000 people suffer from Parkinson's disease and over 200,000 from multiple sclerosis. Every year, greater than 10,000 people die from amyotrophic lateral sclerosis (ALS). The impact of neurological disease is not only devastating for the patients, but also for their families.

Although considerable effort has been invested in the design of effective therapies, neurological diseases continue to threaten the worldwide population and lessen their quality of life. The HDAC inhibitors may be used in compositions or methods for treating such neurological disorders that implicate HDAC proteins.

In some embodiments, the invention includes methods of treating a disease alleviated by inhibiting histone deacetylase (HDAC) protein in a patient in need thereof, wherein the treatment includes the step of administering a therapeutically effective amount of one or more HDAC inhibitors described herein. In some embodiments, the disease is a neurological disease, as described herein.

In some embodiments, the neurological disease may be selected from the group consisting of Huntington's disease, spinal muscular atrophy (SMA), Parkinson's disease, Alzheimer's, Multiple Sclerosis, and Amyotrophic Lateral Sclerosis (ALS). In certain aspects, the neurological disease may be Alzheimer's disease or multiple sclerosis.

In some embodiments, the one or more HDAC inhibitors may include HDAC inhibitors that selectively inhibit HDAC6. For example, the HDAC inhibitors used in the methods of the invention may include or a pharmaceutically acceptable salt, solvate, hydrate, cocrystal, or prodrug thereof.

In some embodiments, the methods of the invention may include administering a therapeutically effective amount of an additional therapeutic agent such as, for example, chemotherapeutic agents and/or immunotherapeutic agents, as described herein.

Methods of Treating Inflammatory Diseases

Compounds having a hydroxamic acid moiety are known to possess useful biological activities in addition to being useful for treating cancer, immunological diseases, and neurological diseases. For example, many peptidyl compounds possessing a hydroxamic acid moiety are known to inhibit matrix metalloproteinases (MMPs), which are a family of zinc endopeptidases. The MMPs play a key role in both physiological and pathological tissue degradation. Therefore, peptidyl compounds that have the ability to inhibit the action of MMPs show utility for the treatment or prophylaxis of conditions involving tissue breakdown and inflammation.

In some embodiments, the invention includes methods of treating a disease alleviated by inhibiting histone deacetylase (HDAC) protein in a patient in need thereof, wherein the treatment includes the step of administering a therapeutically effective amount of one or more HDAC inhibitors described herein. In some embodiments, the disease is an inflammatory disease, as described herein.

In some embodiments, the inflammatory diseases may include, for example, psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; acute pancreatitis; inflammatory bowel disease; or an inflammatory condition resulting from strain, sprain, cartilage damage, trauma such as burn, orthopedic surgery, infection or other disease processes. See, for example, U.S. Pat. No. 7,507,858.

In some embodiments, the one or more HDAC inhibitors may include HDAC inhibitors that selectively inhibit HDAC6. For example, the HDAC inhibitors used in the methods of the invention may include

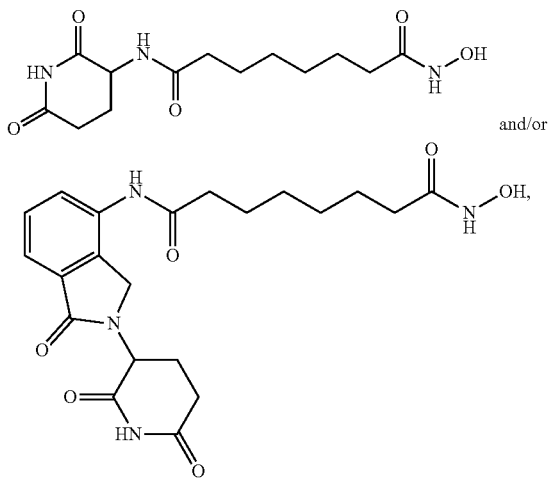

or a pharmaceutically acceptable salt, solvate, hydrate, cocrystal, or prodrug thereof.

In some embodiments, the methods of the invention may include administering a therapeutically effective amount of an additional therapeutic agent such as, for example, chemotherapeutic agents and/or immunotherapeutic agents, as described herein.

Pharmaceutical Compositions

In an embodiment, an active pharmaceutical ingredient or combination of active pharmaceutical ingredients, such as any of the foregoing HDAC inhibitors (e.g., HDAC6 inhibitors), is provided as a pharmaceutically acceptable composition.

In some embodiments, the concentration of each of the active pharmaceutical ingredients provided in the pharmaceutical compositions of the invention, such as any of the foregoing HDAC inhibitors, is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%1, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of each of the active pharmaceutical ingredients provided in the pharmaceutical compositions of the invention, such as any of the foregoing HDAC inhibitors, is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the foregoing HDAC inhibitors, is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of each of the active pharmaceutical ingredients provided in the pharmaceutical compositions of the invention, such as any of the foregoing HDAC inhibitors, is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of each of the active pharmaceutical ingredients provided in the pharmaceutical compositions of the invention, such as any of the foregoing HDAC inhibitors, is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the active pharmaceutical ingredients provided in the pharmaceutical compositions of the invention, such as any of the foregoing HDAC inhibitors, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician. The clinically-established dosages of the foregoing HDAC inhibitors may also be used if appropriate.

In an embodiment, the molar ratio of two active pharmaceutical ingredients in the pharmaceutical compositions is in the range from 10:1 to 1:10, preferably from 2.5:1 to 1:2.5, and more preferably about 1:1. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20.

Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

Furthermore, the described methods of treatment may normally include medical follow-up to determine the therapeutic or prophylactic effect brought about in the subject undergoing treatment with the compound(s) and/or composition(s) described herein.

Described below are non-limiting pharmaceutical compositions and methods for preparing the same.

Pharmaceutical Compositions for Oral Administration

In an embodiment, the invention provides a pharmaceutical composition for oral administration containing the active pharmaceutical ingredient or combination of active pharmaceutical ingredients, such as the HDAC inhibitors described herein, and a pharmaceutical excipient suitable for oral administration.

In some embodiments, the invention provides a solid pharmaceutical composition for oral administration containing: (i) an effective amount of an active pharmaceutical ingredient or combination of active pharmaceutical ingredients, and (ii) a pharmaceutical excipient suitable for oral administration. In selected embodiments, the composition further contains (iii) an effective amount of a third active pharmaceutical ingredient and optionally (iv) an effective amount of a fourth active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogs thereof, polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of a compound described herein and to minimize precipitation of the compound. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, S-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In some embodiments, a pharmaceutical composition is provided for injection containing an active pharmaceutical ingredient or combination of active pharmaceutical ingredients, such as an HDAC inhibitor, and a pharmaceutical excipient suitable for injection.

The forms in which the compositions described herein may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, a pharmaceutical composition is provided for transdermal delivery containing an active pharmaceutical ingredient or combination of active pharmaceutical ingredients, such as HDAC inhibitors described herein, and a pharmaceutical excipient suitable for transdermal delivery.

Compositions described herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods described herein employs transdermal delivery devices ("patches"). Such transdermal patches may be used to provide continuous or discontinuous infusion of an active pharmaceutical ingredient or combination of active pharmaceutical ingredients in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445; and 5,001,139, the entirety of which are incorporated herein by reference. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra and the HDAC inhibitors described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions of the HDAC inhibitors described herein may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The active pharmaceutical ingredient or combination of active pharmaceutical ingredients can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit comprising a composition comprising a therapeutically effective amount of an active pharmaceutical ingredient (e.g., HDAC inhibitor) or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides a kit comprising (1) a composition comprising a therapeutically effective amount of an active pharmaceutical ingredient (e.g., HDAC inhibitor) or combination of active pharmaceutical ingredients or a pharmaceutically acceptable salt, solvate, hydrate, cocrystal, or prodrug thereof, and (2) a diagnostic test for determining whether a patient's cancer is a particular subtype of a cancer. Any of the foregoing diagnostic methods may be utilized in the kit.

For example, a kit of the invention may include one or more HDAC inhibitors and a chemotherapeutic agent and/or an immunotherapeutic agent.

The kits described above are preferably for use in the treatment of the diseases and conditions described herein. In a particular embodiment, the kits are for use in the treatment of cancer, neurological disorders, or immunological disorders.

Dosages and Dosing Regimens

The amounts of the pharmaceutical compositions administered using the methods herein, such as the dosages of HDAC inhibitors, will be dependent on the human or mammal being treated, the severity of the disorder or condition, the rate of administration, the disposition of the active pharmaceutical ingredients and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in mg/m$^2$ of body surface area.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the preferred oral route, may be used as appropriate. A single dose of a pharmaceutical composition may also be used for treatment of an acute condition.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients may continue as long as necessary. In selected embodiments, a pharmaceutical composition is administered for more than 1, 2, 3, 4, 5, 6, 7, 14, or 28 day(s). In some embodiments, a pharmaceutical composition is administered for less than 28, 14, 7, 6, 5, 4, 3, 2, or 1 day(s). In some embodiments, a pharmaceutical composition is administered chronically on an ongoing basis—e.g., for the treatment of chronic effects. In some embodiments, the administration of a pharmaceutical composition continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is less than about 25 mg, less than about 50 mg, less than about 75 mg, less than about 100 mg, less than about 125 mg, less than about 150 mg, less than about 175 mg, less than about 200 mg, less than about 225 mg, or less than about 250 mg. In some embodiments, an effective dosage of an active pharmaceutical ingredient disclosed herein is greater than about 25 mg, greater than about 50 mg, greater than about 75 mg, greater than about 100 mg, greater than about 125 mg, greater than about 150 mg, greater than about 175 mg, greater than about 200 mg, greater than about 225 mg, or greater than about 250 mg.

In some embodiments, an effective dosage of an active pharmaceutical ingredient disclosed herein is in the range of about 0.01 mg/kg to about 200 mg/kg, or about 0.1 to 100 mg/kg, or about 1 to 50 mg/kg.

In some embodiments, an active pharmaceutical ingredient is adminstered at a dosage of 10 to 200 mg BID, including 50, 60, 70, 80, 90, 100, 150, or 200 mg BID. In some embodiments, an active pharmaceutical ingredient is adminstered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect—e.g., by dividing such larger doses into several small doses for administration throughout the day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

In some embodiments, the compositions described herein further include controlled-release, sustained release, or extended-release therapeutic dosage forms for administration of the compounds described herein, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

The following examples describe the invention in further detail. These examples are provided for illustrative purposes only, and should in no way be considered as limiting the invention.

EXAMPLES

Example 1: Synthesis of $N^1$-(2,6-dioxopiperidin-3-yl)-$N^8$-hydroxyoctanediamide Boc-2-aminoglutarimide was first prepared. N-boc-L-glutamine (6 g, 24.36 mmol) was dissolved in 60 mL of dry THF. To this solution, 1,1'-Carbonyldiimidazole (4.35 g, 26.8 mmol) was added followed by 4-dimethylaminopyridine (122.17 mg, 1 mmol) and the solution was heated to reflux and stirred overnight. The solution was then cooled in an ice bath and the resultant solid was filtered and washed with THE to yield the product as colorless needles (4.56 g, 82% yield). $^1$H NMR (CDCl$_3$) δ 1.4 (s, 9H), 1.7-2.0 (m, 1H), 2.5-2.9 (m, 3H), 4.3 (bs, 1H), 5.3 (bs, 1H), 7.9 (bs, 1H).

2,6-dioxo-piperidin-3-yl-ammonium trifluoroacetate was then prepared from the boc-2-aminoglutarimide. TFA (23 mL) was added to boc-2-aminoglutarimide (4.56 g, 20 mmol) and the reaction was stirred at room temperature for 30 minutes. The excess TFA was then removed in vacuo to give the product as a white solid with no further purification necessary. $^1$H NMR (DMSO-d$_6$) δ 1.9-2.3 (m, 2H), 2.4-2.8 (m, 2H), 4.1-4.3 (d, 1H), 8.5 (s, 4H), 11.2 (s, 1H).

Methyl 8-((2,6-dioxopiperidin-3-yl)amino)-8-oxooctanoate was then prepared from 2,6-dioxo-piperidin-3-yl-ammonium trifluoroacetate. 2,6-dioxo-piperidin-3-yl-ammonium trifluoroacetate (2.42 g, 11.71 mmol) was added to DCM (100 mL) and TEA (4.7 g, 46.84 mmol) was added under stirring followed by the dropwise addition of methyl 8-chloro-8-oxooctanoate (2.903 g, 14.05 mmol). The solution was allowed to stir overnight and was quenched by the addition of saturated sodium bicarbonate. The aqueous phase was then extracted 3 times with DCM which was then dried over sodium sulfate and was purified via column using 50% Ethyl Acetate in Hexanes to yield a white powder (2.15 g, 62% yield). $^1$H NMR (DMSO-d$_6$) δ 1.26 (m, 4H), 1.50

(m, 4H), 1.89 (m, 2H), 2.11 (t, 2H), 2.28 (t, 2H), 2.72 (m, 2H), 3.58 (s, 3H), 4.52 (q, 1H), 8.12 (d, 1H), 10.75 (s, 1H). $^{13}$C NMR (DMSO-d$_6$) δ 173.34, 172.93, 172.24, 172.12, 51.14, 48.90, 35.14, 33.21, 30.88, 28.16, 28.12, 24.98, 24.35, 24.31.

The targeted HDAC inhibitor (N$^1$-(2,6-dioxopiperidin-3-yl)-N$^8$-hydroxyoctanediamide) was prepared from methyl 8-((2,6-dioxopiperidin-3-yl)amino)-8-oxooctanoate. Methyl 8-((2,6-dioxopiperidin-3-yl)amino)-8-oxooctanoate (2.15 g, 7.21 mmol) was taken up in methanol (25 mL) and heated to 600 C to dissolve the compound. A solution of hydroxylamine (15 mL, 50% wt in H$_2$O) was added to the solution and allowed to stir for 24 h. Acetone was then added to the solution to quench the reaction and the solvent was removed under vacuum. The acetoxime was sublimated under high vacuum and the remaining residue was purified via column using 25-50% Methanol in Ethyl Acetate to yield a tan colored solid (1.35 g, 63% yield).

Example 2: Synthesis of N$^1$-(2-(2,6-dioxopiperidin-3-yl)-1-oxoisoindolin-4-yl)-N$^8$-hydroxyoctanediamide Methyl 8-((2-(2,6-dioxopiperidin-3-yl)-1-oxoisoindolin-4-yl)amino)-8-oxoocatanoate was first prepared. Lenalidomide (400 mg, 1.54 mmol) was dissolved in 20 mL of DMF after which triethylamine (467.5 mg, 4.62 mmol) was added and allowed to stir for 15 minutes. Methyl 8-chloro-8-oxooctanoate (318.9 mg, 1.54 mmol) was then added to the solution slowly and allowed to stir for 24 hours. The DMF and triethylamine were then removed under reduced pressure and the residue was taken up in EtOAc and extracted washed a saturated ammonium chloride solution. The organic layer was then dried over sodium sulfate, evaporated and purified via column using 50% EtOAc/Hexanes to yield 375 mg (57% yield) of a pale yellow solid. $^1$H NMR (DMSO-d$_6$) δ 1.31 (m, 4H), 1.53 (m, 2H), 1.60 (m, 2H), 2.03 (m, 1H), 2.32 (m, 5H), 2.61 (m, 1H), 2.91 (m, 1H), 3.57 (s, 3H), 4.36 (q, 2H), 5.14 (q, 1H), 7.50 (m, 2H), 7.80 (m, 1H), 9.75 (s, 1H), 11.00 (s, 1H). $^{13}$C NMR (DMSO-d$_6$) δ 173.79, 173.29, 171.78, 171.50, 159.74, 134.24, 134.04, 133.12, 129.06, 119.34, 51.99, 59.61, 36.16, 33.66, 28.72, 28.62, 25.34, 24.76, 23.09.

The target HDAC inhibitor (N$^1$-(2-(2,6-dioxopiperidin-3-yl)-1-oxoisoindolin-4-yl)-N$^8$-hydroxyoctanediamide) was prepared from 8-((2-(2,6-dioxopiperidin-3-yl)-1-oxoisoindolin-4-yl)amino)-8-oxoocatanoate. Methyl 8-((2-(2,6-dioxopiperidin-3-yl)-1-oxoisoindolin-4-yl)amino)-8-oxoocatanoate (375 g, 0.87 mmol) was taken up in methanol (15 mL) and heated to 600 C to dissolve the compound. A solution of hydroxylamine (6 mL, 50% wt in H$_2$O) was added to the solution and allowed to stir for 24 h. Acetone was then added to the solution to quench the reaction and the solvent was removed under vacuum. The acetoxime was sublimated under high vacuum and the remaining residue was purified via column using 25-50% Methanol in Ethyl Acetate to yield a pale yellow solid (229 mg, 61% yield).

Example 3: In Vitro Inhibition Studies of HDAC with Compounds of the Invention

The Pan HDAC assays described herein were performed as follows:

Materials: Enzo Fluor-de-Lys HDAC fluorometric activity assay kit; 360 nm excitation 460 nm emission Plate Reader; Disposable pipettes; Pipet-aid; Pipette tips; Micropipetter; DMSO; Sterile micro-tubes and conical tubes; and Micro-centrifuge.

Test compounds and control preparation: All test compounds' stock solutions were made in 100% DMSO. Test compound dilutions were made in HDAC Assay buffer with a final concentration of DMSO less than or equal to 1%. Vehicle control was HDAC Assay buffer with 1% DMSO.

The reagents for the assay were prepared as follows:

1. All kit components were defrosted and these, and all dilutions described below, were kept on ice until use. All undiluted kit components are stable for several hours on ice.

2. A sufficient amount of HeLa Nuclear Extract (BML-KI140) or other HDAC source diluted in Assay Buffer (BML-KI143) was prepared to provide for the assays that were performed (# of wells×15 µl). A 30-fold dilution of the HeLa Extract means that 15 µL contains 0.5 µl of the undiluted Extract, an appropriate amount to use per well.

3. Dilution(s) of SAHA and/or Test Inhibitors were prepared in Assay Buffer (BML-K1143). Since 10 µl were used per well, and since the final volume of the HDAC reaction was 50 µl, these inhibitor dilutions were 5× their final concentration.

4. Dilution(s) of the Fluor de Lys® Substrate (BML-KI104; 50 mM) were prepared in Assay Buffer (BML-K1143) that were 2× the desired final concentration(s). For inhibitor screening, substrate concentrations at or below the Km are recommended. Twenty-five µL were used per well. Initial dilutions of 25-fold or greater in Assay Buffer (2.0 mM or less) yielded stable solutions (see NOTE on freezing and thawing below). Rapid mixing and dilution into room temperature buffer helped to prevent precipitation at high substrate concentration. NOTE: Freezing/thawing of Fluor de Lys® Substrate solutions in Assay Buffer may cause precipitation of the Substrate. Dilute only amount necessary for one day's experiment.

5. Shortly before use (<30 min.), sufficient Fluor de Lys® Developer was prepared for the assays to be performed (50 µl per well). First, the Fluor de Lys® Developer Concentrate was diluted 20-fold (e.g. 50p plus 950 µl Assay Buffer) in cold Assay Buffer (BML-K1143). Second, the 0.2 mM Trichostatin A (BML-GR309-9090) was diluted 100-fold in the 1× Developer just prepared (e.g. 10 µl in 1 ml; final Trichostatin A concentration in the 1× Developer=2 µM; final concentration after addition to HDAC/Substrate reaction=1 µM). The addition of SAHA to the Developer insures that HDAC activity stops when the Developer is added. The Developer was kept on ice until use.

Assay Procedure:

1. Assay buffer, diluted trichostatin A or test inhibitor was added to appropriate wells of the microtiter plate.

2. Diluted HeLa extract or other HDAC sample was added to all wells except those that are to be "No Enzyme Controls."

3. Diluted Fluor de Lys® Substrate and the samples in the microtiter plate were allowed to equilibrate to assay temperature (e.g. 25 or 37° C.).

4. HDAC reactions were initiated by adding diluted substrate (25 µl) to each well and mixing thoroughly.

5. HDAC reactions were allowed to proceed for desired length of time and then stop them by addition of Fluor de Lys® Developer (50 µl). The plates were incubated at room temperature (25° C.) for 10-15 min. Signal is stable for at least 30 min. beyond this time.

6. Samples were read in a microtiter-plate reading fluorimeter capable of excitation at a wavelength in the range 350-380 nm and detection of emitted light in the range 440-460 nm.

The HDAC isomer (HDAC1, 3, and 6) assays were performed as follows:

Materials: Human recombinant HDAC isomer (HDAC1, HDAC3, and HDAC6); Fluor-de-Lys HDAC substrates; 360 nm excitation 460 nm emission Plate Reader; Disposable pipettes; Pipet-aid; Pipette tips; Micro-pipetter; DMSO; Sterile micro-tubes and conical tubes; and Micro-centrifuge.

Test compounds and control preparation: All test compounds' stock solutions were made in 100% DMSO. Test compound dilutions were made in HDAC Assay buffer with a final concentration of DMSO less than or equal to 1%. Vehicle control was HDAC Assay buffer with 1% DMSO.

The reagents for the assay were prepared as follows:

1. All kit components were defrosted and these, and all dilutions described below, were kept on ice until use. All undiluted kit components are stable for several hours on ice.

2. A sufficient amount of HDAC source diluted in Assay Buffer (BML-KI143) was prepared to provide for the assays that were performed (# of wells×15 µl). A 30-fold dilution of the HeLa Extract means that 15p L contains 0.5 µl of the undiluted Extract, an appropriate amount to use per well.

3. Dilution(s) of SAHA and/or Test Inhibitors were prepared in Assay Buffer (BML-KI143). Since 10 µl were used per well, and since the final volume of the HDAC reaction was 50p, these inhibitor dilutions were 5× their final concentration.

4. Dilution(s) of the Fluor de Lys® Substrate (BML-KI104; 50 mM) were prepared in Assay Buffer (BML-KI143) that were 2× the desired final concentration(s). For inhibitor screening, substrate concentrations at or below the Km are recommended. Twenty-five µL were used per well. Initial dilutions of 25-fold or greater in Assay Buffer (2.0 mM or less) yielded stable solutions. Rapid mixing and dilution into room temperature buffer helped to prevent precipitation at high substrate concentration.

5. Shortly before use (<30 min.), sufficient Fluor de Lys® Developer was prepared for the assays to be performed (50 µl per well). First, the Fluor de Lys® Developer Concentrate was diluted 20-fold (e.g. 50 µl plus 950 µl Assay Buffer) in cold Assay Buffer (BML-K1143). Second, the 0.2 mM Trichostatin A (BML-GR309-9090) was diluted 100-fold in the 1× Developer just prepared (e.g. 10 µl in 1 ml; final Trichostatin A concentration in the 1× Developer=2 µM; final concentration after addition to HDAC/Substrate reaction=1 µM). The addition of SAHA to the Developer insures that HDAC activity stops when the Developer is added. The Developer was kept on ice until use.

Assay Procedure:

1. Assay buffer, diluted trichostatin A or test inhibitor was added to appropriate wells of the microtiter plate.

2. Diluted HeLa extract or other HDAC sample was added to all wells except those that are to be "No Enzyme Controls."

3. Diluted Fluor de Lys® Substrate and the samples in the microtiter plate were allowed to equilibrate to assay temperature (e.g. 25 or 37° C.).

4. HDAC reactions were initiated by adding diluted substrate (25 µl) to each well and mixing thoroughly.

5. HDAC reactions were allowed to proceed for desired length of time and then stop them by addition of Fluor de Lys® Developer (50 µl). The plates were incubated at room temperature (25° C.) for 10-15 min. Signal is stable for at least 30 min. beyond this time.

6. Samples were read in a microtiter-plate reading fluorimeter capable of excitation at a wavelength in the range 350-380 nm and detection of emitted light in the range 440-460 nm.

Figures 2, 3, 4:
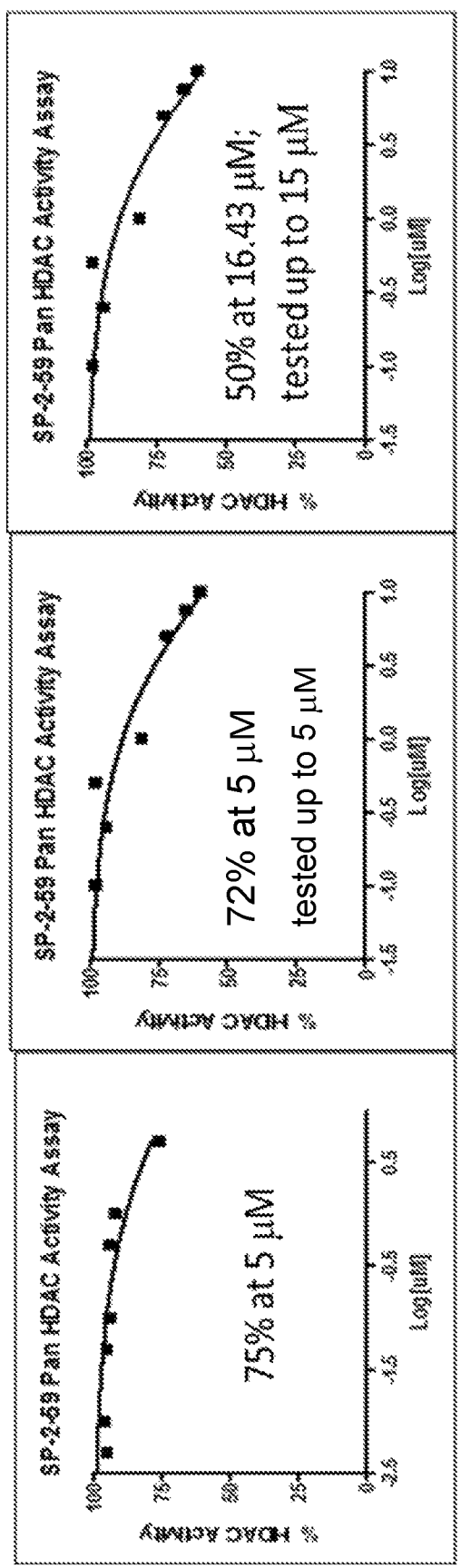
FIG. 2 illustrates the in vitro inhibitory activity of $N^1$-(2,6-dioxopiperidin-3-yl)-$N^8$-hydroxyoctanediamide (i.e., SP-2-59) against pan-HDACs.
FIG. 3 illustrates the in vitro inhibitory activity of $N^1$-(2,6-dioxopiperidin-3-yl)-$N^8$-hydroxyoctanediamide (i.e., SP-2-59) against pan-HDACs.
FIG. 4 illustrates the in vitro inhibitory activity of $N^1$-(2,6-dioxopiperidin-3-yl)-$N^8$-hydroxyoctanediamide (i.e., SP-2-59) against pan-HDACs.

A shown in FIGS. 2-4, the tested compounds demonstrated inhibitor activity in the Pan-HDAC assay. For example, as shown in FIG. 4, N1-(2,6-dioxopiperidin-3-yl)-N8-hydroxyoctanediamide (i.e., SP-2-59) demonstrated an average EC50 of 16.43 µM.

Example 4: In Vitro Inhibition of HDAC6 as Compared to Pan-HDACs $N^1$-(2,6-dioxopiperidin-3-yl)-$N^8$-hydroxyoctanediamide (i.e., SP-2-59) was tested in vitro as an inhibitor of HDAC6 and pan-HDACs. As shown in FIG. 1, $N^1$-(2,6-dioxopiperidin-3-yl)-$N^8$-hydroxyoctanediamide demonstrates a substantial preference and selectivity for HDAC6 as compared to the pan-HDACs assay. Moreover, as shown in FIGS. 2 to 4, $N^1$-(2,6-dioxopiperidin-3-yl)-$N^8$-hydroxyoctanediamide demonstrates minimal inhibitor activity in the pan-HDACs assays between 5 µM and 15 µM. Indeed, as shown in FIG. 4, N1-(2,6-dioxopiperidin-3-yl)-N8-hydroxyoctanediamide (i.e., SP-2-59) demonstrated an average $EC_{50}$ of 16.43 µM.

Figures 5, 6:
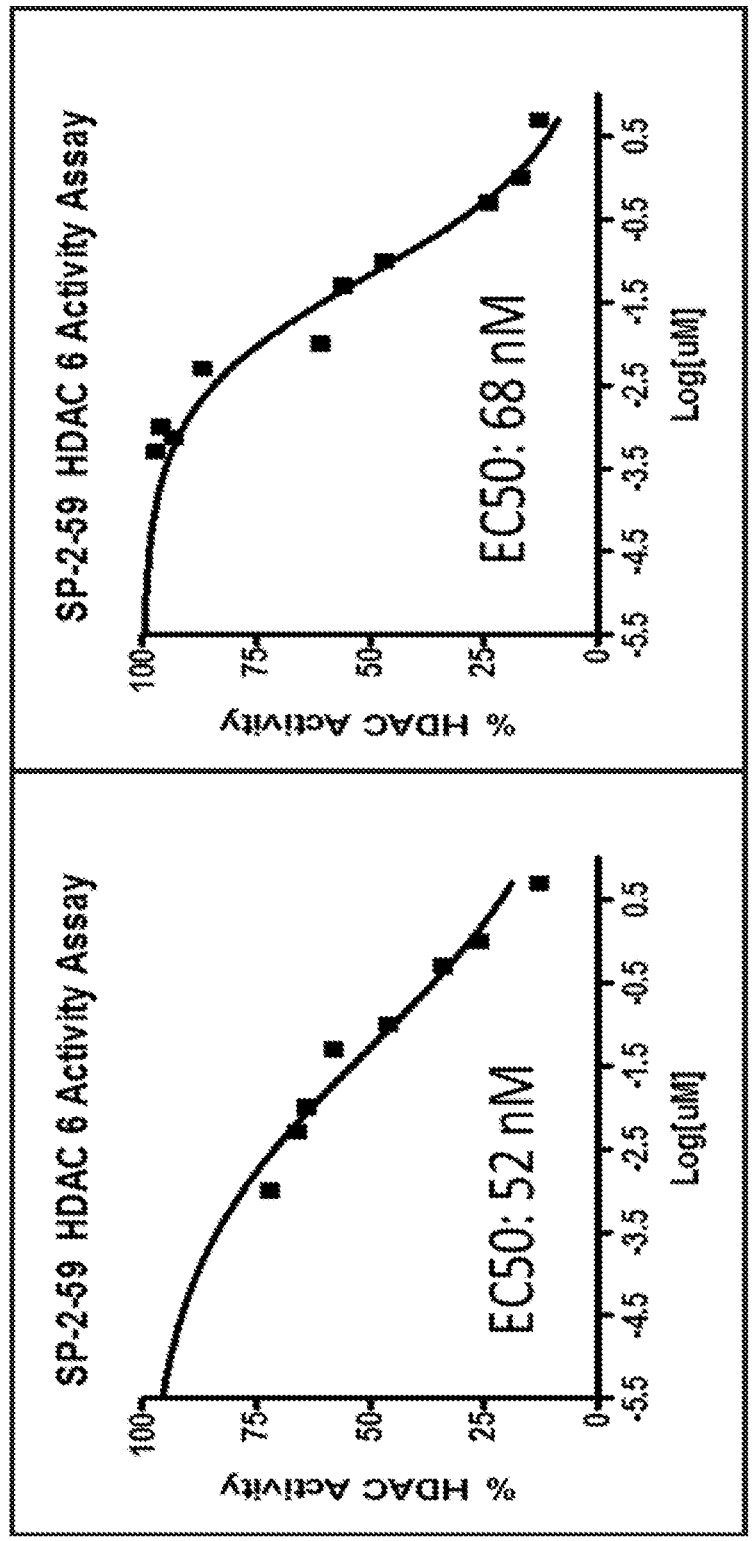
FIG. 5 illustrates the in vitro inhibitory activity of $N^1$-(2,6-dioxopiperidin-3-yl)-$N^8$-hydroxyoctanediamide (i.e., SP-2-59) against HDAC6.
FIG. 6 illustrates the in vitro inhibitory activity of $N^1$-(2,6-dioxopiperidin-3-yl)-$N^8$-hydroxyoctanediamide (i.e., SP-2-59) against HDAC6.
Figure 7:
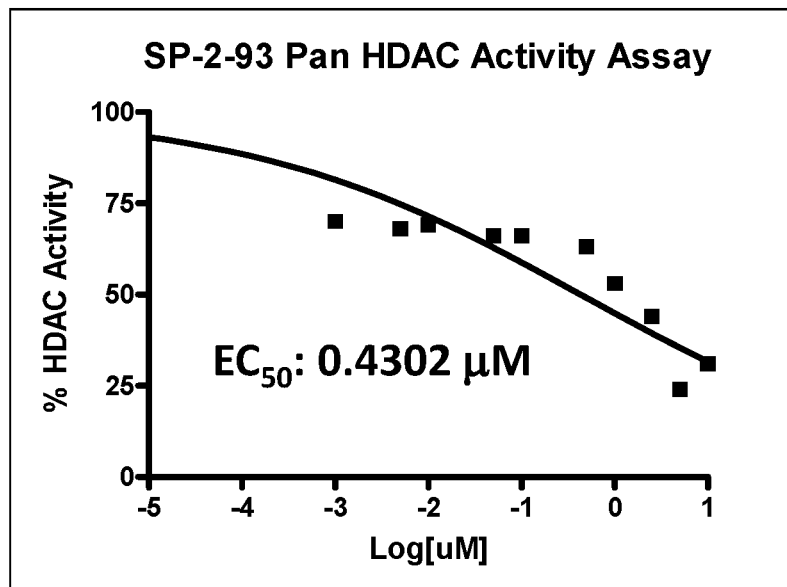
FIG. 7 illustrates the in vitro inhibitory activity of $N^1$-(2-(2,6-dioxopiperidin-3-yl)-1-oxoisoindolin-4-yl)-$N^8$-hydroxyoctanediamide (i.e., SP-2-93) against pan-HDACs.

$N^1$-(2,6-dioxopiperidin-3-yl)-$N^8$-hydroxyoctanediamide was further tested in vitro against HDAC6 alone. In two assays, $N^1$-(2,6-dioxopiperidin-3-yl)-$N^8$-hydroxyoctanediamide was found to have $EC_{50}$s of 52 nM and 68 nM against HDAC6 (FIGS. 5 and 6, respectively).

$N^1$-(2-(2,6-dioxopiperidin-3-yl)-1-oxoisoindolin-4-yl)-$N^8$-hydroxyoctanediamide (i.e., SP-2-93) was also tested in vitro as an inhibitor of HDAC6 and pan-HDACs. As shown FIGS. 7 and 8, $N^1$-(2-(2,6-dioxopiperidin-3-yl)-1-oxoisoindolin-4-yl)-$N^8$-hydroxyoctanediamide (i.e., SP-2-93) demonstrates a substantial preference and selectivity for HDAC6 as compared to the pan-HDACs.

Figure 11:
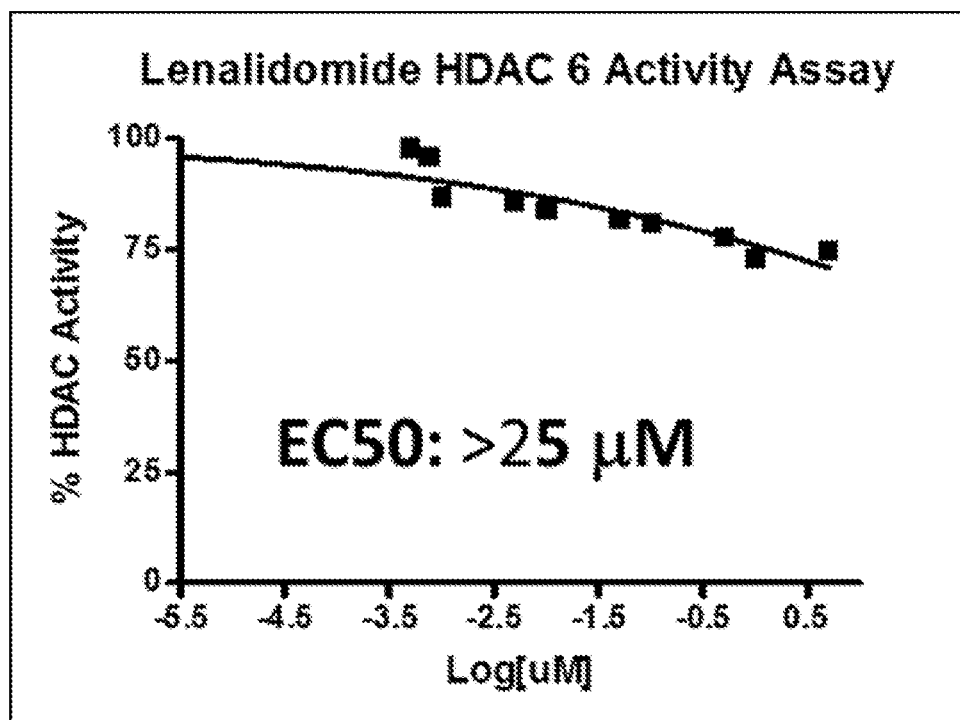
FIG. 11 illustrates the in vitro inhibitory activity of lenalidomide against HDAC6.
Figure 12:
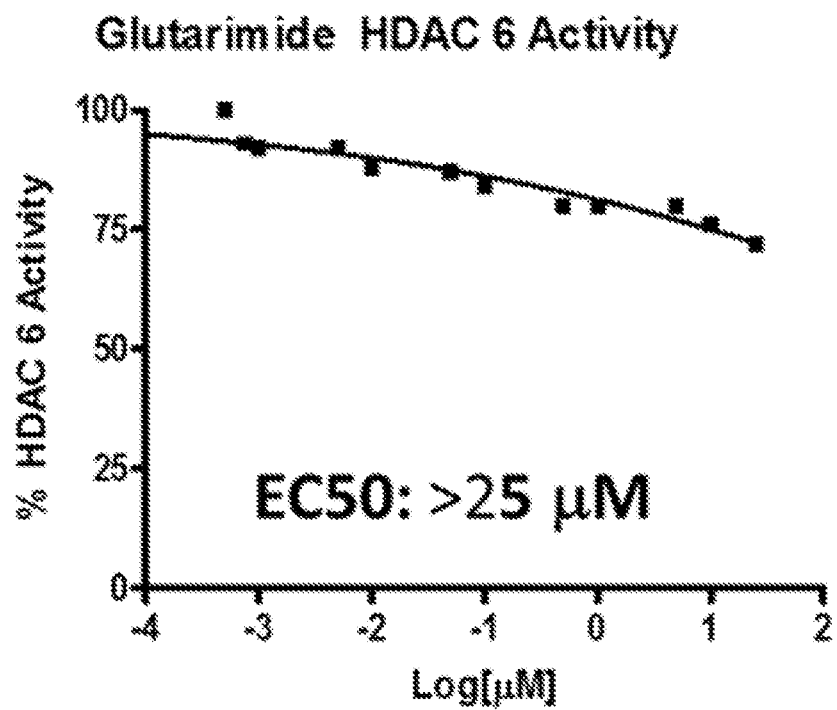
FIG. 12 illustrates the in vitro inhibitory activity of glutarimide against HDAC6.

As proof of concept, lenalidomide and glutarimide were tested in vitro against HDAC6. As shown in FIG. 11, lenalidomide exhibited an $EC_{50}$ of greater than 25 µM. As shown in FIG. 12, glutaramide exhibited an $EC_{50}$ of greater than 25 µM.

To determine the selectivity of $N^1$-(2,6-dioxopiperidin-3-yl)-$N^8$-hydroxyoctanediamide (i.e., SP-2-59) and $N^1$-(2-(2,6-dioxopiperidin-3-yl)-1-oxoisoindolin-4-yl)-$N^8$-hydroxyoctanediamide (i.e., SP-2-93) for HDAC6 as compared to other specific HDAC proteins, the compounds were tested against HDAC1 and HDAC3, in addition to the pan-HDACs mentioned previously (see FIGS. 9, 10, 13, and 14).

Figure 8:
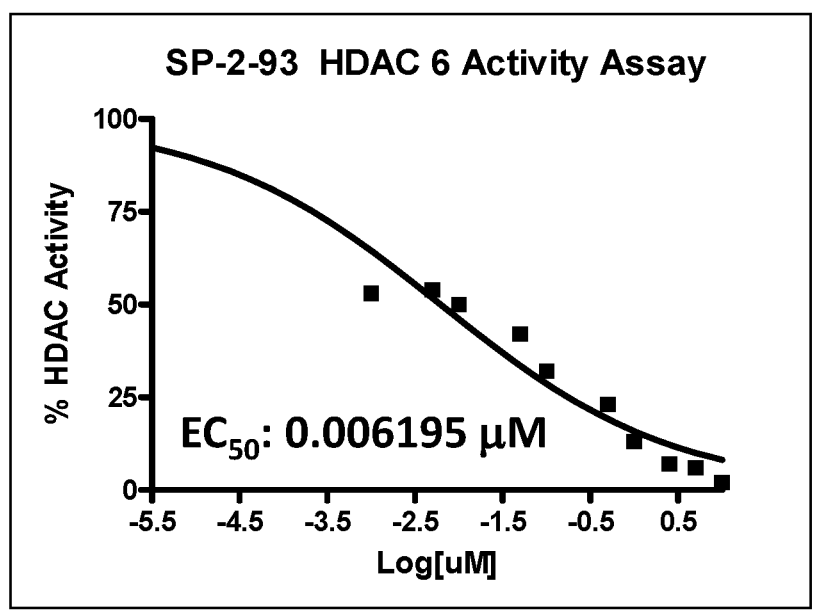
FIG. 8 illustrates the in vitro inhibitory activity of $N^1$-(2-(2,6-dioxopiperidin-3-yl)-1-oxoisoindolin-4-yl)-$N^8$-hydroxyoctanediamide (i.e., SP-2-93) against HDAC6.
Figure 9:
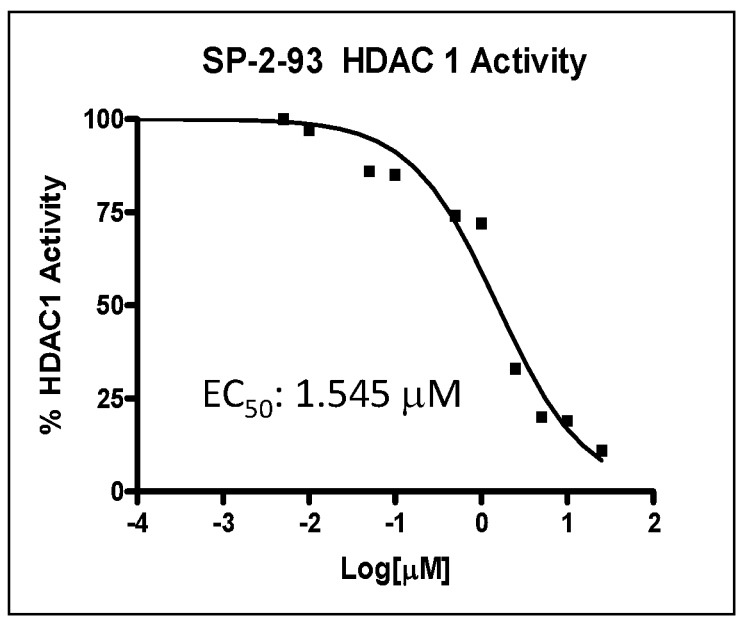
FIG. 9 illustrates the in vitro inhibitory activity of $N^1$-(2-(2,6-dioxopiperidin-3-yl)-1-oxoisoindolin-4-yl)-$N^8$-hydroxyoctanediamide (i.e., SP-2-93) against HDAC1.
Figure 10:
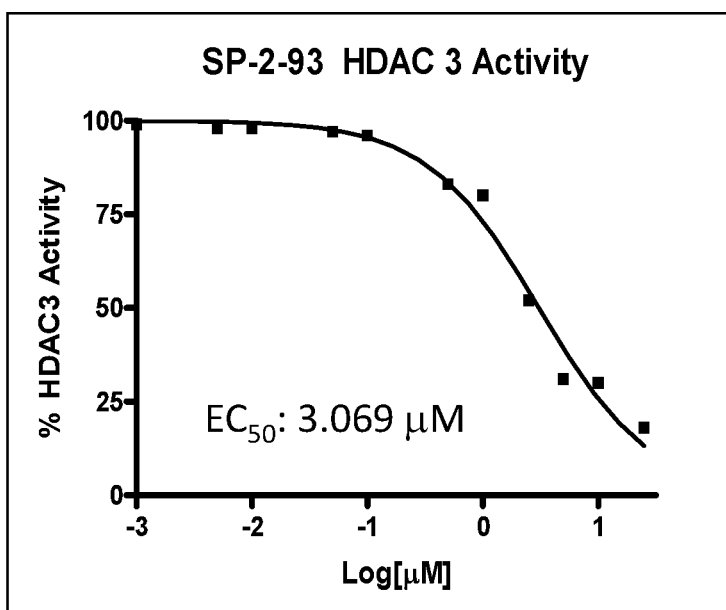
FIG. 10 illustrates the in vitro inhibitory activity of $N^1$-(2-(2,6-dioxopiperidin-3-yl)-1-oxoisoindolin-4-yl)-$N^8$-hydroxyoctanediamide (i.e., SP-2-93) against HDAC3.

Indeed, as shown in FIGS. 9 and 10, $N^1$-(2-(2,6-dioxopiperidin-3-yl)-1-oxoisoindolin-4-yl)-$N^8$-hydroxyoctanediamide (i.e., SP-2-93) demonstrates less inhibitory activity for HDAC1 ($EC_{50}$=1.545 µM) and HDAC3 ($EC_{50}$=3.069 µM), respectively, as compared to HDAC6 ($EC_{50}$=6.195 nM) (FIG. 8).

Figures 13, 14:
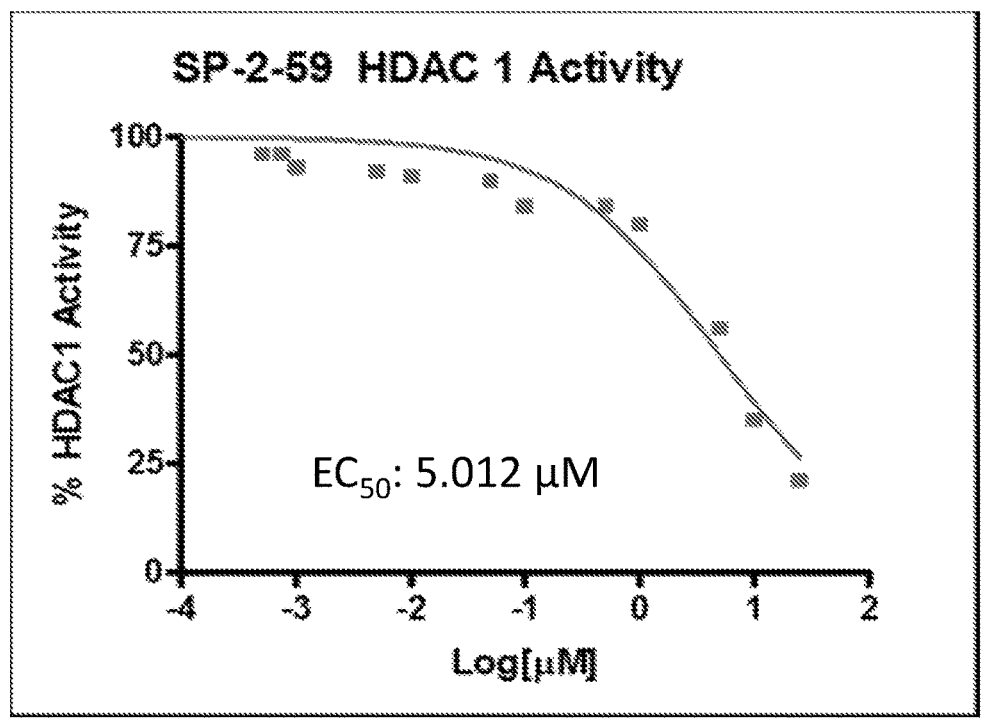
FIG. 13 illustrates the in vitro inhibitory activity of $N^1$-(2,6-dioxopiperidin-3-yl)-$N^8$-hydroxyoctanediamide (i.e., SP-2-59) against HDAC1.
FIG. 14 provides a table that compares the in vitro inhibitory activities of $N^1$-(2,6-dioxopiperidin-3-yl)-$N^8$-hydroxyoctanediamide (i.e., SP-2-59), $N^1$-(2-(2,6-dioxopiperidin-3-yl)-1-oxoisoindolin-4-yl)-$N^8$-hydroxyoctanediamide, (i.e., SP-2-93), lenalidomide, and glutarimide.

Taking the data as a whole, the compounds of the invention demonstrated greater specificity against HDAC6 as compared to HDAC1, HDAC3, and the pan-HDACs. For example, $N^1$-(2,6-dioxopiperidin-3-yl)-$N^8$-hydroxyoctanediamide inhibited HDAC6, as compared to HDAC1, with 83-fold greater potency (FIG. 14). Moreover, $N^1$-(2-(2,6-dioxopiperidin-3-yl)-1-oxoisoindolin-4-yl)-$N^8$-hydroxyoctanediamide inhibited HDAC6, as compared to HDAC1, with 258-fold greater potency (FIG. 14).

Example 5: N¹-(2,6-dioxopiperidin-3-yl)-N⁸-hydroxyoctanediamide and N¹-(2-(2,6-dioxopiperidin-3-yl)-1-oxoisoindolin-4-yl)-N⁸-hydroxyoctanediamide were Tested as Cytotoxic Agents Against Breast Cancer Cells Cell Counting Kit-8 (CCK-8) (Dojindo) was used to determine the cytotoxicity of cells. CCK-8 assay kit uses a water-soluble WST-8 tetrazolium salt. This tetrazolium salt produces a water-soluble formazan dye upon reduction in the presence of an electron mediator (dehydrogenase). When WST-8 is reduced by dehydrogenases in living cells an orange colored product (formazan) is produced that can be detected in a 96-well plate format. The amount of the formazan dye generated by dehydrogenases is directly proportional to the number of living cells.

For this assay the following materials were required:
1. Plate reader (450 nm filter);
2. 96-well plate;
3. CO2 incubator;
4. 10 µl and 100-200 µl pipettes;
5. Tissue Culture Media; and
6. Actively growing cells (75-80% confluency).

The following dilutions with cell media were made prior to performance of an assay: Test compound solutions were made in a range from nano-molar to micro-molar with a final DMSO concentration not exceeding 0.1% and a total volume (e.g., 300 ul) necessary to perform duplicates of 100 µl doses.

A Cell Proliferation and Cytotoxicity Assay was performed as follows:
1. Dispense 100 µl of cell suspension (5000 cells/well) in a 96-well plate equal to the number of treatments plus controls done in duplicate;
2. Allow seeded cells to plate for 24 hours in a humidified incubator (at 37° C., 5% CO2);
3. After 24 hours aspirate old media and add 100 µl of the test compound dilutions to appropriate wells;
4. Incubate the plate for 48 hours in the incubator;
5. Create a 10% CCK-8 solution mixed with cell media sufficient enough to add 100 ul to each treated well of the plate;
6. Incubate the plate for 1 hour in the incubator;
7. Measure the absorbance at 450 nm using a micro-plate reader; and
8. Graph results and calculate $IC_{50}$.

N¹-(2,6-dioxopiperidin-3-yl)-N⁸-hydroxyoctanediamide (i.e., SP-2-59) and N¹-(2-(2,6-dioxopiperidin-3-yl)-1-oxoisoindolin-4-yl)-N⁸-hydroxyoctanediamide (i.e., SP-2-93) were tested as described above to determine their cytotoxic activities.

Figure 15:
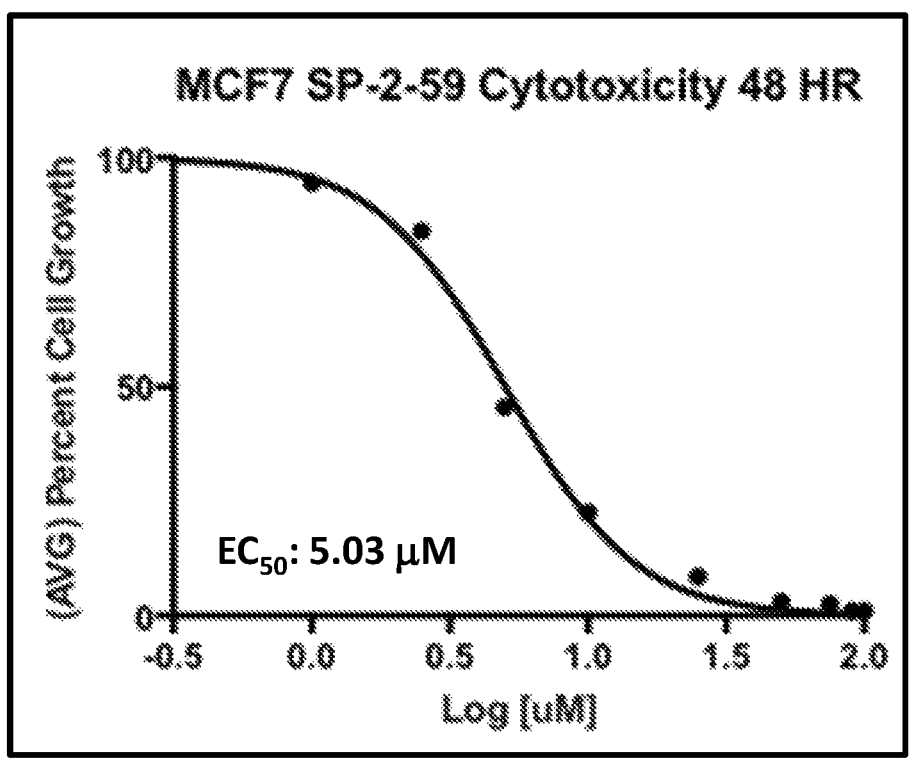
FIG. 15 illustrates an in vitro assay that measured the cytotoxic activity of $N^1$-(2,6-dioxopiperidin-3-yl)-$N^8$-hydroxyoctanediamide (i.e., SP-2-59) against MCF7 cells.

N¹-(2,6-dioxopiperidin-3-yl)-N⁸-hydroxyoctanediamide (i.e., SP-2-59) was tested against MCF-7 breast cancer cells in vitro. As shown in FIG. 15, N¹-(2,6-dioxopiperidin-3-yl)-N⁸-hydroxyoctanediamide exhibited an $EC_{50}$ of 5.03 µM, where 78% of MCF-7 cells were killed at about 10 µM.

Figure 16:
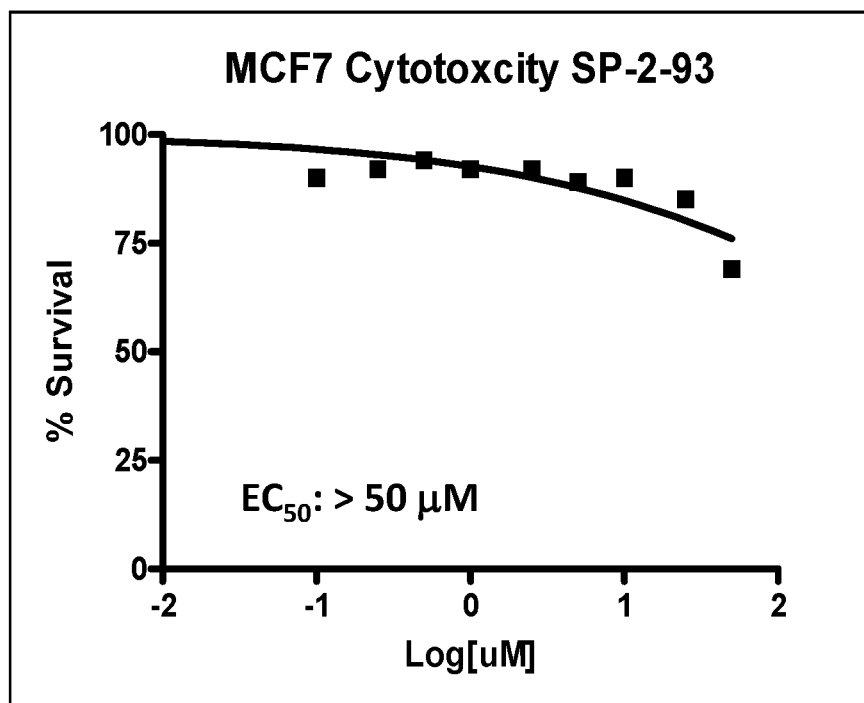
FIG. 16 illustrates an in vitro assay that measured the cytotoxic activity of activity of $N^1$-(2-(2,6-dioxopiperidin-3-yl)-1-oxoisoindolin-4-yl)-$N^8$-hydroxyoctanediamide (i.e., SP-2-93) against MCF7 cells.
Figure 17:
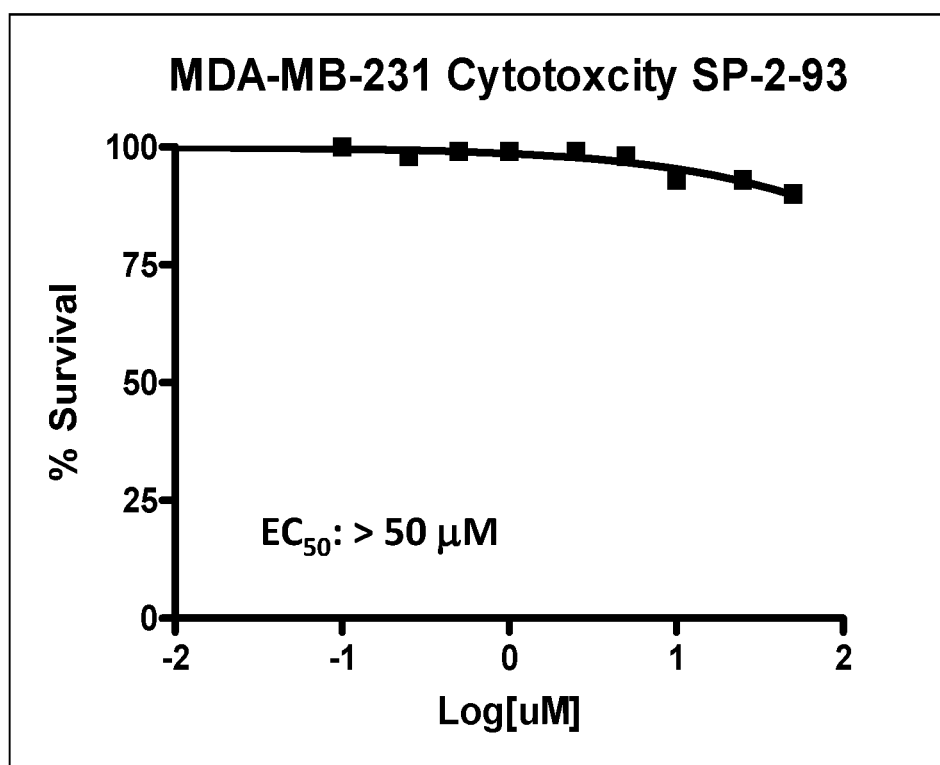
FIG. 17 illustrates an in vitro assay that measured the cytotoxic activity of $N^1$-(2-(2,6-dioxopiperidin-3-yl)-1-oxoisoindolin-4-yl)-$N^8$-hydroxyoctanediamide (i.e., SP-2-93) against MDA-MB-231 cells.

N¹-(2-(2,6-dioxopiperidin-3-yl)-1-oxoisoindolin-4-yl)-N⁸-hydroxyoctanediamide was tested as a cytotoxic agent against MCF7 (FIG. 16) and MDA-MB-231 (FIG. 17) breast cancer cells in vitro.

Example 6: N¹-(2-(2,6-dioxopiperidin-3-yl)-1-oxoisoindolin-4-yl)-N⁸-hydroxyoctanediamide (i.e., SP-2-93) was Tested as a Selective Inhibitor of HDAC6 as Compared to SAHA and TSA N¹-(2-(2,6-dioxopiperidin-3-yl)-1-oxoisoindolin-4-yl)-N⁸-hydroxyoctanediamide (i.e., SP-2-93) was tested in assay to determine the selectivity of the compound for specific HDAC proteins as compared to SAHA and TSA. The compound was tested against Pan HDAC, HDAC1, HDAC3, and HDAC6. N¹-(2-(2,6-dioxopiperidin-3-yl)-1-oxoisoindolin-4-yl)-N⁸-hydroxyoctanediamide was provided in vitro in a 2 mg/mL formulation in a solution of DMSO, PEG400, and PBS (5% DMSO/40% PEG 400/55% PBS). As shown in FIG. 18, N¹-(2-(2,6-dioxopiperidin-3-yl)-1-oxoisoindolin-4-yl)-N⁸-hydroxyoctanediamide had an $IC_{50}$ of 1.89 µM against the PAN HDAC, an $IC_{50}$ of 1.54 µM against HDAC1 protein, an $IC_{50}$ of 3.07 µM against HDAC3 protein, and an $IC_{50}$ of 60 nM against HDAC6 protein.

As compared to HDAC1 and HDAC3, N¹-(2-(2,6-dioxopiperidin-3-yl)-1-oxoisoindolin-4-yl)-N⁸-hydroxyoctanediamide was about 26 times and about 51 times more selective for HDAC6, respectively.

By comparison, SAHA was about 3 times and about 2 times more selective for HDAC6 as compared to HDAC1 and HDAC3, respectively.

N¹-(2-(2,6-dioxopiperidin-3-yl)-1-oxoisoindolin-4-yl)-N⁸-hydroxyoctanediamide was found to be surprising selective for HDAC6 as compared to HDAC1, HDAC3, or Pan HDAC proteins.

A number of patent and non-patent publications are cited herein in order to describe the state of the art to which this invention pertains. The entire disclosure of each of these publications is incorporated by reference herein.

While certain embodiments have been described and/or exemplified above, various other embodiments will be apparent to those skilled in the art from the foregoing disclosure. The invention described herein is, therefore, not limited to the particular embodiments described and/or exemplified, but is capable of considerable variation and modification without departure from the scope of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, and methods described herein that embody the invention can, in alternate embodiments, be more specifically defined by any of the transitional terms "comprising," "consisting essentially of," and "consisting of."

What is claimed is:

1. A pharmaceutical composition comprising a histone deacetylase (HDAC) inhibitor or a pharmaceutically acceptable salt, solvate, hydrate, cocrystal, or prodrug thereof in an amount effective to treat a disease alleviated by inhibiting HDAC protein activity in a patient in need thereof and a physiologically compatible carrier medium, wherein the HDAC inhibitor is a compound of the formula (Ia) or (Ib)

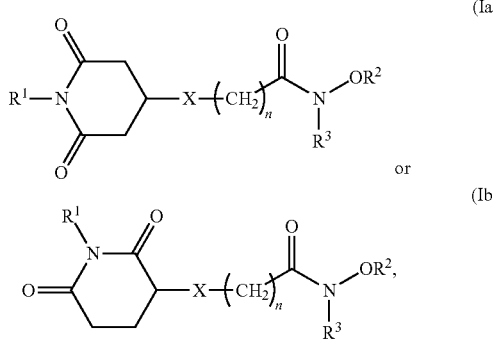

wherein $R^1$ is a substituent selected from the group consisting of H and optionally substituted alkyl and aryl;

$R^2$ is a substituent selected from the group consisting of H and optionally substituted alkyl and aryl;

$R^3$ is a substituent selected from the group consisting of H and optionally substituted alkyl and aryl;

X is a substituent selected from the group consisting of —N(R$^4$)C(O)—, —C(O)N(R$^4$)—, —S(O)$_2$N(R$^4$)—, —N(R$^4$)S(O)$_2$—,

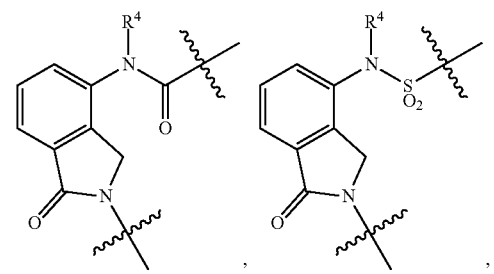

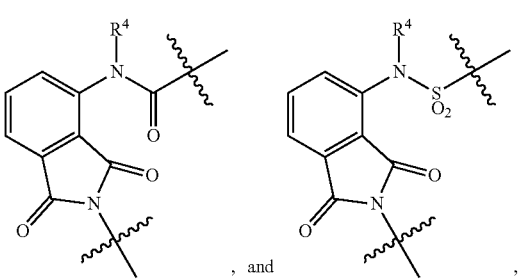

where $R^4$ is a substituent selected from the group consisting of H and optionally substituted alkyl and aryl; n is an integer from 5 to 7.

2. The pharmaceutical composition of claim 1, wherein the HDAC inhibitor is a compound of formula

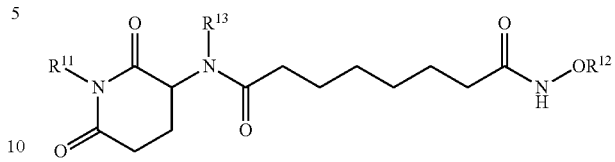

wherein $R^{11}$ is a substituent selected from the group consisting of H and optionally substituted alkyl and aryl;

$R^{12}$ is a substituent selected from the group consisting of H and optionally substituted alkyl and aryl;

$R^{13}$ is a substituent selected from the group consisting of H and optionally substituted alkyl and aryl; or a pharmaceutically acceptable salt, solvate, hydrate, cocrystal, or prodrug thereof.

3. The pharmaceutical composition of claim 1, wherein the HDAC inhibitor is a compound of formula:

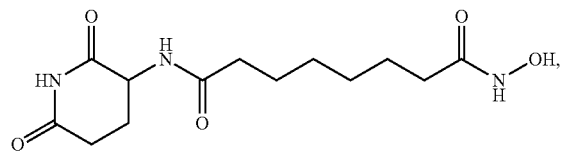 [SMILES: O=C(CCCCCCC(=O)NC1CCC(=O)NC1=O)NO]

or a pharmaceutically acceptable salt, solvate, hydrate, cocrystal, or prodrug thereof.

4. The pharmaceutical composition of claim 1, wherein the HDAC inhibitor is a compound of formula (III):

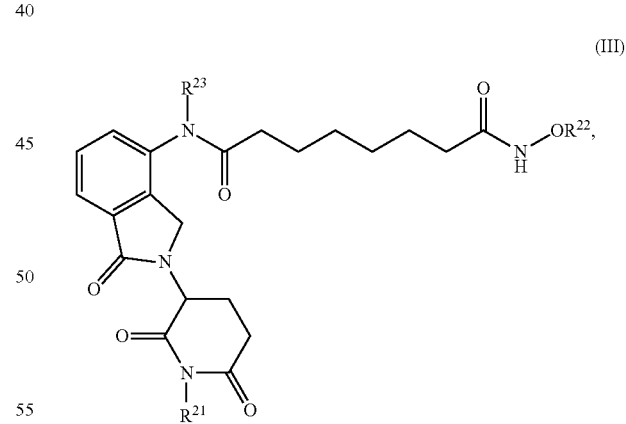

wherein $R^{21}$ is a substituent selected from the group consisting of H and optionally substituted alkyl and aryl;

$R^{22}$ is a substituent selected from the group consisting of H and optionally substituted alkyl and aryl;

$R^{23}$ is a substituent selected from the group consisting of H and optionally substituted alkyl and aryl; or a pharmaceutically acceptable salt, solvate, hydrate, cocrystal, or prodrug thereof.

5. The pharmaceutical composition of claim 1, wherein the HDAC inhibitor is a compound of formula:

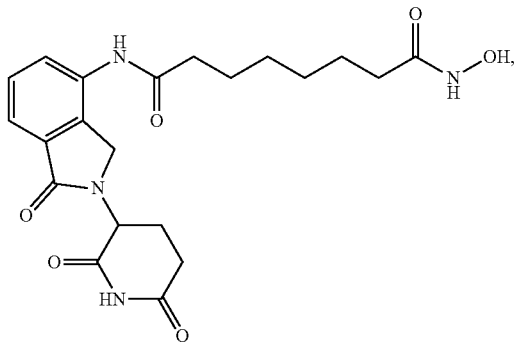 [SMILES: O=C(CCCCCCC(=O)Nc1cccc2c1CN(C1CCC(=O)NC1=O)C2=O)NO]

or a pharmaceutically acceptable salt, solvate, hydrate, cocrystal, or prodrug thereof.

6. The pharmaceutical composition of claim 1 wherein the HDAC inhibitor is a selective HDAC6 inhibitor.

7. A method of treating a disease alleviated by inhibiting histone deacetylase (HDAC) protein in a patient in need thereof, wherein the treatment comprises administering a therapeutically effective amount of the pharmaceutical composition of claim 1.

8. The method of claim 7, wherein the pharmaceutical composition comprises $N^1$-(2,6-dioxopiperidin-3-yl)-N8-hydroxyoctanediamide or $N^1$-(2-(2,6-dioxopiperidin-3-yl)-1-oxoisoindolin-4-yl)-$N^8$-hydroxyoctanediamide, or a pharmaceutically acceptable salt, solvate, hydrate, cocrystal, or prodrug thereof.

9. The method of claim 7, wherein the HDAC inhibitor is administered in dosage unit form.

10. The method of claim 9, wherein the dosage unit comprises a physiologically compatible carrier medium.

11. The method of claim 7, wherein the disease is selected from the group consisting of cancer, an immunological disease, an inflammatory disease, and a neurological disease.

12. The method of claim 11, wherein the cancer is selected from the group consisting of acoustic neuroma, adenocarcinoma, angiosarcoma, astrocytoma, basal cell carcinoma, bile duct carcinoma, bladder carcinoma, brain cancer, breast cancer, brochogenic carcinoma, cervical cancer, chordoma, choriocarcinoma, colon cancer, colorectal cancer, craniopharygioma, cystadenocarcinoma, embryonal carcinoma, endotheliocarconima, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebacaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, and Waldenstrom's macroglobulinemia.

13. The method of claim 12, wherein the cancer comprises an HPV positive (+) cancer.

14. The method of claim 13, wherein the HPV positive (+) cancer comprises one or more of cervical cancer and head and neck cancer.

15. The method of claim 12, further including the step of administering to said patient an amount of radiotherapy configured to treat said cancer.

16. The method of claim 11, wherein the immunological disease is selected from the group consisting of celiac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, rheumatoid arthritis (RA), polymyositis, ulcerative colitis, Crohn's disease, autoimmune carditis, Wegener's granulomatosis, autoimmune hemolytic anemia, polyarteritis nodosa, psoriasis, vitiligo, epidermolysis bullosa, scleroderma, alopecia areata, epidermolysis bullosa acquisita, bullous pemphigoid, pemphigus foliaceous, and pemphigus vulgaris.

17. The method of claim 15, comprising the step of administering an additional therapeutic agent comprising a chemotherapeutic agent or an immunotherapeutic agent.

18. The method of claim 17, wherein the chemotherapeutic agent comprises one or more of bortezomib, lenalidomide, temozolomide, 5-fluorouracil (5-FU), 6-mercaptopurine (6-MP), Capecitabine, Cladribine, Clofarabine, Cytarabine, Floxuridine, Fludarabine, Gemcitabine, Hydroxyurea, Methotrexate, Pemetrexed, Pentostatin, Thioguanine, daunorubicin; doxorubicin, epirubicin, idaurubicin, topotecan, irinotecan, etoposide, teniposide, mitoxantrone, Vinblastine, vincristine, vinorelbine, estramustine, paclitaxel, dexamethasone, and docetaxel.

19. The method of claim 17, wherein the immunotherapeutic agent comprises one or more of nivolumab, pembrolizumab, pidilizumab, durvalumab, atezolizumab, and avelumab, and any fragment, derivative, conjugate, variant, radioisotope-labeled complex, or biosimilar thereof.

20. The method of claim 17, wherein the immunotherapeutic agent comprises one or more of rituximab, trastuzumab, ibritumomab, tositumomab, cetuximab, bevacizumab, gemtuzumab, alemtuzumab, and BL22, and any fragment, derivative, conjugate, variant, radioisotope-labeled complex, or biosimilar thereof.

* * * * *

SEQUENCE LISTING

<160> NUMBER OF SEQ ID NOS: 70

<210> SEQ ID NO 1
<211> LENGTH: 440
<212> TYPE: PRT
<213> ORGANISM: Artificial Sequence
<220> FEATURE:
<223> OTHER INFORMATION: nivolumab heavy chain

<400> SEQUENCE: 1

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350
```

```
Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
        435                 440

<210> SEQ ID NO 2
<211> LENGTH: 214
<212> TYPE: PRT
<213> ORGANISM: Artificial Sequence
<220> FEATURE:
<223> OTHER INFORMATION: nivolumab light chain

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 113
<212> TYPE: PRT
<213> ORGANISM: Artificial Sequence
<220> FEATURE:
<223> OTHER INFORMATION: nivolumab variable heavy chain
```

```
<400> SEQUENCE: 3

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 4
<211> LENGTH: 107
<212> TYPE: PRT
<213> ORGANISM: Artificial Sequence
<220> FEATURE:
<223> OTHER INFORMATION: nivolumab variable light chain

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: nivolumab heavy chain CDR1

<400> SEQUENCE: 5

Asn Ser Gly Met His
1               5

<210> SEQ ID NO 6
<211> LENGTH: 17
<212> TYPE: PRT
<213> ORGANISM: Artificial Sequence
<220> FEATURE:
<223> OTHER INFORMATION: nivolumab heavy chain CDR2
```

```
<400> SEQUENCE: 6

Val Ile Trp Tyr Asp Gly Ser Lys Arg Tyr Tyr Ala Asp Ser Val Lys
1               5                   10                  15

Gly

<210> SEQ ID NO 7
<211> LENGTH: 4
<212> TYPE: PRT
<213> ORGANISM: Artificial Seqence
<220> FEATURE:
<223> OTHER INFORMATION: nivolumab heavy chain CDR3

<400> SEQUENCE: 7

Asn Asp Asp Tyr
1

<210> SEQ ID NO 8
<211> LENGTH: 11
<212> TYPE: PRT
<213> ORGANISM: Artificial Sequence
<220> FEATURE:
<223> OTHER INFORMATION: nivolumab light chain CDR1

<400> SEQUENCE: 8

Arg Ala Ser Gln Ser Val Ser Ser Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: nivolumab light chain CDR2

<400> SEQUENCE: 9

Asp Ala Ser Asn Arg Ala Thr
1               5

<210> SEQ ID NO 10
<211> LENGTH: 9
<212> TYPE: PRT
<213> ORGANISM: Artificial Sequence
<220> FEATURE:
<223> OTHER INFORMATION: nivolumab light chain CDR3

<400> SEQUENCE: 10

Gln Gln Ser Ser Asn Trp Pro Arg Thr
1               5

<210> SEQ ID NO 11
<211> LENGTH: 447
<212> TYPE: PRT
<213> ORGANISM: Artificial Sequence
<220> FEATURE:
<223> OTHER INFORMATION: pembrolizumab heavy chain

<400> SEQUENCE: 11

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45
```

```
Gly Gly Ile Asn Pro Ser Asn Gly Gly Thr Asn Phe Asn Glu Lys Phe
         50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 12
<211> LENGTH: 218
<212> TYPE: PRT
```

<213> ORGANISM: Artificial Sequence
<220> FEATURE:
<223> OTHER INFORMATION: pembrolizumab light chain

<400> SEQUENCE: 12

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 13
<211> LENGTH: 120
<212> TYPE: PRT
<213> ORGANISM: Artificial Sequence
<220> FEATURE:
<223> OTHER INFORMATION: pembrolizumab variable heavy chain

<400> SEQUENCE: 13

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110
```

Gly Thr Thr Val Thr Val Ser Ser
        115                 120

<210> SEQ ID NO 14
<211> LENGTH: 111
<212> TYPE: PRT
<213> ORGANISM: Artificial Sequence
<220> FEATURE:
<223> OTHER INFORMATION: pembrolizumab variable light chain

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 15
<211> LENGTH: 5
<212> TYPE: PRT
<213> ORGANISM: Artificial Sequence
<220> FEATURE:
<223> OTHER INFORMATION: pembrolizumab heavy chain CDR1

<400> SEQUENCE: 15

Asn Tyr Tyr Met Tyr
1               5

<210> SEQ ID NO 16
<211> LENGTH: 16
<212> TYPE: PRT
<213> ORGANISM: Artificial Sequence
<220> FEATURE:
<223> OTHER INFORMATION: pembrolizumab heavy chain CDR2

<400> SEQUENCE: 16

Gly Ile Asn Pro Ser Asn Gly Gly Thr Asn Phe Asn Glu Lys Phe Lys
1               5                   10                  15

<210> SEQ ID NO 17
<211> LENGTH: 11
<212> TYPE: PRT
<213> ORGANISM: Artificial Sequence
<220> FEATURE:
<223> OTHER INFORMATION: pembrolizumab heavy chain CDR3

<400> SEQUENCE: 17

Arg Asp Tyr Arg Phe Asp Met Gly Phe Asp Tyr
1               5                   10

<210> SEQ ID NO 18
<211> LENGTH: 15
<212> TYPE: PRT
<213> ORGANISM: Artificial Sequence
<220> FEATURE:

<223> OTHER INFORMATION: pembrolizumab light chain CDR1

<400> SEQUENCE: 18

Arg Ala Ser Lys Gly Val Ser Thr Ser Gly Tyr Ser Tyr Leu His
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: pembrolizumab light chain CDR2

<400> SEQUENCE: 19

Leu Ala Ser Tyr Leu Glu Ser
1               5

<210> SEQ ID NO 20
<211> LENGTH: 9
<212> TYPE: PRT
<213> ORGANISM: Artificial Sequence
<220> FEATURE:
<223> OTHER INFORMATION: pembrolizumab light chain CDR3

<400> SEQUENCE: 20

Gln His Ser Arg Asp Leu Pro Leu Thr
1               5

<210> SEQ ID NO 21
<211> LENGTH: 447
<212> TYPE: PRT
<213> ORGANISM: Artificial Sequence
<220> FEATURE:
<223> OTHER INFORMATION: pidilizumab heavy chain

<400> SEQUENCE: 21

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 22
<211> LENGTH: 213
<212> TYPE: PRT
<213> ORGANISM: Artificial Sequence
<220> FEATURE:
<223> OTHER INFORMATION: pidilizumab light chain

<400> SEQUENCE: 22

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys Arg Thr Val Ala Ala Pro
            100                 105                 110

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 23
<211> LENGTH: 117
<212> TYPE: PRT
<213> ORGANISM: Artificial Sequence
<220> FEATURE:
<223> OTHER INFORMATION: pidilizumab variable heavy chain

<400> SEQUENCE: 23

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115

<210> SEQ ID NO 24
<211> LENGTH: 106
<212> TYPE: PRT
<213> ORGANISM: Artificial Sequence
<220> FEATURE:
<223> OTHER INFORMATION: pidilizumab variable light chain

<400> SEQUENCE: 24

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80
```

```
Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 25
<211> LENGTH: 451
<212> TYPE: PRT
<213> ORGANISM: Artificial Sequence
<220> FEATURE:
<223> OTHER INFORMATION: durvalumab (MEDI4736) heavy chain

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335
```

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 26
<211> LENGTH: 265
<212> TYPE: PRT
<213> ORGANISM: Artificial Sequence
<220> FEATURE:
<223> OTHER INFORMATION: durvalumab (MEDI4736) light chain

<400> SEQUENCE: 26

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
            35                  40                  45

Ala Asn Glu Ile Val Leu Thr Gln Ser Pro Gly Thr Leu Ser Leu Ser
        50                  55                  60

Pro Gly Glu Arg Ala Thr Leu Ser Cys Arg Ala Ser Gln Arg Val Ser
65                  70                  75                  80

Ser Ser Tyr Leu Ala Trp Tyr Gln Gln Lys Pro Gly Gln Ala Pro Arg
                85                  90                  95

Leu Leu Ile Tyr Asp Ala Ser Ser Arg Ala Thr Gly Ile Pro Asp Arg
            100                 105                 110

Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
    130                 135                 140

Leu Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

```
Lys Val Tyr Ala Cys Glu Val Thr His Gln Gly Leu Ser Ser Pro Val
                245                 250                 255

Thr Lys Ser Phe Asn Arg Gly Glu Cys
        260                 265

<210> SEQ ID NO 27
<211> LENGTH: 121
<212> TYPE: PRT
<213> ORGANISM: Artificial Sequence
<220> FEATURE:
<223> OTHER INFORMATION: durvalumab variable heavy chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 28
<211> LENGTH: 108
<212> TYPE: PRT
<213> ORGANISM: Artificial Sequence
<220> FEATURE:
<223> OTHER INFORMATION: durvalumab variable light chain

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 29
<211> LENGTH: 5
<212> TYPE: PRT
<213> ORGANISM: Artificial Sequence
<220> FEATURE:
<223> OTHER INFORMATION: durvalumab heavy chain CDR1
```

```
<400> SEQUENCE: 29

Arg Tyr Trp Met Ser
1               5

<210> SEQ ID NO 30
<211> LENGTH: 17
<212> TYPE: PRT
<213> ORGANISM: Artificial Sequence
<220> FEATURE:
<223> OTHER INFORMATION: durvalumab heavy chain CDR2

<400> SEQUENCE: 30

Asn Ile Lys Gln Asp Gly Ser Glu Lys Tyr Tyr Val Asp Ser Val Lys
1               5                   10                  15

Gly

<210> SEQ ID NO 31
<211> LENGTH: 12
<212> TYPE: PRT
<213> ORGANISM: Artificial Sequence
<220> FEATURE:
<223> OTHER INFORMATION: durvalumab heavy chain CDR3

<400> SEQUENCE: 31

Glu Gly Gly Trp Phe Gly Glu Leu Ala Phe Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: durvalumab light chain CDR1

<400> SEQUENCE: 32

Arg Ala Ser Gln Arg Val Ser Ser Ser Tyr Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: durvalumab light chain CDR2

<400> SEQUENCE: 33

Asp Ala Ser Ser Arg Ala Thr
1               5

<210> SEQ ID NO 34
<211> LENGTH: 9
<212> TYPE: PRT
<213> ORGANISM: Artificial Sequence
<220> FEATURE:
<223> OTHER INFORMATION: durvalumab light chain CDR3

<400> SEQUENCE: 34

Gln Gln Tyr Gly Ser Leu Pro Trp Thr
1               5

<210> SEQ ID NO 35
<211> LENGTH: 448
<212> TYPE: PRT
<213> ORGANISM: Artificial Sequence
<220> FEATURE:
```

<223> OTHER INFORMATION: atezolizumab (MPDL3280A) heavy chain

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 36
<211> LENGTH: 214
<212> TYPE: PRT
<213> ORGANISM: Artificial Sequence
<220> FEATURE:
<223> OTHER INFORMATION: atezolizumab (MPDL3280A) light chain

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 118
<212> TYPE: PRT
<213> ORGANISM: Artificial Sequence
<220> FEATURE:
<223> OTHER INFORMATION: atezolizumab variable heavy chain

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45
```

-continued

```
Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ala
            115

<210> SEQ ID NO 38
<211> LENGTH: 108
<212> TYPE: PRT
<213> ORGANISM: Artificial Sequence
<220> FEATURE:
<223> OTHER INFORMATION: atezolizumab variable light chain

<400> SEQUENCE: 38

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg
                100                 105

<210> SEQ ID NO 39
<211> LENGTH: 10
<212> TYPE: PRT
<213> ORGANISM: Artificial Sequence
<220> FEATURE:
<223> OTHER INFORMATION: atezolizumab heavy chain CDR1
<220> FEATURE:
<221> NAME/KEY: misc_feature
<222> LOCATION: (6)..(6)
<223> OTHER INFORMATION: Xaa can be any naturally occurring amino acid

<400> SEQUENCE: 39

Gly Phe Thr Phe Ser Xaa Ser Trp Ile His
 1               5                  10

<210> SEQ ID NO 40
<211> LENGTH: 18
<212> TYPE: PRT
<213> ORGANISM: Artificial Sequence
<220> FEATURE:
<223> OTHER INFORMATION: atezolizumab heavy chain CDR2
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
```

```
<400> SEQUENCE: 40

Ala Trp Ile Xaa Pro Tyr Gly Gly Ser Xaa Tyr Tyr Ala Asp Ser Val
1               5                   10                  15

Lys Gly

<210> SEQ ID NO 41
<211> LENGTH: 9
<212> TYPE: PRT
<213> ORGANISM: Artificial Sequence
<220> FEATURE:
<223> OTHER INFORMATION: atezolizumab heavy chain CDR3

<400> SEQUENCE: 41

Arg His Trp Pro Gly Gly Phe Asp Tyr
1               5

<210> SEQ ID NO 42
<211> LENGTH: 11
<212> TYPE: PRT
<213> ORGANISM: Artificial Sequence
<220> FEATURE:
<223> OTHER INFORMATION: atezolizumab light chain CDR1
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 42

Arg Ala Ser Gln Xaa Xaa Xaa Thr Xaa Xaa Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: atezolizumab light chain CDR2
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 43

Ser Ala Ser Xaa Leu Xaa Ser
1               5

<210> SEQ ID NO 44
<211> LENGTH: 9
<212> TYPE: PRT
<213> ORGANISM: Artificial Sequence
<220> FEATURE:
<223> OTHER INFORMATION: atezolizumab light chain CDR3
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
```

```
<400> SEQUENCE: 44

Gln Gln Xaa Xaa Xaa Xaa Pro Xaa Thr
1               5

<210> SEQ ID NO 45
<211> LENGTH: 450
<212> TYPE: PRT
<213> ORGANISM: Artificial Sequence
<220> FEATURE:
<223> OTHER INFORMATION: avelumab (MSB0010718C) heavy chain

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 46
<211> LENGTH: 216
<212> TYPE: PRT
<213> ORGANISM: Artificial Sequence
<220> FEATURE:
<223> OTHER INFORMATION: avelumab (MSB0010718C) light chain

<400> SEQUENCE: 46

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
            85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 47
```

```
<211> LENGTH: 120
<212> TYPE: PRT
<213> ORGANISM: Artificial Sequence
<220> FEATURE:
<223> OTHER INFORMATION: avelumab variable heavy chain

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Val Asp Tyr Trp Gly Gln Gly
            100                 105                 110

Gly Thr Leu Val Thr Val Ser Ser
        115                 120

<210> SEQ ID NO 48
<211> LENGTH: 110
<212> TYPE: PRT
<213> ORGANISM: Artificial Sequence
<220> FEATURE:
<223> OTHER INFORMATION: avelumab variable light chain

<400> SEQUENCE: 48

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 49
<211> LENGTH: 5
<212> TYPE: PRT
<213> ORGANISM: Artificial Sequence
<220> FEATURE:
<223> OTHER INFORMATION: avelumab heavy chain CDR1

<400> SEQUENCE: 49

Ser Tyr Ile Met Met
1               5

<210> SEQ ID NO 50
<211> LENGTH: 17
```

```
<212> TYPE: PRT
<213> ORGANISM: Artificial Sequence
<220> FEATURE:
<223> OTHER INFORMATION: avelumab heavy chain CDR2

<400> SEQUENCE: 50

Ser Ile Tyr Pro Ser Gly Gly Ile Thr Phe Tyr Ala Asp Thr Val Lys
1               5                   10                  15

Gly

<210> SEQ ID NO 51
<211> LENGTH: 11
<212> TYPE: PRT
<213> ORGANISM: Artificial Sequence
<220> FEATURE:
<223> OTHER INFORMATION: avelumab heavy chain CDR3

<400> SEQUENCE: 51

Ile Lys Leu Gly Thr Val Thr Thr Val Asp Tyr
1               5                   10

<210> SEQ ID NO 52
<211> LENGTH: 14
<212> TYPE: PRT
<213> ORGANISM: Artificial Sequence
<220> FEATURE:
<223> OTHER INFORMATION: avelumab light chain CDR1

<400> SEQUENCE: 52

Thr Gly Thr Ser Ser Asp Val Gly Gly Tyr Asn Tyr Val Ser
1               5                   10

<210> SEQ ID NO 53
<211> LENGTH: 7
<212> TYPE: PRT
<213> ORGANISM: Artificial Sequence
<220> FEATURE:
<223> OTHER INFORMATION: avelumab light chain CDR2

<400> SEQUENCE: 53

Asp Val Ser Asn Arg Pro Ser
1               5

<210> SEQ ID NO 54
<211> LENGTH: 10
<212> TYPE: PRT
<213> ORGANISM: Artificial Sequence
<220> FEATURE:
<223> OTHER INFORMATION: avelumab light chain CDR3

<400> SEQUENCE: 54

Ser Ser Tyr Thr Ser Ser Ser Thr Arg Val
1               5                   10

<210> SEQ ID NO 55
<211> LENGTH: 451
<212> TYPE: PRT
<213> ORGANISM: Artificial Sequence
<220> FEATURE:
<223> OTHER INFORMATION: rituximab heavy chain

<400> SEQUENCE: 55

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30
```

-continued

Asn Met His Trp Val Lys Gln Thr Pro Gly Arg Gly Leu Glu Trp Ile
             35                  40                  45
Gly Ala Ile Tyr Pro Gly Asn Gly Asp Thr Ser Tyr Asn Gln Lys Phe
         50                  55                  60
Lys Gly Lys Ala Thr Leu Thr Ala Asp Lys Ser Ser Ser Thr Ala Tyr
65                  70                  75                  80
Met Gln Leu Ser Ser Leu Thr Ser Glu Asp Ser Ala Val Tyr Tyr Cys
                 85                  90                  95
Ala Arg Ser Thr Tyr Tyr Gly Gly Asp Trp Tyr Phe Asn Val Trp Gly
             100                 105                 110
Ala Gly Thr Thr Val Thr Val Ser Ala Ala Ser Thr Lys Gly Pro Ser
             115                 120                 125
Val Phe Pro Leu Ala Pro Ser Ser Lys Ser Thr Ser Gly Gly Thr Ala
             130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
             165                 170                 175
Val Leu Gln Ser Ser Gly Leu Tyr Ser Leu Ser Ser Val Val Thr Val
             180                 185                 190
Pro Ser Ser Ser Leu Gly Thr Gln Thr Tyr Ile Cys Asn Val Asn His
             195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
             245                 250                 255
Ile Ser Arg Thr Pro Glu Val Thr Cys Val Val Val Asp Val Ser His
             260                 265                 270
Glu Asp Pro Glu Val Lys Phe Asn Trp Tyr Val Asp Gly Val Glu Val
             275                 280                 285
His Asn Ala Lys Thr Lys Pro Arg Glu Glu Gln Tyr Asn Ser Thr Tyr
             290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
             325                 330                 335
Glu Lys Thr Ile Ser Lys Ala Lys Gly Gln Pro Arg Glu Pro Gln Val
             340                 345                 350
Tyr Thr Leu Pro Pro Ser Arg Asp Glu Leu Thr Lys Asn Gln Val Ser
             355                 360                 365
Leu Thr Cys Leu Val Lys Gly Phe Tyr Pro Ser Asp Ile Ala Val Glu
         370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
             405                 410                 415
Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
            435                 440                 445

Pro Gly Lys
    450

<210> SEQ ID NO 56
<211> LENGTH: 213
<212> TYPE: PRT
<213> ORGANISM: Artificial Sequence
<220> FEATURE:
<223> OTHER INFORMATION: rituximab light chain

<400> SEQUENCE: 56

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 57
<211> LENGTH: 451
<212> TYPE: PRT
<213> ORGANISM: Artificial Sequence
<220> FEATURE:
<223> OTHER INFORMATION: trastuzumab heavy chain

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Pro Lys Ser Cys
     210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                 245                 250                 255

Ile Ser Arg Thr Pro Glu Val Thr Cys Val Val Val Asp Val Ser His
             260                 265                 270

Glu Asp Pro Glu Val Lys Phe Asn Trp Tyr Val Asp Gly Val Glu Val
         275                 280                 285

His Asn Ala Lys Thr Lys Pro Arg Glu Glu Gln Tyr Asn Ser Thr Tyr
     290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                 325                 330                 335

Glu Lys Thr Ile Ser Lys Ala Lys Gly Gln Pro Arg Glu Pro Gln Val
             340                 345                 350

Tyr Thr Leu Pro Pro Ser Arg Asp Glu Leu Thr Lys Asn Gln Val Ser
         355                 360                 365

Leu Thr Cys Leu Val Lys Gly Phe Tyr Pro Ser Asp Ile Ala Val Glu
     370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
         435                 440                 445

Pro Gly Lys
     450

```
<210> SEQ ID NO 58
<211> LENGTH: 214
<212> TYPE: PRT
<213> ORGANISM: Artificial Sequence
<220> FEATURE:
<223> OTHER INFORMATION: trastuzumab light chain

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 443
<212> TYPE: PRT
<213> ORGANISM: Artificial Sequence
<220> FEATURE:
<223> OTHER INFORMATION: ibritumomab heavy chain

<400> SEQUENCE: 59

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95
```

-continued

```
Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
            115                 120                 125

Ala Pro Val Cys Gly Asp Thr Gly Ser Ser Val Thr Leu Gly Cys
            130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Val Thr Val Thr Ser Ser Thr Trp
            180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
            210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
            290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
            435                 440
```

<210> SEQ ID NO 60
<211> LENGTH: 209
<212> TYPE: PRT
<213> ORGANISM: Artificial Sequence
<220> FEATURE:
<223> OTHER INFORMATION: ibritumomab light chain

<400> SEQUENCE: 60

```
Gln Ile Val Leu Ser Gln Ser Pro Ala Ile Leu Ser Ala Ser Pro Gly
1               5                   10                  15
```

```
Glu Lys Val Thr Met Thr Cys Arg Ala Ser Ser Val Ser Tyr Met
            20                  25                  30
His Trp Tyr Gln Gln Lys Pro Gly Ser Ser Pro Lys Pro Trp Ile Tyr
            35                  40                  45
Ala Pro Ser Asn Leu Ala Ser Gly Val Pro Ala Arg Phe Ser Gly Ser
50                      55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Ser Phe Asn Pro Pro Thr
                85                  90                  95
Phe Gly Ala Gly Thr Lys Leu Glu Leu Lys Arg Ala Asp Ala Ala Pro
                100                 105                 110
Thr Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
                180                 185                 190
Cys Glu Val Thr His Gln Gly Leu Ser Ser Pro Val Thr Lys Ser Phe
                195                 200                 205
Asn

<210> SEQ ID NO 61
<211> LENGTH: 447
<212> TYPE: PRT
<213> ORGANISM: Artificial Sequence
<220> FEATURE:
<223> OTHER INFORMATION: tositumomab heavy chain

<400> SEQUENCE: 61

Gln Ala Tyr Leu Gln Gln Ser Gly Ala Glu Leu Val Arg Pro Gly Ala
1               5                   10                  15
Ser Val Lys Met Ser Cys Lys Ala Ser Gly Tyr Thr Phe Thr Ser Tyr
            20                  25                  30
Asn Met His Trp Val Lys Gln Thr Pro Arg Gln Gly Leu Glu Trp Ile
            35                  40                  45
Gly Ala Ile Tyr Pro Gly Asn Gly Asp Thr Ser Tyr Asn Gln Lys Phe
50                  55                  60
Lys Gly Lys Ala Thr Leu Thr Val Asp Lys Ser Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Val Val Tyr Tyr Ser Asn Ser Tyr Trp Tyr Phe Asp Val Trp
                100                 105                 110
Gly Thr Gly Thr Thr Val Thr Val Ser Gly Pro Ser Val Phe Pro Leu
            115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 62
<211> LENGTH: 210
<212> TYPE: PRT
<213> ORGANISM: Artificial Sequence
<220> FEATURE:
<223> OTHER INFORMATION: tositumomab light chain

<400> SEQUENCE: 62

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
            35                  40                  45

Ala Pro Ser Asn Leu Ala Ser Gly Val Pro Ala Arg Phe Ser Gly Ser
            50                  55                  60

Gly Ser Gly Thr Ser Tyr Ser Leu Thr Ile Ser Arg Val Glu Ala Glu
65                  70                  75                  80
```

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
210

<210> SEQ ID NO 63
<211> LENGTH: 452
<212> TYPE: PRT
<213> ORGANISM: Artificial Sequence
<220> FEATURE:
<223> OTHER INFORMATION: cetuximab heavy chain

<400> SEQUENCE: 63

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

-continued

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 64
<211> LENGTH: 213
<212> TYPE: PRT
<213> ORGANISM: Artificial Sequence
<220> FEATURE:
<223> OTHER INFORMATION: cetuximab light chain

<400> SEQUENCE: 64

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 65
<211> LENGTH: 453
<212> TYPE: PRT
<213> ORGANISM: Artificial Sequence
<220> FEATURE:
<223> OTHER INFORMATION: bevacizumab heavy chain

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 66
<211> LENGTH: 214
<212> TYPE: PRT
<213> ORGANISM: Artificial Sequence
<220> FEATURE:
<223> OTHER INFORMATION: bevacizumab Light chain

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 116
<212> TYPE: PRT
<213> ORGANISM: Artificial Sequence
<220> FEATURE:
<223> OTHER INFORMATION: gemtuzumab heavy chain

<400> SEQUENCE: 67

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Arg Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Ala Arg Gly Gly Gly Val Phe Asp Tyr Trp Gly Gln Gly Thr Thr Leu
            100                 105                 110

Thr Val Ser Ser
        115

<210> SEQ ID NO 68
<211> LENGTH: 106
<212> TYPE: PRT
<213> ORGANISM: Artificial Sequence
<220> FEATURE:
<223> OTHER INFORMATION: gemtuzumab Light chain

<400> SEQUENCE: 68

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Ile Ser Tyr Met
            20                  25                  30

His Trp Phe Gln Gln Lys Pro Gly Thr Ser Pro Lys Leu Trp Ile Tyr
        35                  40                  45

Thr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Thr Tyr Pro Leu Thr
                85                  90                  95

Phe Gly Ser Gly Thr Lys Leu Glu Leu Lys
            100                 105

<210> SEQ ID NO 69
<211> LENGTH: 451
<212> TYPE: PRT
<213> ORGANISM: Artificial Sequence
```

<220> FEATURE:
<223> OTHER INFORMATION: alemtuzumab heavy chain

<400> SEQUENCE: 69

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 70
<211> LENGTH: 211
<212> TYPE: PRT
<213> ORGANISM: Artificial Sequence
<220> FEATURE:
<223> OTHER INFORMATION: alemtuzumab Light chain

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210
```